(12) United States Patent
Jung et al.

(10) Patent No.: US 7,739,510 B2
(45) Date of Patent: Jun. 15, 2010

(54) ALERT OPTIONS FOR ELECTRONIC-PAPER VERIFICATION

(75) Inventors: Edward K. Y. Jung, Bellevue, WA (US);
Royce A. Levien, Lexington, MA (US);
Mark A. Malamud, Seattle, WA (US);
John D. Rinaldo, Jr., Bellevue, WA (US)

(73) Assignee: The Invention Science Fund I, Inc, Bellevue, WA (US)

( * ) Notice: Subject to any disclaimer, the term of this patent is extended or adjusted under 35 U.S.C. 154(b) by 1434 days.

(21) Appl. No.: 11/129,020

(22) Filed: May 12, 2005

(65) Prior Publication Data

US 2006/0259773 A1 Nov. 16, 2006

(51) Int. Cl.
*H04L 9/32* (2006.01)
*G06F 21/00* (2006.01)

(52) U.S. Cl. .......................... 713/176; 726/26

(58) Field of Classification Search .................. 713/176; 726/2, 21, 26, 27, 30; 235/375, 382, 383; 705/50, 64, 67, 76
See application file for complete search history.

(56) References Cited

U.S. PATENT DOCUMENTS

| | | | |
|---|---|---|---|
| 5,371,796 A | 12/1994 | Avarne | |
| 5,649,260 A | 7/1997 | Wheeler et al. | |
| 5,850,442 A | 12/1998 | Muftic | |
| 5,867,577 A | 2/1999 | Patarin | |
| 5,917,925 A | 6/1999 | Moore | |
| 5,991,411 A * | 11/1999 | Kaufman et al. | 705/67 |
| 6,098,882 A | 8/2000 | Antognini et al. | |
| 6,216,116 B1 | 4/2001 | Barkan et al. | |
| 6,252,564 B1 | 6/2001 | Albert et al. | |
| 6,419,618 B1 | 7/2002 | Mackinlay et al. | |
| 6,480,958 B1 | 11/2002 | Harrington | |
| 6,521,958 B1 | 2/2003 | Forbes et al. | |
| 6,658,415 B1 | 12/2003 | Brown et al. | |
| 6,694,217 B2 | 2/2004 | Bloom | |
| 6,710,754 B2 | 3/2004 | Hanson et al. | |
| 6,753,830 B2 | 6/2004 | Gelbman | |

(Continued)

FOREIGN PATENT DOCUMENTS

EP 0578 935 A2 1/1994

(Continued)

OTHER PUBLICATIONS

Dybwad, Barb; "Philips Promises Foldable Paper Displays Ready Within 2 Years"; bearing a date of Mar. 7, 2005; p. 1; located at http://www.engadget.com/2005/03/07/philips-promises-foldable-paper-displays-ready-within-2-years/.

(Continued)

*Primary Examiner*—Gilberto Barron, Jr.
*Assistant Examiner*—Abdulhakim Nobahar

(57) ABSTRACT

A system and method to control the writing on electronic paper (e-paper). An e-paper device may incorporate authentication indicia as part of informational data written on e-paper material. The informational data is protected by a security methodology that is accessible to authorized entities. A reader device may be used to help make a verification determination of whether encrypted or encoded data has been altered. In some instances an output alert operably coupled to the reader device serves as a verification status indicator.

37 Claims, 33 Drawing Sheets

U.S. PATENT DOCUMENTS

| | | |
|---|---|---|
| 6,812,851 B1 | 11/2004 | Dukach et al. |
| 6,850,209 B2 | 2/2005 | Mankins et al. |
| 6,857,565 B2 | 2/2005 | Smith |
| 6,864,875 B2 | 3/2005 | Drzaic et al. |
| 6,885,032 B2 | 4/2005 | Forbes et al. |
| 6,924,781 B1 | 8/2005 | Gelbman |
| 6,947,571 B1 | 9/2005 | Rhoads et al. |
| 7,032,014 B2 | 4/2006 | Thiyagarajan et al. |
| 7,073,129 B1 | 7/2006 | Robarts et al. |
| 7,111,230 B2 | 9/2006 | Euchner et al. |
| 7,134,606 B2 | 11/2006 | Chou |
| 7,167,844 B1 * | 1/2007 | Leong et al. ........... 705/80 |
| 7,170,391 B2 | 1/2007 | Lane et al. |
| 7,174,031 B2 | 2/2007 | Rhoads et al. |
| 7,221,258 B2 | 5/2007 | Lane et al. |
| 7,223,030 B2 | 5/2007 | Fessler et al. |
| 7,225,175 B2 | 5/2007 | Higgins et al. |
| 7,243,840 B2 | 7/2007 | Bason et al. |
| 7,261,478 B2 | 8/2007 | Marowski et al. |
| 7,321,363 B2 | 1/2008 | Yoshida et al. |
| 7,329,186 B2 | 2/2008 | Griswold et al. |
| 7,333,001 B2 | 2/2008 | Lane et al. |
| 7,350,716 B2 | 4/2008 | Gilfix et al. |
| 7,357,333 B2 | 4/2008 | Gilfix |
| 7,404,521 B2 | 7/2008 | Parkos et al. |
| 7,424,535 B2 | 9/2008 | Karaoguz et al. |
| 7,475,432 B2 * | 1/2009 | Carpentier et al. ........... 726/30 |
| 7,539,622 B1 * | 5/2009 | Harris et al. ........... 705/1 |
| 2001/0000191 A1 * | 4/2001 | Barkan et al. ........... 705/59 |
| 2001/0020935 A1 * | 9/2001 | Gelbman ........... 345/173 |
| 2002/0005832 A1 | 1/2002 | Katase |
| 2002/0009978 A1 | 1/2002 | Dukach et al. |
| 2002/0019885 A1 | 2/2002 | Sleeper |
| 2002/0026425 A1 | 2/2002 | Fahraeus |
| 2002/0065046 A1 | 5/2002 | Mankins et al. |
| 2002/0080959 A1 | 6/2002 | Weller |
| 2002/0084891 A1 | 7/2002 | Mankins et al. |
| 2002/0111146 A1 | 8/2002 | Fridman et al. |
| 2002/0112026 A1 | 8/2002 | Fridman et al. |
| 2002/0118165 A1 | 8/2002 | McGowan et al. |
| 2002/0128967 A1 | 9/2002 | Meyer et al. |
| 2002/0135805 A1 | 9/2002 | Fahraeus et al. |
| 2002/0164962 A1 | 11/2002 | Mankins et al. |
| 2002/0180751 A1 | 12/2002 | Rozzi |
| 2002/0180767 A1 | 12/2002 | Northway et al. |
| 2003/0005369 A1 | 1/2003 | Trelewicz et al. |
| 2003/0016844 A1 | 1/2003 | Numaoka |
| 2003/0020701 A1 | 1/2003 | Nakamura et al. |
| 2003/0046184 A1 | 3/2003 | Bjorklund et al. |
| 2003/0055689 A1 | 3/2003 | Block et al. |
| 2003/0071780 A1 | 4/2003 | Vincent et al. |
| 2003/0095401 A1 | 5/2003 | Hanson et al. |
| 2003/0103034 A1 | 6/2003 | Silverbrook et al. |
| 2003/0111526 A1 | 6/2003 | Smith |
| 2003/0122924 A1 | 7/2003 | Meyers |
| 2003/0132924 A1 * | 7/2003 | Hamilton ........... 345/204 |
| 2003/0134460 A1 | 7/2003 | Forbes et al. |
| 2003/0182238 A1 | 9/2003 | Brookner et al. |
| 2003/0183685 A1 | 10/2003 | Moore et al. |
| 2003/0197887 A1 | 10/2003 | Shenoy et al. |
| 2003/0200288 A1 | 10/2003 | Thiyagarajan et al. |
| 2003/0231374 A1 | 12/2003 | Vincent et al. |
| 2004/0005051 A1 | 1/2004 | Wheeler et al. |
| 2004/0023397 A1 | 2/2004 | Vig et al. |
| 2004/0036622 A1 | 2/2004 | Dukach et al. |
| 2004/0039932 A1 | 2/2004 | Elazar et al. |
| 2004/0041785 A1 | 3/2004 | Stevens et al. |
| 2004/0044682 A1 | 3/2004 | Nakamura et al. |
| 2004/0046025 A1 | 3/2004 | Lebaschi et al. |
| 2004/0070633 A1 | 4/2004 | Nakamura et al. |
| 2004/0084530 A1 | 5/2004 | McQueen et al. |
| 2004/0088680 A1 | 5/2004 | Pieper et al. |
| 2004/0093568 A1 | 5/2004 | Lerner et al. |
| 2004/0099736 A1 | 5/2004 | Neumark |
| 2004/0108504 A1 | 6/2004 | Forbes et al. |
| 2004/0110326 A1 | 6/2004 | Forbes et al. |
| 2004/0117853 A1 | 6/2004 | Karaoguz et al. |
| 2004/0156170 A1 | 8/2004 | Mager et al. |
| 2004/0160319 A1 | 8/2004 | Joao |
| 2004/0179001 A1 | 9/2004 | Morrison et al. |
| 2004/0189672 A1 | 9/2004 | Yamazaki et al. |
| 2004/0190080 A1 | 9/2004 | Kodama et al. |
| 2004/0193949 A1 | 9/2004 | Hirotsune et al. |
| 2004/0196313 A1 | 10/2004 | Wynn et al. |
| 2004/0196834 A1 | 10/2004 | Ofek et al. |
| 2004/0212600 A1 | 10/2004 | Kodama et al. |
| 2004/0216031 A1 | 10/2004 | Taylor |
| 2004/0217399 A1 | 11/2004 | Drewes |
| 2004/0221043 A1 | 11/2004 | Su et al. |
| 2004/0230542 A1 | 11/2004 | Obrea |
| 2004/0233040 A1 | 11/2004 | Lane et al. |
| 2004/0268130 A1 | 12/2004 | Pretorius |
| 2005/0021695 A1 | 1/2005 | Takamine |
| 2005/0024353 A1 | 2/2005 | Amundson et al. |
| 2005/0038756 A1 | 2/2005 | Nagel |
| 2005/0044417 A1 | 2/2005 | Carpentier et al. |
| 2005/0079386 A1 | 4/2005 | Brown, Jr. et al. |
| 2005/0092841 A1 | 5/2005 | Barkan |
| 2005/0096938 A1 | 5/2005 | Slomkowski et al. |
| 2005/0097019 A1 | 5/2005 | Jacobs |
| 2005/0097047 A1 | 5/2005 | Drummond et al. |
| 2005/0099398 A1 | 5/2005 | Garside et al. |
| 2005/0104844 A1 | 5/2005 | Nakai et al. |
| 2005/0114672 A1 | 5/2005 | Duncan et al. |
| 2005/0137948 A1 | 6/2005 | Kissner et al. |
| 2005/0138541 A1 | 6/2005 | Euchner et al. |
| 2005/0139666 A1 | 6/2005 | Chou |
| 2005/0150944 A1 * | 7/2005 | Melick et al. ........... 235/375 |
| 2005/0156870 A1 | 7/2005 | Flinner et al. |
| 2005/0161501 A1 | 7/2005 | Giering et al. |
| 2005/0187937 A1 | 8/2005 | Kawabe et al. |
| 2005/0188306 A1 | 8/2005 | Mackenzie |
| 2005/0192884 A1 | 9/2005 | Raines |
| 2005/0211783 A1 | 9/2005 | Chou |
| 2005/0213790 A1 | 9/2005 | Rhoads et al. |
| 2005/0230962 A1 | 10/2005 | Berson |
| 2005/0243369 A1 | 11/2005 | Goldstein et al. |
| 2005/0246621 A1 | 11/2005 | Ogawa et al. |
| 2005/0247797 A1 | 11/2005 | Ramachandran |
| 2005/0253802 A1 | 11/2005 | Wright |
| 2005/0262350 A1 | 11/2005 | Boutant et al. |
| 2005/0274794 A1 | 12/2005 | Bason et al. |
| 2005/0280627 A1 | 12/2005 | Koshimizu et al. |
| 2005/0289345 A1 | 12/2005 | Haas et al. |
| 2006/0005050 A1 | 1/2006 | Basson et al. |
| 2006/0007189 A1 | 1/2006 | Gaines, III et al. |
| 2006/0017659 A1 | 1/2006 | Ogawa et al. |
| 2006/0040741 A1 | 2/2006 | Griswold et al. |
| 2006/0138210 A1 | 6/2006 | Parkos et al. |
| 2006/0155835 A1 | 7/2006 | Forutanpour |
| 2006/0171753 A1 | 8/2006 | Fessler et al. |
| 2006/0206717 A1 | 9/2006 | Holt et al. |
| 2006/0218643 A1 | 9/2006 | DeYoung |
| 2006/0228153 A1 | 10/2006 | Marowski et al. |
| 2006/0242259 A1 | 10/2006 | Vallabh et al. |
| 2006/0242559 A1 | 10/2006 | Krantz et al. |
| 2006/0255122 A1 | 11/2006 | Gilfix et al. |
| 2006/0255123 A1 | 11/2006 | Gilfix |
| 2006/0255141 A1 | 11/2006 | Kocis et al. |

| | | | |
|---|---|---|---|
| 2008/0019569 | A1 | 1/2008 | Rhoads et al. |
| 2008/0130896 | A1 | 6/2008 | Wernet et al. |

FOREIGN PATENT DOCUMENTS

| | | | |
|---|---|---|---|
| WO | WO 02/096014 | A1 | 11/2002 |
| WO | WO 03/106905 | A1 | 12/2003 |
| WO | WO 2005/043504 | A1 | 5/2005 |

OTHER PUBLICATIONS

"Ink-Jet Technology Provides Security Solutions"; Packaging Digest; bearing a date of Dec. 2005; 6 pages; located at http://www.packagingdigest.com/articles/200512/41.php; printed on Jun. 22, 2006.

Chalamala, Babu R.; Temple,, Dorota; "Big and Bendable"; IEEEE Spectrum; Sep. 2005; pp. 50-56; IEEE.

Chalamala, Babu R.; Temple, Dorota; "Big and Bendable"; Spectrum; pp. 1-10; IEEE; located at http://www.spectrum.ieee.org/print2121; printed on Sep. 14, 2005.

E-Ink; "E Ink and Toppan Announce Manufacturing and Marketing Agreement for Large Area Electronic Paper Displays"; pp. 1-2; located at http://www.eink.com/news/releases/pr76.html; bearing a date of 2002; printed on Dec. 22, 2004.

"Electrophoretic displays", IDTechEx; bearing dates of Jul. 28, 2004 and 2005; pp. 1-3; located at: http://222.idtechex.com/products/en/articles/00000053.asp; IDTechEx Ltd; Cambridge, UK; printed on May 20, 2005.

Espiner, Tom; "Nanocrystal sheds new light on future illumination"; pp. 1; located at http://www.zdnet.co.uk/hardware/emergingtech/0,39020357,39233182,00.htm.; ZDNet UK; bearing a date of Oct. 24, 2005; printed on Aug. 28, 2006.

"Lab dedicated to RFID technology"; p. 1-2; CNN.com; located at http://www.cnn.com/2005/TECH/08/30/rfid.research.ap/index.html; CNN.com; bearing a date of 2005; printed on Aug. 30, 2005.

Lynch, Martin; DIYE-Paper Kit—It's Real!; pp. 1-3; UK gizmodo.com; bearing a date of Oct. 20, 2005; located at http://uk.gizmodo.com/2005/10/20/diy_epaper_kit_its_real.html; printed on Aug. 28, 2006.

Mika, Niclas; "Electronic paper moves from sci-fi to marketplace"; pp. 1-2; located at http://news.yahoo.com/s/nm/20051104/tc_nm/column_pluggedin_dc; bearing a date of Nov. 4, 2005; Yahoo!Inc.; printed on Nov. 7, 2005.

Reimer, Jeremy; "E-paper: coming soon to a cereal box near you"; pp. 1; located at http://arstechnica.com/news.ars/post/20051215-5778.html; bearing a date of Dec. 15, 2005; printed on Aug. 28, 2006.

Seth, Anuj; "Data Encryption Page-Hash Functions"; pp. 1-2; located at http://www.anujseth.com/crypto/hash.php; printed on Jan. 18, 2005.

Weisman, Robyn, "Fujitsu Announces Bendable Color E-Paper"; pp. 1-2; Ziff Davis Media Inc.; located at http://www.publish.com/print_article2/0,1217,a=155977,00.asp; bearing a date of Jul. 14, 2005; printed on Feb. 6, 2006.

Peterson, Ivars; "Rethinking Ink, Printing the pages of an electronic book"; Science News Online and Science News; bearing a date of Jun. 20, 1998; total pp. 5; vol. 153; No. 25; Science Service.

U.S. Appl. No. 11/639,385, Jung et al.
U.S. Appl. No. 11/638,095, Jung et al.
U.S. Appl. No. 11/354,344, Jung et al.
U.S. Appl. No. 11/149,464, Jung et al.
U.S. Appl. No. 11/129,680, Jung et al.

Clarke, Peter; "Plastic Logic, E Ink, team for large area flexible display"; EETimes; pp. 1-1; located at: http://www.eet.com/article/showArticle.jhtml?articleId=54800435; CMP Media, LLC; bearing dates of 2003 and Dec. 6, 2004; printed on Dec. 22, 2004.

"Definition: Manipulation Detection Code (MDC)"; pp. 1-1; located at: http://www.atis.org/tg2k/_manipulation_detection_code.html; bearing a date of Feb. 28, 2001; printed on Jan. 18, 2005.

"RFID News Roundup"; pp. 1-1; located at: http://www.rfidjournal.com/article/articleprint/982/-1/1/; RFID Journal, Inc.; bearing dates of Jun. 7 and 11, 2004; printed on Dec. 22, 2004.

"Technology"; pp. 1-1; located at: http://www.eink.com/technology/index.html; E Ink Corporation; bearing a date of 2002; printed on Dec. 22, 2004.

"The Alchemist of paper"; The Economist; Apr. 16, 2005; p. 58.

"AbsoluteProof Data Integrity Service"; pp. 1-4; located at: http://www.surety.com/dataintegrity.php; Surety, Inc.; bearing a date of 2004; printed on Jan. 18, 2005.

Adams, Russ; "2-Dimensional Bar Code Page"; BarCode 1; bearing dates of 1995 and Mar. 15, 2005; pp. 1-10; Adams Communications; located at: http://www.adams1.com/pub/russadam/stack.html; printed on Apr. 25, 2005.

Becker, David; "Adobe adds bar codes to PDF forms"; CNet News.Com; pp. 1-2; CNET Networks, Inc.; bearing dates of Mar. 8, 2004 and 1995-2005; located at: http://news.com.com/2102-1012_3-5170996.html?tag=st.util.print; printed on May 4, 2005.

"Digital Signature Guidelines Tutorial"; American Bar Association Section of Science and Technology Information Security Committee; pp. 1-7; located at: http://www.abanet.org/abanet/common/print/printview.cfm?Ref=http://www.abanet.org/scitech/ec/isc/dsg-tutorial.html; The American Bar Association; printed on Jan. 20, 2005.

"Digital Signature Guidelines: Tutorial Footnotes"; pp. 1-5; located at: http://www.abanet.org/abanet/common/print/printview.cfm?Ref=http://www.abanet.org/scitech/es/isc/footnotes.html; The American Bar Association; printed Jan. 20, 2005.

"E Ink and Midori Mark Announce Manufacturing and Marketing Agreement for Retail Point-of-Purchase Displays"; pp. 1-2; located at: http://www.eink.com/news/releases/pr75.html; E Ink Corporation; bearing dates of 2002 and Oct. 5, 2004; printed on Dec. 22, 2004.

"Electronic Reusable Paper"; pp. 1-3; located at: http://www2.parc.com/dhl/projects/gyricon/; printed on Dec. 22, 2004.

Granmar, Marie; Cho, Adrian; "Electronic Paper: A Revolution About to Unfold?"; Science; vol. 308; May 6, 2005; pp. 785-786; Published by AAAS.

Kallender, Paul; "Epson developing e-paper, giant flexible screens: Electronic paper could be commercialized by the end of the decade"; pp. 1-2; Computerworld Inc.; located at: http://www.computerworld.com/printthis/2004/0,4814,98088,00.html; bearing dates of Dec. 7, 2004 and 2004; printed on Dec. 22, 2004.

Litterio, Francis; "The Mathematical Guts of RSA Encryption"; pp. 1-2; located at: http://world.std.com/~franl/crypto/rsa-guts.html; bearing dates of 1999-2001; printed on Jan. 19, 2005.

May, Tim; "Cryptology: Crypto Basics"; Cyphernomicon 5.4: Crypto Basics; pp. 1-10; located at: http://www.cyphernet.org/cyphernomicon/chapter5/5.4.html; printed on Jan. 18, 2005.

"Pico Systems, 1.0 Introduction"; pp. 1-2; located at: http://misspiggy.gsfc.nasa.gov/tva/pico/intro.htm; printed on Dec. 8, 2004.

"Portions from Application-Specific Integrated Circuits"; Sections 4.1—"The Antifuse" and 4.1.1—"The Metal-Metal Antifuse"; pp. 1-5; located at: http://www-ee.eng.hawaii.edu/~msmith/ASICs/HTML/Book2/CH04/CH04.1.htm; bearing a date of 1997; printed on Dec. 8, 2004.

Press, Jim; "Cryptography in Business"; pp. 1-3; located at: http://users.breathe.com/jpress/papers/Buscrypt.htm; printed on Jan. 18, 2005.

"RFID News Roundup"; pp. 1-1; located at: http://www.rfidjournal.com/article/articleprint/982/-1/1/; RFID Journal, Inc.; bearing dates of Jun. 7 and 11, 2004; printed on Dec. 22, 2004.

Rosencrance, Linda; "Taking Stock of E-paper"; pp. 1-4; Computerworld Inc.; located at: http://www.computerworld.com/printthis/2004/0,4814,95986,00.html; bearing a date of Sep. 20, 2004; printed on Dec. 22, 2004.

"Security Algorithm and Protocol Types"; pp. 1-2; located at: http://www.comptechdoc.org/independent/security/guide/secalgorithms.html; printed on Jan. 18, 2005.

"Security Functions"; pp. 1-2; located at: http://www.comptechdoc.org/independent/security/guide/secfunctions.html; printed on Jan. 18, 2005.

Stork, B.; "Cryptography: the art and science of keeping messages private"; pp. 1-4; located at: http://www.fh-augsburg.de/informatik/professoren/stork/faecher/cry...; printed on Jan. 18, 2005.

"T209 Module 5 glossary"; pp. 1-2; located at: http://homepage.ntlworld.com/sue.g.100/t209/mod5glossary.htm; printed on Jan. 18, 2005.

Taylor, Richard; "E-paper moving closer"; BBC News; Sep. 8, 2001; pp. 1-4; located at: http://news.bbc.co.uk/1/hi/sci/tech/1530678.stm; printed on May 9, 2005.

"The Alchemist of paper"; The Economist; Apr. 16, 2005; pp. 1.

Whittle, Robin; "Cryptography for encryption, digital signatures and authentication"; pp. 1-24; located at: http://members.ozemail.com.au/~firstpr/crypto/index.htm; bearing dates of Dec. 19, 1996, Mar. 30, 1997 and 1996; printed on Apr. 8, 2005.

* cited by examiner

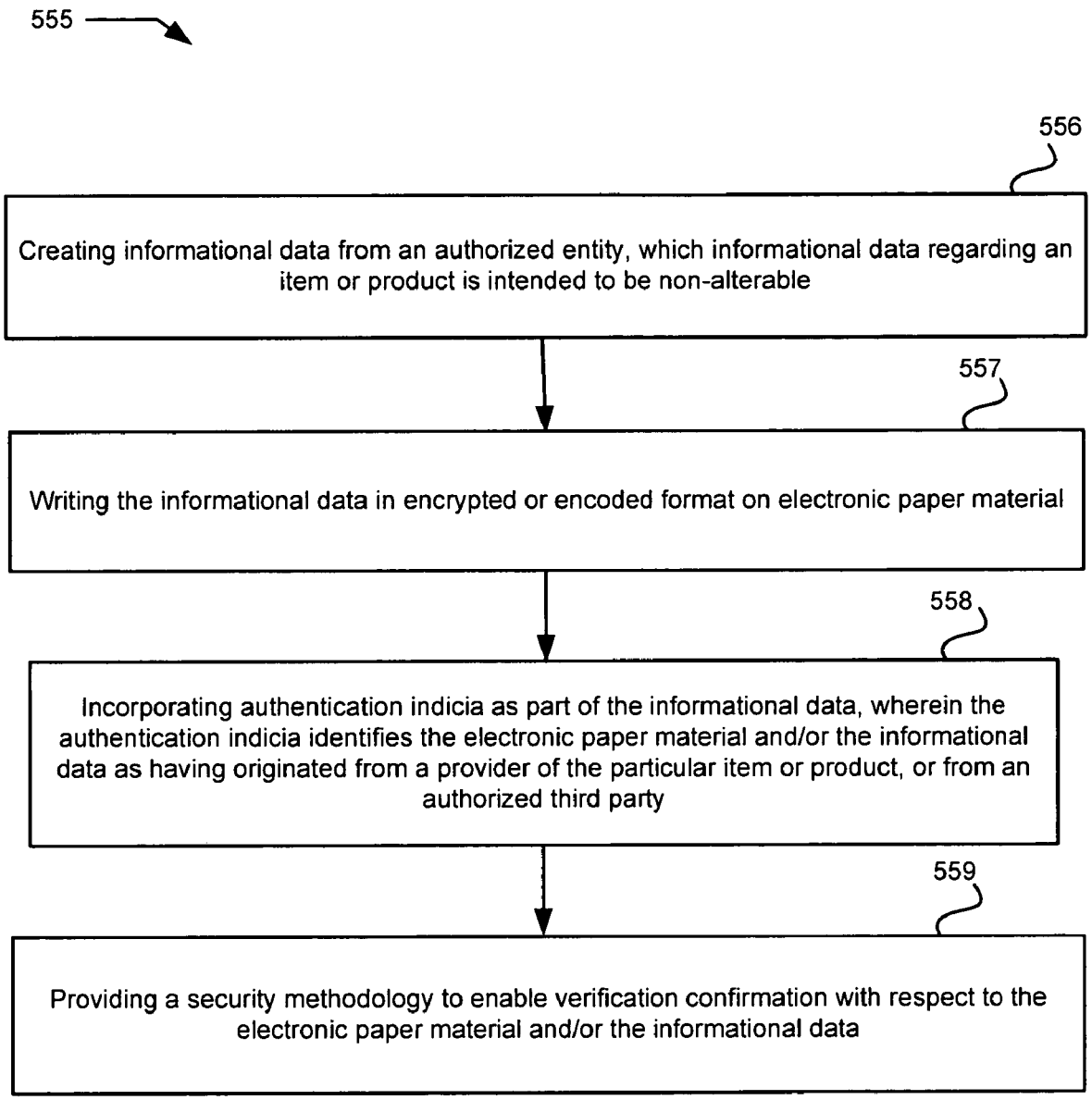

ALERT OPTIONS FOR ELECTRONIC-PAPER VERIFICATION

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the herein listed application(s) to the extent such subject matter is not inconsistent herewith; the present application also claims the earliest available effective filing date(s) from, and also incorporates by reference in its entirety all subject matter of any and all parent, grandparent, great-grandparent, etc. applications of the herein listed application(s) to the extent such subject matter is not inconsistent herewith. The United States Patent Office (USPTO) has published a notice to the effect that the USPTO's computer programs require that patent applicants reference both a serial number and indicate whether an application is a continuation or continuation in part. The present applicant entity has provided below a specific reference to the application(s) from which priority is being claimed as recited by statute. Applicant entity understands that the statute is unambiguous in its specific reference language and does not require either a serial number or any characterization such as "continuation" or "continuation-in-part." Notwithstanding the foregoing, applicant entity understands that the USPTO's computer programs have certain data entry requirements, and hence applicant entity is designating the present application as a continuation in part of its parent applications, but expressly points out that such designations are not to be construed in any way as any type of commentary and/or admission as to whether or not the present application contains any new matter in addition to the matter of its parent application(s).

For purposes of the USPTO extra-statutory requirements, the present application constitutes a continuation in part of the following currently co-pending commonly owned United States patent applications. The subject matter of the applications listed below are incorporated by reference in their entirety in the present application to the extent such subject matter is not inconsistent herewith.

Ser. No. 11/040,497 filed Jan. 20, 2005, entitled "Semi-Permanent Electronic Paper" naming Edward K. Y. Jung, Royce A. Levien, Mark A. Malamud, Kenneth B. Paley, John D. Rinaldo, Jr. and Clarence T. Tegreene as inventors.

Ser. No. 11/041,510 filed Jan. 21, 2005, entitled "Permanent Electronic Paper" naming Edward K. Y. Jung, Royce A. Levien, Mark A. Malamud, John D. Rinaldo, Jr. and Clarence T. Tegreene as inventors.

The present application is also related to the following commonly owned co-pending United States patent application filed on the same filing date as the present application. The subject matter of the application listed below is incorporated by reference in its entirety in the present application to the extent such subject matter is not inconsistent herewith.

Ser. No. 11/129,680 filed on May 12, 2005, entitled "Write Accessibility for Electronic Paper", naming Edward K. Y. Jung, Royce A. Levien, Mark A. Malamud, and John D. Rinaldo, Jr. as inventors.

TECHNICAL FIELD

This application relates generally to data on electronic paper (e-paper) material and e-paper documents.

BACKGROUND

Electronic paper (sometimes also called electric paper and e-paper) has begun to replace legacy paper as an information source. It has many of the attributes of paper. For example it is writable, reflective and stable. Electronic paper can also be configured as a flexible and thin sheet, like paper.

Electronic paper can be used as an information source to be written to by multiple entities. In some circumstances a reader of electronic paper will want to reliably understand that a specific entity has written a particular type of information, and/or that a particular region of the electronic paper has been written to by a particular entity, or has been written subject to the occurrence of a specific event.

SUMMARY

Methods and systems for indicating a verification status of an e-paper document related to an associated item, as disclosed herein, may take different forms. For example, some embodiments provide a sensor device for scanning encrypted or encoded information incorporated in the e-paper document, and a processor unit for performing a security validation on the encrypted or encoded information. An alert indicator on the e-paper document provides a first output responsive to the security validation performed by the processor unit.

Other aspects may be implemented in a method for providing verification status for an e-paper document associated with an item, wherein the method includes periodically monitoring encrypted or encoded data indicia on the e-paper document, and detecting an unauthorized access and/or unauthorized alteration to the encrypted or encoded data indicia. An automatic status output alert is generated based on a result obtained by the detecting.

Some implementations disclosed herein include a method for providing verification status for an e-paper document associated with an item. The method may include scanning encrypted or encoded data indicia on the e-paper document, and making a validation determination of whether the encrypted or encoded data indicia has been altered. The method may further provide a status output based on a result obtained by the validation determination.

Some embodiments are implemented in a computer program product with program instructions configured to perform a process that associates information in a computer system. An exemplary process may include scanning one or more types of encrypted or encoded data indicia on an e-paper document associated with an item or product or container or package, and making a validation determination of whether the encrypted or encoded data indicia has been altered. A status output is provided that is based on a result obtained by the validation determination.

The computer program product may also include a computer-readable signal-bearing media bearing the program instructions. The signal-bearing may include storage media and/or communication media.

Additional features, aspects and benefits will be understood by those skilled in the art from the following drawings and detailed description for various exemplary and preferred embodiments.

BRIEF DESCRIPTION OF THE FIGURES

FIG. 2 is a block diagram of an embodiment of an electronic paper showing a circuit to fix a region of the electronic paper from being further written to.

FIG. 31 is a high level flow chart showing an exemplary process for some embodiments.

DETAILED DESCRIPTION

Figure 1:
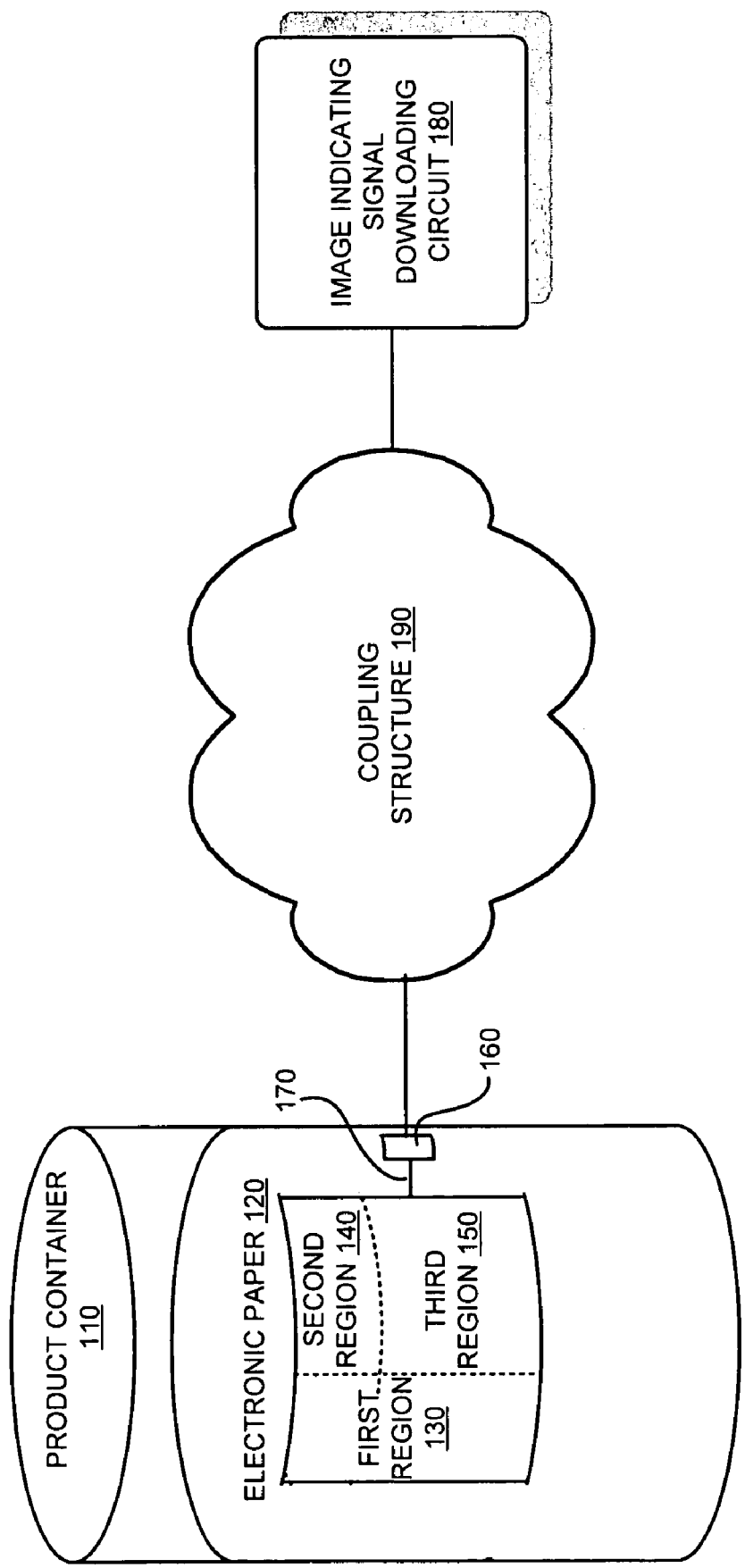
FIG. 1 is an embodiment of an illustrative product container having disposed thereon an electronic paper label and an embodiment of a coupled circuit disposed thereon to conditionally disenable an entity from writing to a specific region of the electronic paper.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use standard engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described aspects and drawings illustrate different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Those skilled in the art will recognize that some aspects of the embodiments disclosed herein can be implemented in standard integrated circuits, and also as one or more computer programs running on one or more computers, and also as one or more software programs running on one or more processors, and also as firmware, as well as virtually any combination thereof. It will be further understood that designing the circuitry and/or writing the code for the software and/or firmware could be accomplished by a person skilled in the art in light of the teachings and explanations of this disclosure.

Referring to FIG. 1, there is shown an embodiment of a product container 110. A product container 110 may illustratively contain a pharmaceutical to be provided to a consumer by a drugstore, a foodstuff, a manufactured product, or a communication medium such as a book or a DVD, and may illustratively be provided by a manufacturer, a wholesaler, a retailer, or a lending entity.

The product container 110 has disposed thereon an electronic paper 120. In an embodiment, the electronic paper 120 may be illustratively alternatively disposed on, or attached to, the product. The electronic paper 120 may function as a label, or some other indicator or source of information associated with the product. The electronic paper has regions illustratively portrayed as a first region 130, as a second region 140, and as a third region 150. In some embodiments, each region 130, 140, 150 may be written to by a specific entity. For instance, in an illustrative operation of the electronic paper 120, the first region 130 may be written to by a supplier of the product to a vendor, such as by a manufacturing entity or by a wholesaling entity. The second region 140 may be written to by a vendor of the product to a consumer, such as by a retailing entity or by a renting entity. The third region 150 may be written to by a consumer entity or by a purchaser of the product entity. In some embodiments, a region 130, 140, and/or 150 of the electronic paper 120 may be configured to have a visually distinct appearance from the remainder of the electronic paper. In some embodiments, the visually distinct appearance may be a background hue of a character written in a pixel of the region. In some embodiments, the visually distinct appearance may be a visual border of the region.

Some illustrative embodiments of electronic paper may include independently addressable and controllable pixels. In some embodiments, each pixel may include a pair of opposed electrodes disposed orthogonally to the surface of the paper. Each pixel may include an electrophoretic colored ink particle disposed in a region between the electrodes. When a field is applied between the electrodes, the ink particle in response migrates toward or away from an electrode, making the color of the ink particle visible or not visible to a reader observing the electronic paper. In some embodiments, each pixel may include a pair of opposed electrodes disposed orthogonally to the surface of the paper, each having an ink that includes a multicolored element. The ink may be configured to be rotatable in response to a field. Upon application of the field between the orthogonally disposed electrodes, the element will rotate according to the interaction of its dipole and the polarity of the field, to present a region to the surface of the electronic paper visible to a reader observing the electronic paper. In some embodiments, the electronic paper has ambient light behavior, being easier to see the brighter the ambient light. Moreover, in some embodiments the ink is stable in each pixel state so that the electronic paper consumes substantially little or no power in maintaining a pixel state.

In some embodiments of operation of the electronic paper 120, in an embodiment in which illustratively the electronic paper 120 is a label on a product container 110 for containing a pharmaceutical, the first region 130 may be for writing by the manufacturing entity and may contain such information as the potency of the enclosed pharmaceutical and the contraindications associated with the pharmaceutical. The second region 140 may be for writing by a drugstore entity, and may contain such information as the dosage and the usage instructions associated with the pharmaceutical. And the third region 150 may be for writing by a patient entity, and may contain such information as the times at which the patient has consumed or is scheduled to consume the pharmaceutical. Thus, in some embodiments each region may be exclusively written to by a specific entity.

In some embodiments, the electronic paper 120 may be configured to receive a signal indicating an image to be written on the first region 130, the second region 140, and/or the third region 150; and to cause the indicated image to be written on the electronic paper 120. The signal is termed herein an image indicating signal.

In some embodiments, the image indicating signal may be illustratively formatted to indicate an image corresponding to the respective pixels of the electronic paper 120, such as a pixel map, or may be formatted according to some other format, such as a page description language representation format, or a picture editing application representation format (such as a graphics application format, an image editing application format, a painting application format, an illustration application format, a drafting application format, a CAD application format, a diagramming application format, or the like). In some embodiments, the electronic paper 120 may have an associated circuit to decode the image indicating signal, and to address a control signal to each pixel indicated by the image indicating signal.

In some embodiments, the electronic paper 120 may include pixel address lines, each able to couple to an external coupling structure 170. The external coupling structure 170 may be configured to transmit the image indicating signal to the electronic paper 120 by communicating with each coupled address line. In this embodiment, the image indicating signal may include a separate signal for each pixel, transmitted to the proper address lines by the external coupling structure 170.

Illustratively, in some embodiments, coupled to the electronic paper 120 may be a circuit 160 configured to control the writing of an image to the illustrative regions 130, 140, and 150 of the electronic paper 120. In some embodiments, at least a portion of the circuit 160 may be disposed on, without, and/or within the electronic paper 120. In some embodiments, the circuit 160 may be disposed on or within the product container 110, or other structure to which the electronic paper 120 is attached. The circuit 160 may be coupled to the electronic paper 120 across the external coupling structure 170. The circuit 160 may be configured to receive an image indicating signal from an image indicating signal downloading circuit 180 across another coupling structure 190. The coupling structure 190 in some embodiments includes illustratively a bus, a wireless connection, and/or a network for transmitting the image indicating signal from the image indicating signal downloading circuit 180 to the circuit 160, or to the electronic paper 120.

The circuit 160, in some embodiments, may be configured to control the writing of the image by an entity to at least one of the regions 130, 140, and 150, by conditionally disenabling the entity from writing to the region. As used herein, the term disenabling may include preventing or making something unable to operate; and may include disabling, not generating, and the like. In some embodiments, the circuit 160 may be configured to disenable an entity from writing to a region of the electronic paper 120 by not transmitting a received image indication (from the image indicating signal downloading circuit 180) to the electronic paper 120. Some embodiments of the circuit 160 and the actions it may be configured to perform are described below, as well as with reference to FIGS. 5, 6, 7A and 7B, and 8 below.

An example of conditional disenabling is to disenable some or all entities from writing to at least one specific region such that one or more specific entities may write to the specific region. For instance, as described above, each region may to be written to by a defined specific entity. Illustratively, the first region 130 may be for writing to by a defined manufacturing entity, the second region 140 may be for writing to by a defined drugstore entity, and the third region 150 may be for writing to by a patient entity, and other entities may be disenabled from writing to the regions. For example, a manufacturing entity may be disenabled from writing to the second region 140 and the third region 150, the drugstore entity may be disenabled from writing to the first region 130 and the third region 150, and the patient entity may be disenabled from writing to the first region 130 and the second region 140. As another example of conditional disenabling, a specific region may be disenabled from being written to by specific entities (or equivalently, a specific entity may be disenabled from writing to a specific region) subject to an occurrence of an event, such as an event defined as a region having been written to a specific number of times. In some such embodiments, and other embodiments that depend upon a region of the electronic paper and/or an entity endeavoring to write to the region, the circuit 160 may be configured to read from the received image indicating signal an identity of the region to be written to and/or an identity of the entity endeavoring to write to the region, and to transmit an indication of the image to the electronic paper 120 for entities not disenabled from writing to a region. In another implementation, the circuit 160 may be configurable to control the substantially permanent writing to a specific region 130, 140, and/or 150 of the electronic paper 120 by disenabling an entity from writing to a region subject to the occurrence of the region having been written to a prescribed number of times, such as one time.

Figure 2:
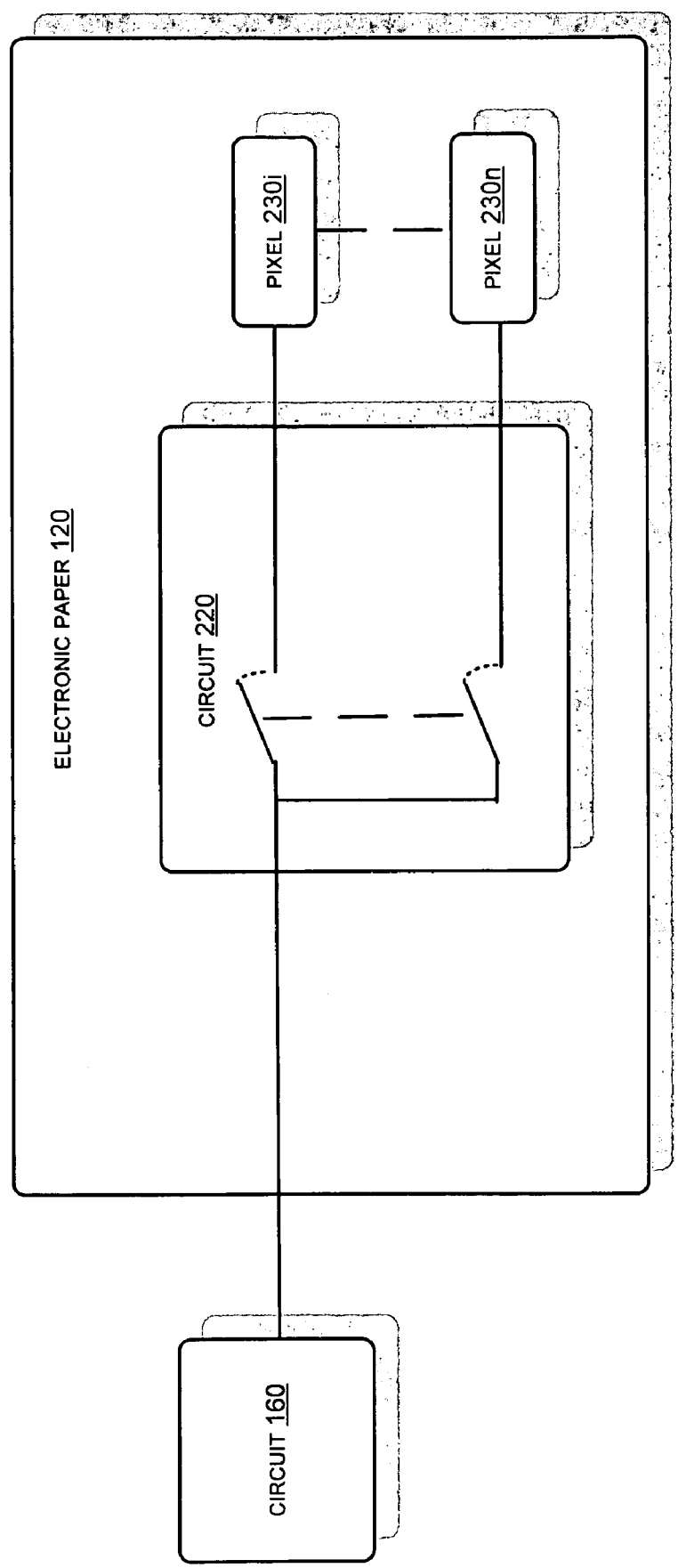

In some embodiments, the circuit 160 may be configured to substantially permanently write a specific region of the electronic paper 120. For example, the circuit 160 may be configured to fix an image in all or part of the region of the electronic paper 120. Referring to FIG. 2, in an embodiment, the circuit 160 may be configured to generate and send to the electronic paper 120, or a circuit 220 associated with the electronic paper 120, a signal indicating the pixels 230$i$-230$n$ ($i$=1 to n) of the electronic paper 120 to be fixed. In some embodiments, the circuit 160 may be configured to generate the signal based on an identity of the region, and/or on an identity of an entity endeavoring to write on the region as described above with reference to FIG. 1. In some embodiments, the electronic paper 120 may include a circuit 220 configured to fix the electronic paper by fixing pixels of a specified region of the electronic paper. Those skilled in the art will appreciate that although circuits 160 and 220 are shown separated herein for sake of clarity, and circuit 220 is shown as part of electronic paper 120, in other embodiments circuit 160 and circuit 220 may be combined in one overall circuit which can be external from or internal to electronic paper 120 (e.g., associated with electronic paper 120). In an illustrative implementation, an individual pixel of an electronic paper 120 is fixed by controlling the transmission of an image to the pixel. The circuit 220 may be configured to fix the region of the electronic paper 120 from being written to by illustratively opening the transmission path to the pixels 230$i$-230$n$ subsequent to information being written thereto (e.g., by circuit 160), so that the information previously written to the pixels 230$i$-230$n$ may be regarded as substantially permanent. As a specific example of the foregoing, one or more voltages to be provided to one or more of the pixels 230$i$-230$n$ would be disabled from being received by one or more of the pixels 230$i$-230$n$.

Exemplary implementations of substantially permanently writing at least one region of electronic paper are described herein in the context of an illustrative pixel addressing scheme. In an embodiment, information written to at least one pixel may be rendered substantially permanent by opening an input circuit of the pixel. In another illustrative embodiment, information written to at least one pixel may be rendered substantially permanent by closing a circuit to divert a signal for modifying the pixel. And in another embodiment, information written to at least one pixel may be rendered substantially permanent by activating a switched input of the pixel.

Illustratively in an implementation of substantially permanently writing at least one region of electronic paper, a pixel may be addressed by an active matrix addressing scheme in which a separately addressed electrode is provided for each pixel. One implementation in which the pixel may be fixed includes a fuse to control transmission to the electrode, so if the fuse opens, a transmission to the electrode may be disabled. Then by controlling the current to the fuse to exceed the fuse transmission limit, the fuse is caused to open and thus the content of the pixel is therefore rendered substantially permanent. Similarly in an implementation, an antifuse may be configured so that if the antifuse closes, a transmission to the electrode will bypass the electrode, therefore disabling the transmission from affecting the electrode voltage, and the thus content of the pixel is therefore rendered substantially permanent. Those skilled in the art will appreciate that this single pixel example may be replicated such that substantially any desired pattern displayed by a collection of like configured and/or controlled pixels may thus be made substantially permanent. Moreover, illustratively a pixel may be addressed by a passive matrix addressing scheme in which two sets of intersecting conductors, one designated a row conductor and one designated a column conductor, together uniquely supply a voltage to a given electrode of the pixel. The supplied voltage is the sum of the voltage of the row and the column conductors. The electrode is configured to retain the applied voltage. Each row or column voltage is below the threshold to cause an ink to respond to the field generated by the electrode of the pixel. However, the sum of the row and column voltages exceeds the ink response threshold. This is sometimes called a threshold response behavior. One implementation in which the pixel may be fixed includes a fuse (or the antifuse) to control transmission to the electrode, so if the fuse opens (or the antifuse closes), a transmission from the intersecting conductors to the electrode may be disabled. Then by controlling the current to the fuse (or antifuse) to exceed the fuse (or the antifuse) transmission limit, the fuse is caused to open (or the antifuse is caused to close) and the pixel is therefore fixed from being written to. Those skilled in the art will appreciate that this single pixel example may be replicated such that substantially any desired pattern displayed by a collection of like configured and/or controlled pixels may thus be made substantially permanent. Moreover, illustratively a pixel may be addressed by a matrix addressing scheme in which an electrically non-linear element is operationally disposed between a supply voltage and a pixel electrode to switch a voltage onto the electrode. In this schema, the switch may illustratively be disabled from further switching so that the electrode may retain its supplied voltage. This may be affected by a variety of schema, depending upon the specific characteristics of the switch. Illustratively, if the switch is embodied as a transistor, the control current of the transistor may be controlled to disable the transistor from supplying the electrode with a switched voltage.

As has been described elsewhere herein, electronic paper itself has data retention characteristics which allow information written thereto be to rendered substantially permanent by effectively disabling further input to pixels of the electronic paper once the data to be made permanent has been written. In some contemplated implementations, the information may be rendered yet more permanent by circuit 160 and or 220 (or various combinations or permutations thereof within the ambit of those skilled in the art) configurable to fix an image within at least a portion of the first region 130 by being configurable to write an image within at least the portion of the first region and to thereafter establish one or more assisted non-volatile signal levels to the pixels of the portion of the first region 130. In some implementations, the assisted non-volatile signals are created by applying related art signal maintenance techniques to one or more of the electronic paper pixels into which information has been loaded (e.g., by applying capacitive storage and/or flash-memory like techniques to the pixels), and thereafter effectively rendering further input to the loaded pixels effectively inoperative. Illustrative implementations by which further input to the loaded pixels is rendered effectively inoperative include fusing circuitry, anti-fusing circuitry, lasing circuitry, an electro-mechanical switch, and/or an electromechanical cutting mechanism, but those skilled in the art will recognize that other functionally interchangeable related art techniques are also applicable. Moreover, in an embodiment the circuitry (e.g., circuits analogous to circuit 160 and/or 220 as described elsewhere herein) may include write-once circuitry configured to permit one image to be written to the portion of the first region 130. In an embodiment, this includes circuitry configured to make static at least a portion of the first region 130. In an embodiment, this circuitry may include fusing circuitry, lasing circuitry, an electro-mechanical switch, an electromechanical lead cutting mechanism, and/or circuitry to establish a non-volatile signal level. Both assisted and non-assisted non-volatile signal levels as described herein are contemplated.

Figure 3:
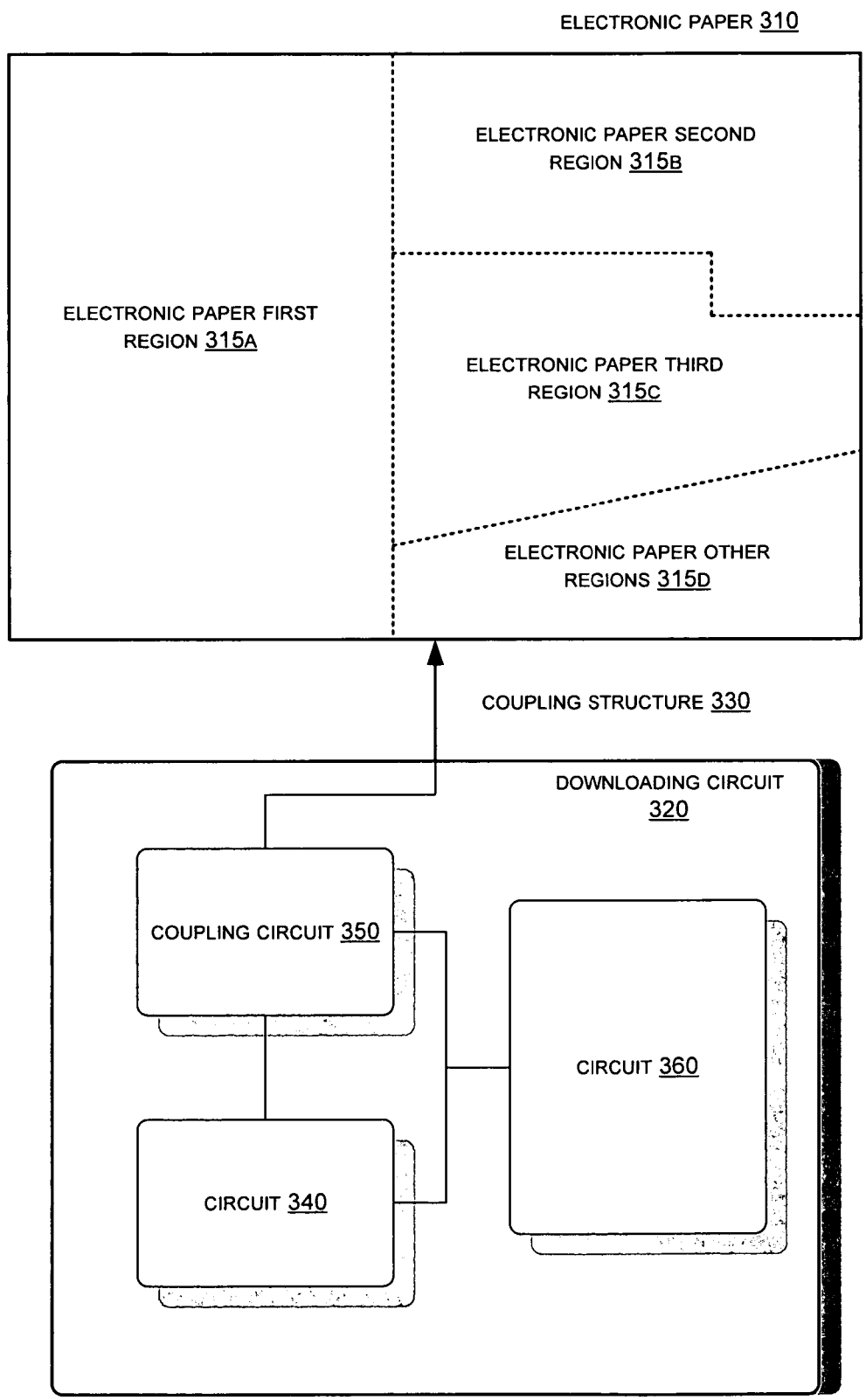
FIG. 3 is a top view diagram of an embodiment of an electronic paper partitioned into illustrative regions, coupled to a block diagram of an embodiment of a downloading circuit.

Referring now to FIG. 3, in an embodiment, an illustrative electronic paper 310 includes a finite quantity of defined regions for portraying an image, 315A through 315XX, here illustratively portrayed as a first region 315A, as a second region 315B, and as a third region 315C, and illustratively other regions 315D. In an embodiment, a region 315A, 315B, 315C and/or 315D of the electronic paper 310 is configured to have a visually distinct appearance from the remainder of the electronic paper. In an embodiment, the visually distinct appearance is a background hue of a character written in a pixel of the region. In an embodiment, the visually distinct appearance is a visual border of the region.

The electronic paper 310 is configured to receive a signal indicating an image to be written on the first region 315A, an image to be written on the second region 315B, and/or an image to be written on the third region 315C of the electronic paper 310, termed an image indicating signal; and to cause the indicated image to be written on the electronic paper 310.

In an embodiment, an illustrative downloading circuit 320 is configured to download the image indicating signal to the electronic paper 310 for an image to be written on the first region 315A, the second region 315B, and/or the third region 315C of the electronic paper 310. The downloading circuit 320 may be coupled to the electronic paper 310 by way of a coupling structure 330. The downloading circuit 320 is to download the image indicating signal across the coupling structure 330 to the electronic paper 310. In embodiments, the coupling structure 330 may comprise a wireless connection, a bus connection, and/or a network as well as other structures known in this art to transmit an image indicating signal from the downloading circuit 320 to the electronic paper 310. In an embodiment, the downloading circuit 320 includes a circuit 340 to prepare an image indicating signal. In an embodiment, the downloading circuit 320 further includes a coupling circuit 350 to couple the circuit 340 to the electronic paper 310, by way of the coupling structure 330 in a transmitting relationship from the downloading circuit 320 to the coupling structure 330.

In an embodiment, the downloading circuit 320 includes a circuit 360 configured to control the writing of an image to specified regions 315A, 315B, and 315C of the electronic paper 310. In an implementation, the downloading circuit 360 may be configured to control the writing of the image by an entity to the specified regions, by conditionally disenabling the entity from writing to a specific region. In an implementation, the conditional disenabling depends upon an identity of the region, and/or an identity of the entity. In an implementation, the downloading circuit 360 is configurable to control the substantially permanent writing to a specific region 315A, 315B, and/or 315C of the electronic paper 310.

In an embodiment, the circuit 360 controls disenabling writing an image to the specified regions, and substantially making permanent an image written to a region, by disenabling the downloading circuit 320 from transmitting the image indicating signal for an image to be written on the regions 315A, 315B, and/or 315C. The circuit 360 may be configured to disenable the downloading circuit 320 from transmitting the image indicating signal for these regions, depending upon criteria such as the entity that is endeavoring to write on the region, the occurrence of an event, and the identity of the region 315A, 315B, 315C to which an entity is endeavoring to write. Stated in an analogous way, the circuit 360 may be configured to disenable the downloading circuit 320 from transmitting the image indicating signal for an entity endeavoring to write on a region depending upon criteria such as an identity of the entity and an identity of the region, and an occurrence of an event. An embodiment of the circuit 360 and the actions it is configured to perform are furthermore presently described with reference to FIGS. 6, 7, 8A and 8B, and 9.

In an implementation, the downloading circuit 320 and/or circuit 360 may include a user interface (not shown) to receive inputs from an entity, the inputs indicating an image to be written on the first region 315A, the second region 315B, and/or the third region 315C, and/or an identification of the identity of the entity. In an implementation, the circuit 360 may control the writing of the image to the regions 315A, 315B, and 315C by algorithmically determining whether the downloading circuit 320 is to include the image in an image indicating signal to be downloaded to the electronic paper 310. If the downloading circuit 320 is to include the image in the image indicating signal, the circuit 360 may be configured to transmit an indication of the request by the entity to the circuit 340, so that the downloading circuit 320 can download an image indicating signal for the image(s). In an implementation, if the downloading circuit 320 is not to include the image in the image indicating signal, the circuit 360 may be configured to not transmit an indication of the request by the entity to the circuit 340, or another circuit in the downloading circuit 320. In another implementation, the circuit 360 may be configured to transmit an indication that the downloading circuit 320 is to not download an indication of the image to the circuit 340 or to another circuit in the downloading circuit 320. In this implementation, the downloading circuit 320 may include a user interface (not shown) to receive inputs indicating an image to be written on the first region 315A, the second region 315B, and/or the third region 315C, and/or an identification of the entity requesting the image be downloaded by the downloading circuit 320 to the electronic paper 310, depending upon a receipt of a disenabling signal from the circuit 360.

Figure 4:
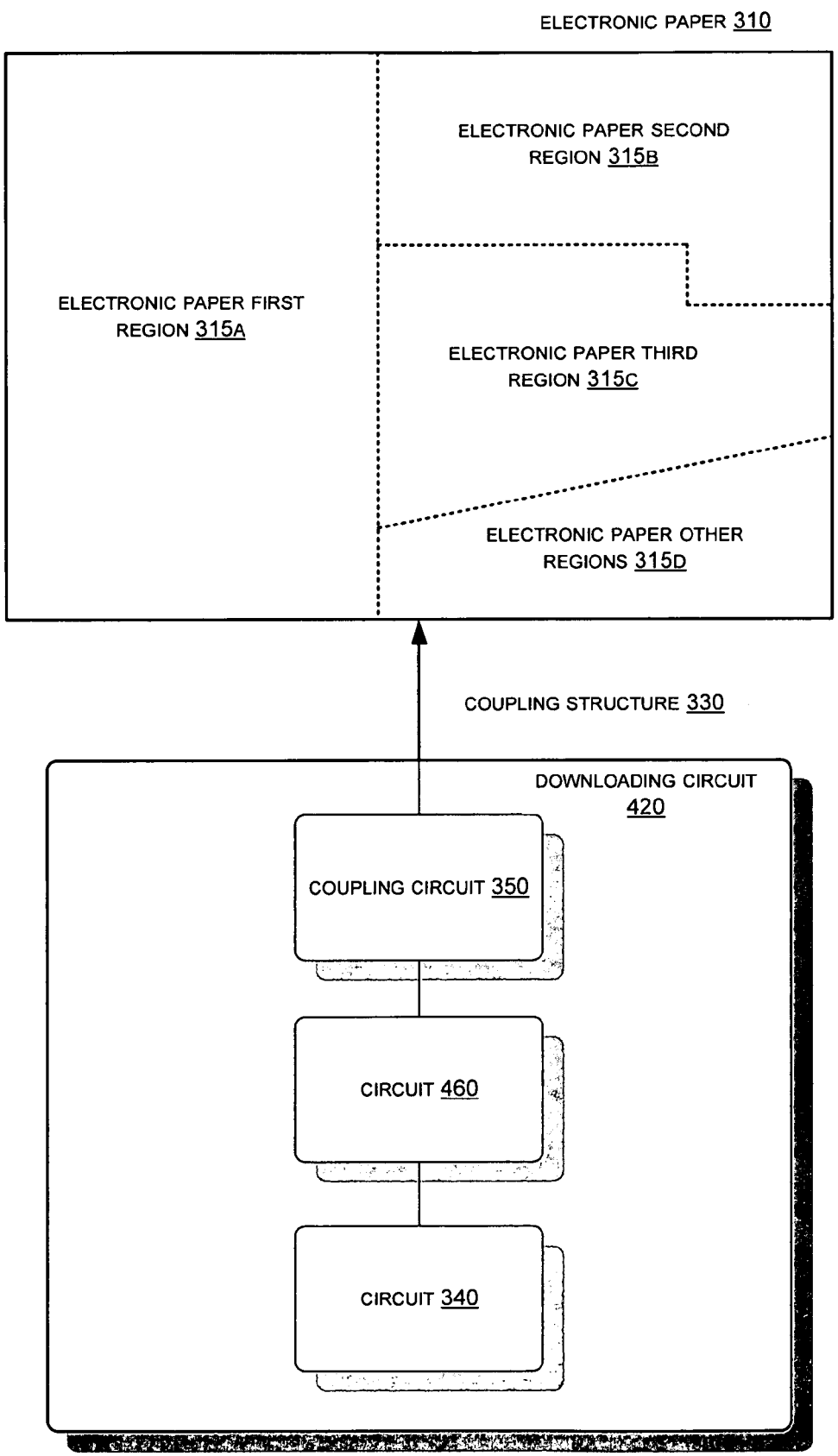
FIG. 4 is a top view diagram of an embodiment of an electronic paper partitioned into illustrative regions, coupled to a block diagram of another embodiment of a downloading circuit
Figure 5:
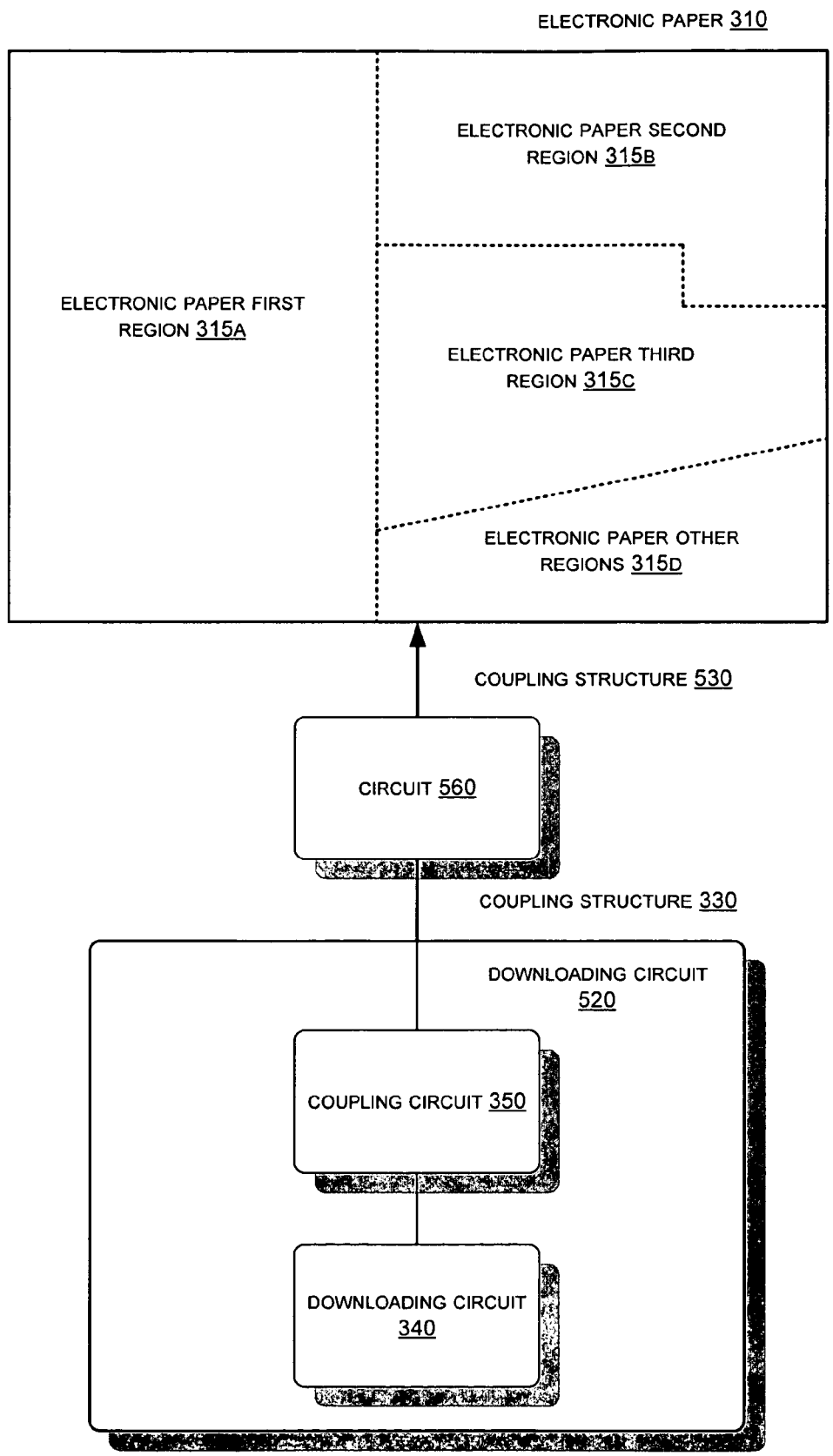
FIG. 5 is a top view diagram of an embodiment of an electronic paper partitioned into illustrative regions, coupled to a block diagram of an embodiment of a circuit to conditionally disenable an entity from writing to a specific region of an electronic paper.

In another embodiment, the circuit 360, the circuit 340, or another circuit of the downloading circuit 320 may be configured to generate and to send to the electronic paper 310, or a circuit within the electronic paper 310, a signal indicating the pixels of the electronic paper 310 to be fixed from being further written to, as described above with reference to FIGS. 1 and 2. In an embodiment, the circuit is configured to fix the electronic paper 310 based on an identity of the region, and/or on an identity of an entity endeavoring to write on the region Referring to FIG. 4, in another illustrative embodiment, there is portrayed a downloading circuit 420 to download an image indicating signal to the electronic paper 310 across the coupling structure 330. The downloading circuit 420 includes the circuit 340, the coupling circuit 350, and a circuit 460. The circuit 460 is coupled to the circuit 340 in an image indicating signal receiving relationship, and to the coupling circuit 350 in an image indicating signal transmitting relationship.

The circuit 460 is configured to control the writing of an image to specified regions 315A, 315B, and 315C of the electronic paper 310. In an implementation, the circuit 460 may be configured to control the writing of the image by an entity to the specified regions, by conditionally disenabling the entity from writing to a specific region. In an implementation, the conditional disenabling may depend upon an identity of the region, the occurrence of an event, and/or an identity of the entity. In an implementation, the circuit 460 is configurable to control the substantially permanent writing to a specific region 315A, 315B, and/or 315C of the electronic paper 310.

In an embodiment, the circuit 460 controls disenabling writing an image to a region, and for substantially making permanent an image written to a region, by disenabling the circuit 420 from transmitting the image indicating signal for an image to be written on the regions 315A, 315B, and/or 315C. The circuit 460 may be configured to disenable the circuit 420 from transmitting the image indicating signal for these regions, depending upon criteria such as the entity that is endeavoring to write on the region, and the identity of the region 315A, 315B, 315C to which an entity is endeavoring to write, and an occurrence of an event. Stated in an analogous way, the circuit 460 may be configured to disenable the downloading circuit 320 from transmitting the image indicating signal for an entity endeavoring to write on a region depending upon criteria such as an identity of the entity, an identity of the region, and/or an occurrence of an event. An embodiment of the circuit 460 and the actions it is configured to perform are furthermore presently described with reference to FIGS. 6, 7, 8A and 8B, and 9.

The circuit 460 may be configured to receive an image indicating signal from the circuit 340. The circuit 460 may be configured to selectively download the received image indicating signal to the coupling circuit 350 for transmission to the electronic paper 310, algorithmically depending upon the region to which the image is to be written, the entity requesting that the image be written, and/or an occurrence of an event. In an implementation, the downloading circuit 420 includes a user interface (not shown) to receive inputs indicating an entity requesting that an image be written on the first region 315A, the second region 315B, and/or the third region 315C, as well as an identity of the region, and/or an identity of the requesting entity.

In an embodiment, the circuit 460 may be configured to fix the electronic paper 310 from writing onto the electronic paper 310, or onto a specific region 315A, 315B, and/or 315C of the electronic paper 310, an image downloaded to the electronic paper 310. The circuit 460, or another circuit of the downloading circuit 420, may be configured to generate and to send to the electronic paper 310, or a circuit within the electronic paper 310, a signal indicating the pixels of the electronic paper 310 to be fixed from being further written to, as described above with reference to FIGS. 1 and 2. In an embodiment, the circuit is configured to fix the electronic paper 310 based on an identity of the region, and/or on an identity of an entity endeavoring to write on the region Referring now to FIG. 5, in an embodiment, a downloading circuit 520, in operation of downloading an image indicating signal for an image to be portrayed on the first region 315A, on the second region 315B, and/or on the third region 315C of the electronic paper 310, is coupled to the electronic paper 310 by way of the sequential coupling of the coupling structure 330, a circuit 560, and a coupling structure 530. The downloading circuit 520 is configured to download an image indicating signal across the coupling structure 330 to the electronic paper 310. In embodiments, the coupling structure 530 may comprise a wireless connection, a bus connection, and/or a network, as well as other structures known in this art to transmit an image indicating signal from a circuit to an electronic paper 310. In an embodiment, the downloading circuit 520 is disposed on, along, or within the electronic paper 310, and is not coupled to the electronic paper 310 by the coupling structure 530. In an embodiment, the downloading circuit 520 includes the coupling circuit 350 to prepare an image indicating signal, and the coupling circuit 350 to couple the downloading circuit 340 to the electronic paper 310 by way of the coupling structure 330. An illustrative circuit 560 is coupled to the coupling structure 330 in a signal receiving relationship, and coupled to the coupling structure 530 in a signal transmitting relationship, so that an image indicating signal transmitted by the downloading circuit 520 is received by the circuit 560, and selectively transmitted by the circuit 560 to the electronic paper 310.

The circuit 560 is configured to control the writing of an image to specified regions 315A, 315B, and 315C of the electronic paper 310. In an implementation, the circuit 560 may be configured to control the writing of the image by an entity to the specified regions, by conditionally disabling the entity from writing to a specific region. In an implementation, the conditional disenabling may depend upon an identity of the region, an occurrence of an event, and/or an identity of the entity. In an implementation, the circuit 560 may be configurable to control the substantially permanent writing to a specific region 315A, 315B, and/or 315C of the electronic paper 310. The circuit 560 is configured to disenable the downloading circuit 520 from transmitting the image indicating signal for these regions, depending upon criteria such as the entity that is endeavoring to write on the region, the identity of the region 315A, 315B, 315C to which an entity is endeavoring to write, and an occurrence of an event.

In an embodiment, the circuit 560 is configured to fix the electronic paper 310 from writing onto the electronic paper 310, or onto a specific region 315A, 315B, and/or 315C of the electronic paper 310, an image downloaded to the electronic paper 310. The circuit 560, or another circuit of the downloading circuit 520, may be configured to generate and to send to the electronic paper 310, or a circuit within the electronic paper 310, a signal indicating the pixels of the electronic paper 310 to be fixed from being further written to, as described above with reference to FIGS. 1 and 2. In an embodiment, the circuit (not shown) is configured to fix the electronic paper 310 based on an identity of the region, and/or on an identity of an entity endeavoring to write on the region.

An embodiment of the circuit 560 and the actions it is configured to perform are furthermore presently described with reference to FIGS. 6, 7, 8A and 8B, and 9.

Moreover, in an embodiment, the circuit 560 includes a first circuit configured to fix an image within at least a portion of the first region 315A by being configurable to write an image within at least the portion of the first region and to substantially disenable further input to the at least portion of the first region 130 and/or further writing to the pixels thereof. In embodiments, the first circuit illustratively includes circuitry configurable to establish a non-volatile signal level to the pixels of the portion of the first region 315A. Illustrative implementations include fusing circuitry, anti-fusing circuitry, lasing circuitry, an electro-mechanical switch, and/or an electromechanical cutting mechanism to disenable writing to the specified portion of the first region 315A. Moreover, in an embodiment the first circuit may include write-once circuitry configured to permit only one image to be written to the portion of the first region 315A. In an embodiment, this includes circuitry configured to make static the at least portion of the first region 315A. In an embodiment, this circuitry may include fusing circuitry, lasing circuitry, an electromechanical switch, an electromechanical lead cutting mechanism, and/or circuitry to establish a non-volatile signal level.

The circuit 560 may be configured to disenable the image from being written on the regions 315A, 315B, and/or 315C by selectively transmitting a received image indicating signal. The circuit 560 may be configured to selectively transmit the image indicating signal depending upon criteria such as the entity that is endeavoring to write on the regions, the identity of the region 315A, 315B, 315C to which an entity is endeavoring to download an image, and the occurrence of an event.

Figure 6:
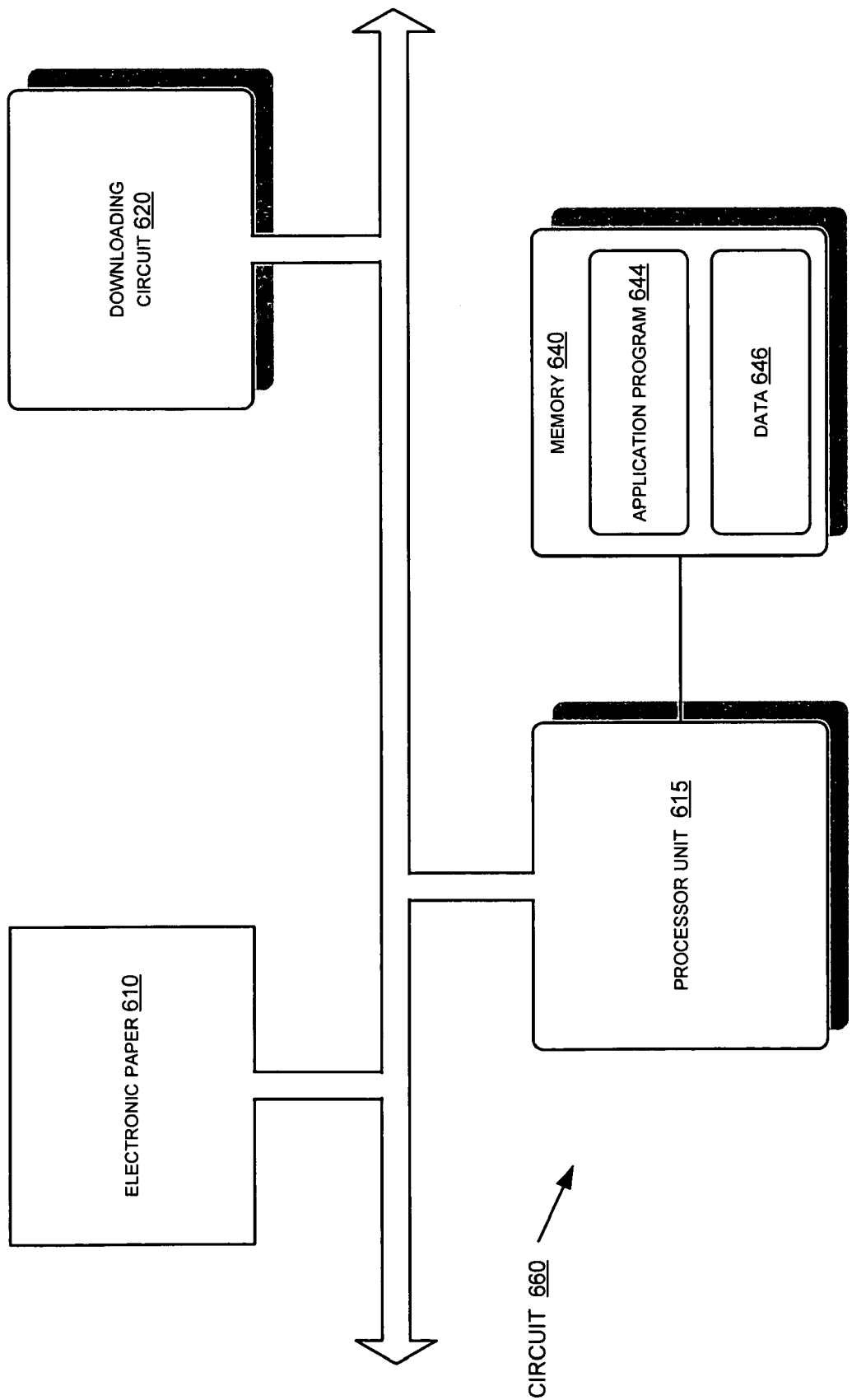
FIG. 6 is a block diagram of an embodiment of a circuit to control the writing of an image on regions of an electronic paper.

FIG. 6 portrays an illustrative circuit 660 configured to control the writing of an image to specific regions of an electronic paper 610. Exemplary embodiments of such a circuit 660 have been described as the circuit 160 with reference to FIG. 1, as the circuit 360 with reference to FIG. 3, as the circuit 460 with reference to FIG. 4, and as the circuit 560 with reference to FIG. 5. The circuit 660 is configured to control the writing of an image to specific regions of the electronic paper 610 by conditionally disenabling an entity from writing to a region of the electronic paper 610.

The portrayed circuit 660 may be implemented as a programmed computer, configured to respond to an application program, and having a port to couple the computer to the electronic paper 610 (in an embodiment) and to an image indicating signal downloading circuit 620 (in an embodiment). Exemplary embodiments of an image indicating signal downloading circuit have been described as the image indicating signal downloading circuit 180 with reference to FIG. 1, as the downloading circuit 320 with reference to FIG. 3, as the circuit 420 with reference to FIG. 4, and as the downloading circuit 520 with reference to FIG. 5. It is specifically contemplated that other embodiments of the circuit 660 may be implemented in whole or in part by finite state circuitry.

Referring to FIG. 6, the circuit 660 includes a memory 640, and a processor unit 615. The memory 640 is to store an application program 644, and data 646 for use by the circuit 660, or to be generated by the processor unit 615 in executing the application program 644. The application program 644 describes an algorithm to be executed by the circuit 660 in performing the described functions of the circuit 660. Embodiments of the algorithm are illustratively described below with reference to FIGS. 7, 8A and 8B, and 9. The memory unit 640 in an embodiment includes a volatile RAM memory portion, as well as a non-volatile memory portion for storing the application program 644. Though the application program 644 may be stored in the non-volatile memory portion, the application program 644 may be executed from the volatile RAM portion after being written into the volatile RAM portion.

The processor unit 615 includes one or more processors, each capable of generally executing program instructions on data and specifically executing the application program 644.

In an embodiment, the processor unit 615 and the memory 640, are incorporated in a general purpose computer system, such as in a server system, a personal computer, a main frame system, a mid-range system, and a client system. In another embodiment, the processor unit 615 and the memory 640 compose a stand alone dedicated computer system such as an embedded computer system and a point-of-sale system.

FIGS. 7, 8A-8B, and 9 describe respective embodiments of a method 700, 800, and 900 to use electronic paper. The methods 700, 800, and 900 also describe an algorithm embodied in the application program 644. In an embodiment, in support of the method 700, 800, and 900, a flag or other device may be maintained to indicate whether a specific entity has written to a specific region of the electronic paper, so that knowledge of whether an entity has written to a specified region is obtained by reading the flag. Moreover, in an embodiment the identity of a specified entity, and/or a region may be determined and maintained by way of an input from a user interface. Furthermore, in an embodiment, the identity of a specified entity and/or region may be downloaded to the circuit 660 (or other circuit of the downloading circuit 620). In an embodiment in which an image indicating signal is downloaded to the circuit 660, the image indicating signal may include a field to indicate the identity of the entity endeavoring to write to the electronic paper, and the circuit 660 may be configured to read the field.

Figure 7:
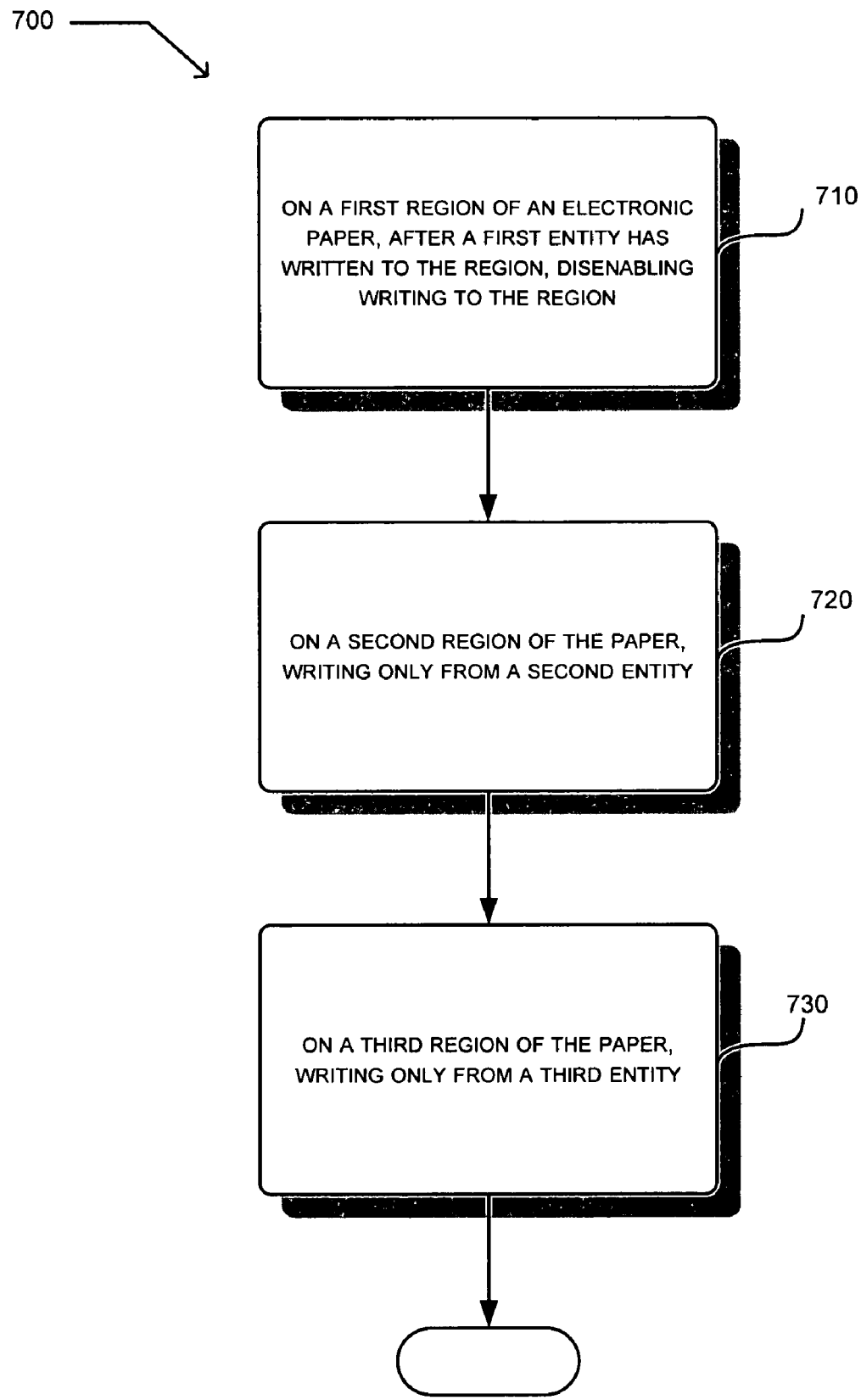
FIG. 7 is a flow chart of an embodiment of a method of using electronic paper and the actions of a circuit configured to control the writing of an image on a region of the electronic paper.

Referring now to FIG. 7, an embodiment of method 700 to conditionally disenable an entity from writing to a specific region of an electronic paper is portrayed. In the method 700, the disenabling depends upon an identity of the region and/or an identity of the entity. The method includes in block 710, disenabling writing to a first region of an electronic paper after a first entity has written an image on the region. An embodiment of the method includes an action of determining whether the first entity has already written to the first region, based on whether a circuit has downloaded an image to be written to the first region from the first entity by way of the circuit 560. In an embodiment, the action includes providing an identity of the first region and the first entity to an image indicating signal downloading circuit or a coupling circuit, to disenable the downloading of the image indicating signal for the image to the electronic paper. In another embodiment, the action includes receiving the image indicating signal from the downloading circuit, or the coupling circuit, and not transmitting the signal to the electronic paper if the image is for the first region and written by the first entity.

In block 720, the method includes writing on a second region of the paper if the writing entity is a specific second entity. As described with reference to block 710, in embodiments, the circuit 660 is to determine whether an entity is endeavoring to write to a specified region of the electronic paper. If the entity endeavoring to write to the second region is not the second entity, in one embodiment the image indicating signal is disenabled from being downloaded to the electronic paper. In another embodiment, the image indicating signal is downloaded to the circuit 660, but the circuit 660 does not download the signal to the electronic paper.

In an embodiment, the method 700 includes in block 730, writing to a third region of the paper if the writing entity is a specific third entity. As described with reference to block 710, in embodiments the circuit is to determine whether an entity is endeavoring to write on a specified region of the electronic paper. If the entity endeavoring to write on the third region is not the third entity, in one embodiment the image indicating signal is disenabled from being downloaded to the electronic paper. In another embodiment, the image indicating signal is downloaded to the circuit, but the circuit does not download the signal to the electronic paper.

As described with reference to FIG. 1, in embodiments in which the electronic paper is associated with a product, such as being attached to the product or attached to a package of the product, the second entity may be a vendor of the product, the third entity may be a purchaser of the product, and/or the first entity may be a provider of the product to a vendor of the product, such as a manufacturer of the product or a distributor or publisher of the product.

Moreover, in an embodiment, the disenabling writing action described with reference to block 710 includes disenabling writing to the first region if the first entity has already written a specific number of images to the first region, such as a unitary number of images, or if the image written by the first entity to the first region is identified as a last image to be written by the first entity to the first region. Thus, if an image written by the first entity to the first region is not identified as the last image to be written on the first region, the first entity is not necessarily disabled from writing to the first region. In an embodiment, therefore, the writing to a first region of the electronic paper is substantially permanent, and the circuit 660 is configurable to substantially permanently write to a first region of the electronic paper, because entities are disenabled from writing to the first region. Moreover, in an embodiment the disenabling writing action described with reference to block 710 is executed only after an occurrence of event, such as only after a specific entity, such as a first entity, a second entity, and/or a third entity, indicates the event. In an embodiment, an event may be a specific quantity of times that the first region has been written to.

Figure 8A:
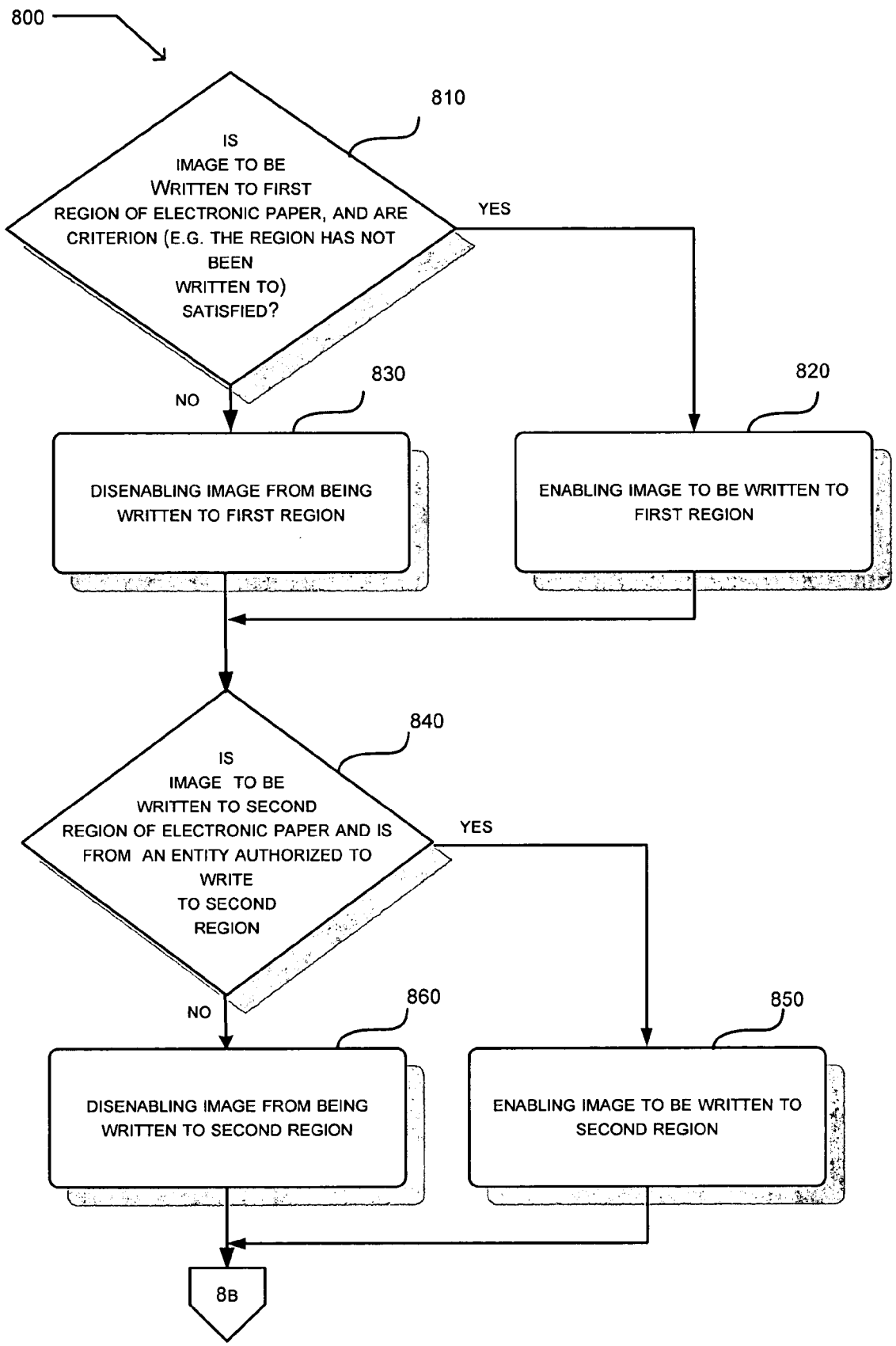
FIGS. 8A and 8B are a flow chart of another embodiment of a method of using electronic paper and the actions of a circuit configured to control the writing of an image on a region of the electronic paper.
Figure 8B:
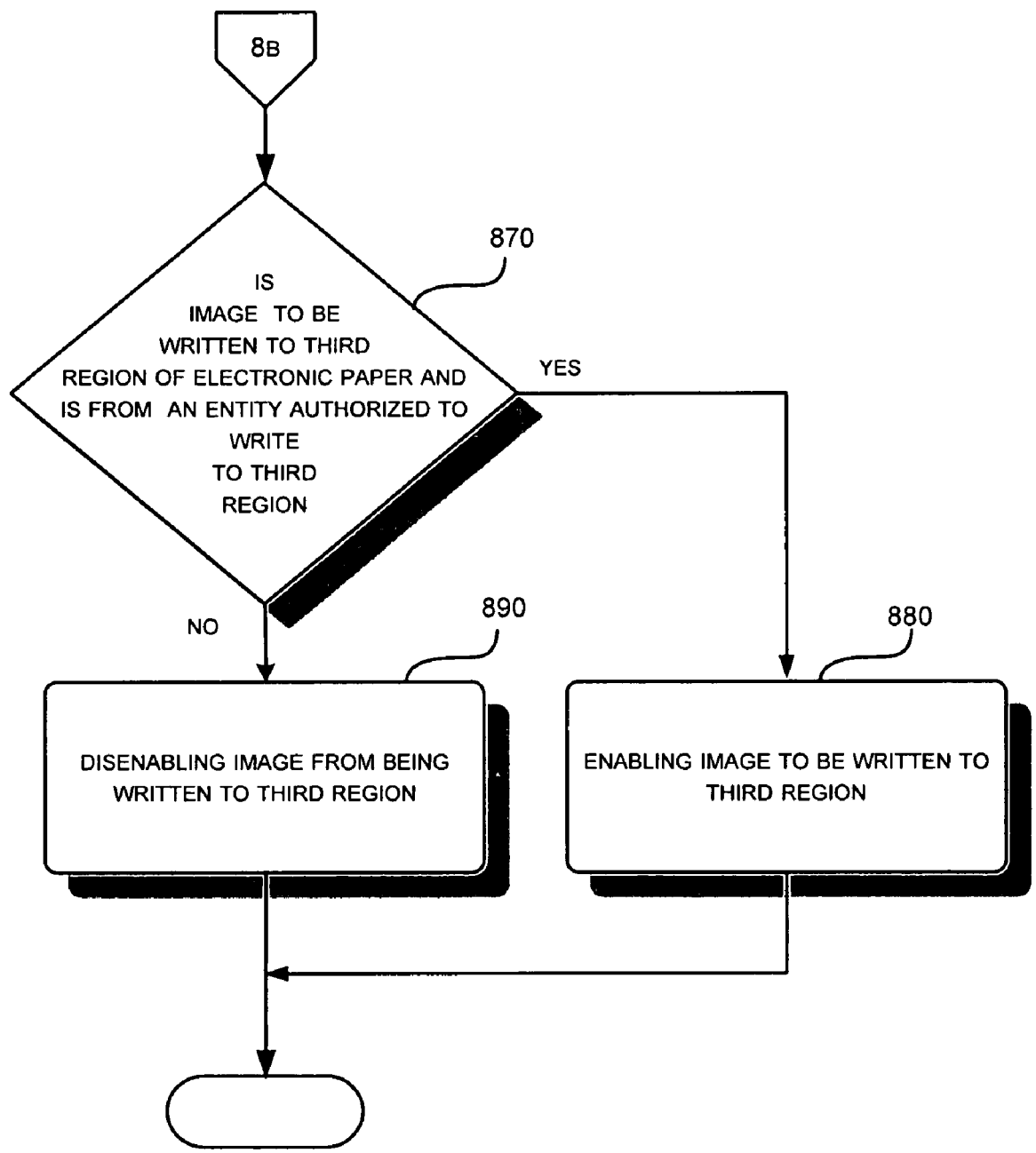

Referring now to FIGS. 8A and 8B, an embodiment of method 800 to conditionally disenable an entity from writing to a specific region of an electronic paper is portrayed. The method 800 includes in block 810 determining whether an image is to be written on a first region (or a part thereof) of an electronic paper, and if so, whether criteria to determine whether the image is to be written to the first region (or a part thereof) are satisfied. Such criteria may include in an embodiment, the occurrence or non-occurrence of an event. Illustrative sources of an event may be an input from a user interface, a datum indicating an event, or an algorithmic determination of an event. In embodiments, the event may include an image having already been written (or downloaded) to the first region a specified number of times such as one time, and/or written to the first region since a specified date; and/or whether a specified entity has written (or downloaded) an image to the first region a specified number of times, and/or written to the first region since a specified date. For these illustrative events, their non-occurrence indicates the satisfaction of the criteria to write to the first region or a part thereof). If the image is to be written to the first region (or a part thereof) of the electronic paper and the criteria have been satisfied, the YES branch is taken from block 810 to block 820. In block 820 the method includes enabling the image to be written to the first region (or a part thereof). If the image is to be written to the first region (or a part thereof) and the criteria have not been satisfied, the NO branch is taken from block 810 to block 830. In block 830, the method includes disenabling the image from being written to the first region (or a part thereof). In an embodiment therefore, the action of block 830 includes substantially permanently writing to a first region (or a part thereof) of the electronic paper, and the circuit 660 is configurable to substantially permanently write to a first region (or a part thereof) of an electronic paper, by disenabling writing to the first region (or a part thereof). In performing the actions of blocks 810, 820, and 830, circuitry is configurable to fix an image within at last a part of the first region by being configurable to write an image within at least a part of the first region, and to substantially disenable further input to the at least a part of the first region.

In block 840 the method 800 includes determining whether an image is to be written on a second region of the electronic paper is from an entity authorized to write on the second region. If an image is to be written on a second region and is from an entity authorized to write on the second region, then the YES branch is taken from block 840 and the method includes in block 850 enabling the image to be written to the second region. If an image is to be written on the second region and is not from an entity authorized to write on the second region, then the NO branch is taken from block 840 and the method includes in block 860 disenabling the image from being written to the second region. The method 800 therefore includes not enabling writing to the second region except by an authorized entity. In an embodiment, the method 800 moreover includes in block 870 determining whether an image is to be written on a third region of the electronic paper is from an entity authorized to write on the third region. If an image is to be written on a third region and is from an entity authorized to write on the third region, then the YES branch is taken from block 870 and the method includes in block 880 enabling the image to be written to the second region. If an image is to be written on the third region and is not from an entity authorized to write on the third region, then the NO branch is taken from block 870 and the method includes in block 890 disenabling the image from being written to the second region. The method 800 therefore includes not enabling writing to the third region except by an authorized entity.

As described with reference to FIG. 1, in embodiments in which the electronic paper is associated with a product, such as being attached to the product or attached to a package of the product, the entity authorized to write on the second region may be a vendor of the product, the entity authorized to write on the third region may be a purchaser of the product, and/or the entity authorized to write to the first region may be a provider of the product to a vendor of the product, such as a manufacturer of the product or a distributor or publisher of the product. In embodiments that depend upon a region of the electronic paper and an identity of an entity endeavoring to write to the region, the circuit 160 may be configured to read from the received image indicating signal an identity of the region to be written to, and an identity of the entity endeavoring to write to the region, and to transmit an indication of the image to the electronic paper 120 for entities enabled to write to a region.

Figure 9:
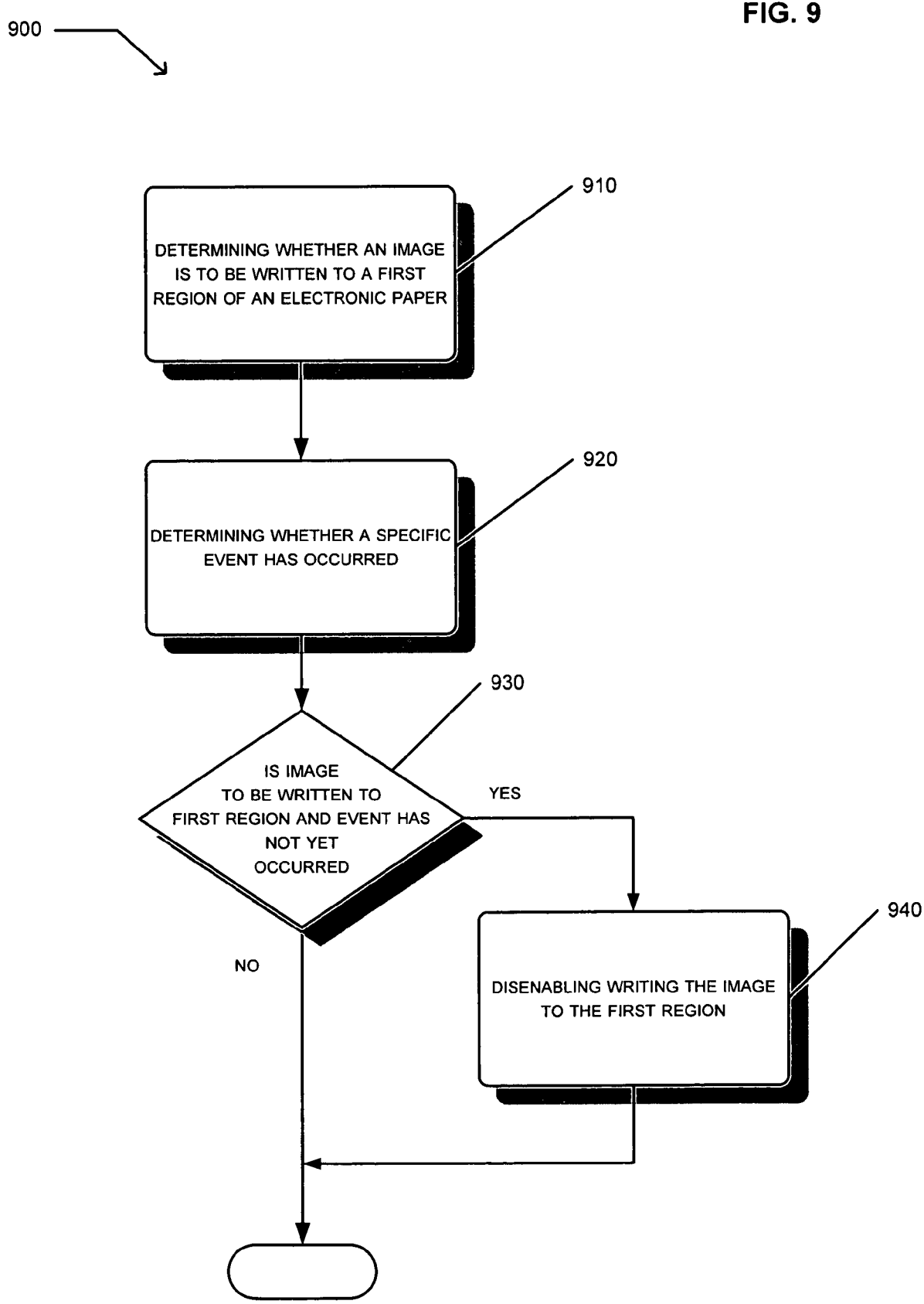
FIG. 9 is a flow chart of yet another embodiment of a method of using electronic paper and the actions of a circuit configured to control the writing of an image on a region of the electronic paper.

Referring to FIG. 9, an embodiment of a method 900 includes in block 910 determining whether an image is to be written to a first region of an electronic paper, and in block 920 determining whether a specific event has occurred. As described with respect to FIGS. 7 and 8A-8B, such an event may include a specific entity endeavoring to write on the region, an image already having been written to the region, and the entity having already written an image to the region a specified number of times, such as one time. If an image is to be written to a region and a specific event has occurred, the YES branch is taken from block 930, and in block 940 an action includes disenabling writing the image to the first region.

In an embodiment, the method 900 includes determining if the image is to be written to a specific other region and is from a specific entity. If the image is to be written to the other region and is not from the specific entity, the method 900 includes disenabling writing the image to the other region.

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

Figure 10:
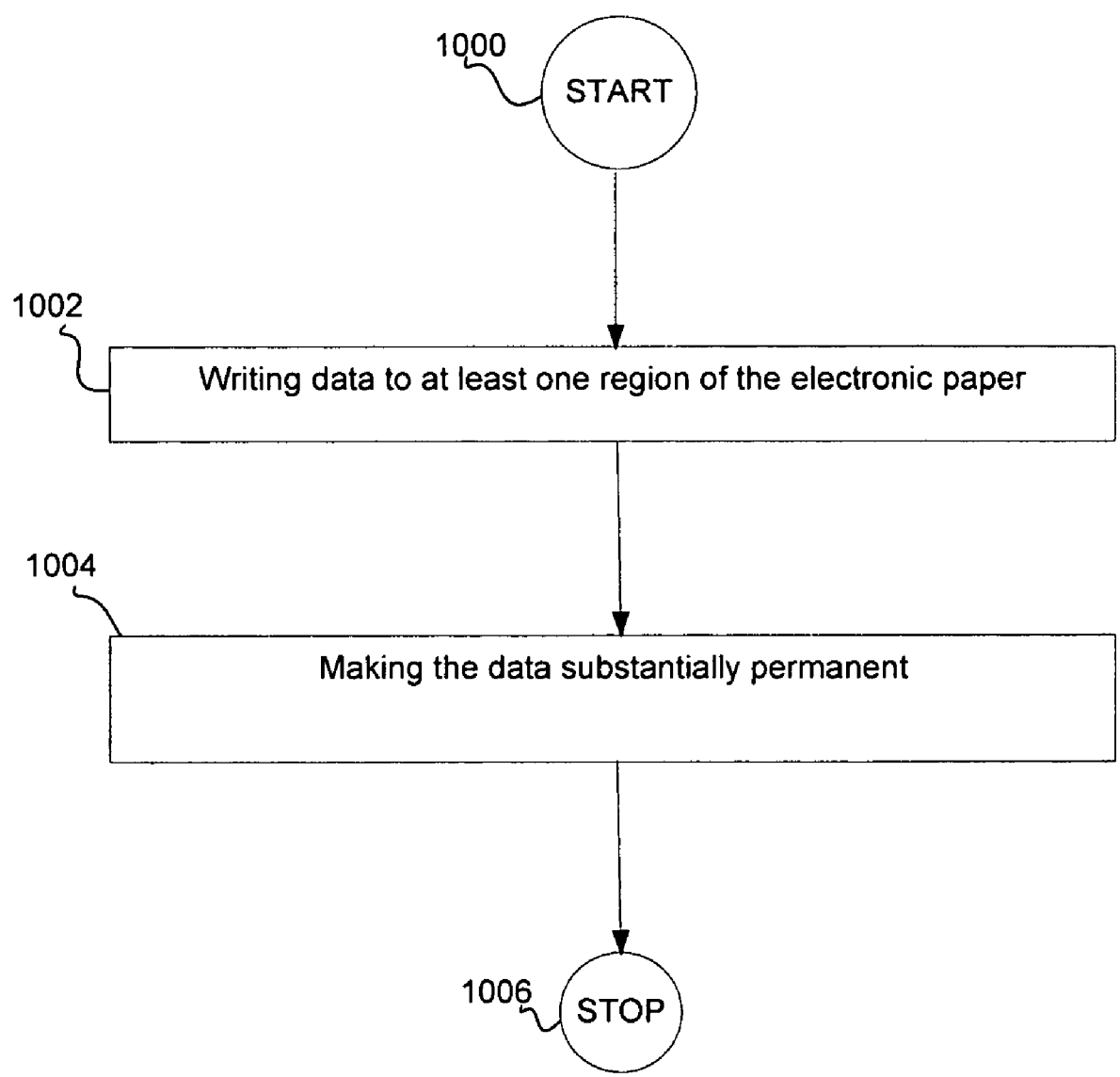
FIG. 10 shows a high-level logic flowchart of a process.

Referring to FIG. 10, shown is a high-level logic flowchart of a process. Method step 1000 depicts the start of the process. Method step 1002 illustrates writing data to at least one region of the electronic paper. For example, circuit 160 and/or 220 (or various combinations or permutations thereof within the ambit of those skilled in the art) writing a content to one or more pixels of electronic paper 120 (see, e.g., FIG. 2). Method step 1004 illustrates making the data substantially permanent. For example, circuit 160 and/or circuit 220 (or various combinations or permutations thereof within the ambit of those skilled in the art) activating a mechanism such that a pattern loaded to electronic paper 120 is substantially unmodifiable (see, e.g., FIG. 2). Method step 1006 shows the end of the process.

Figure 11:
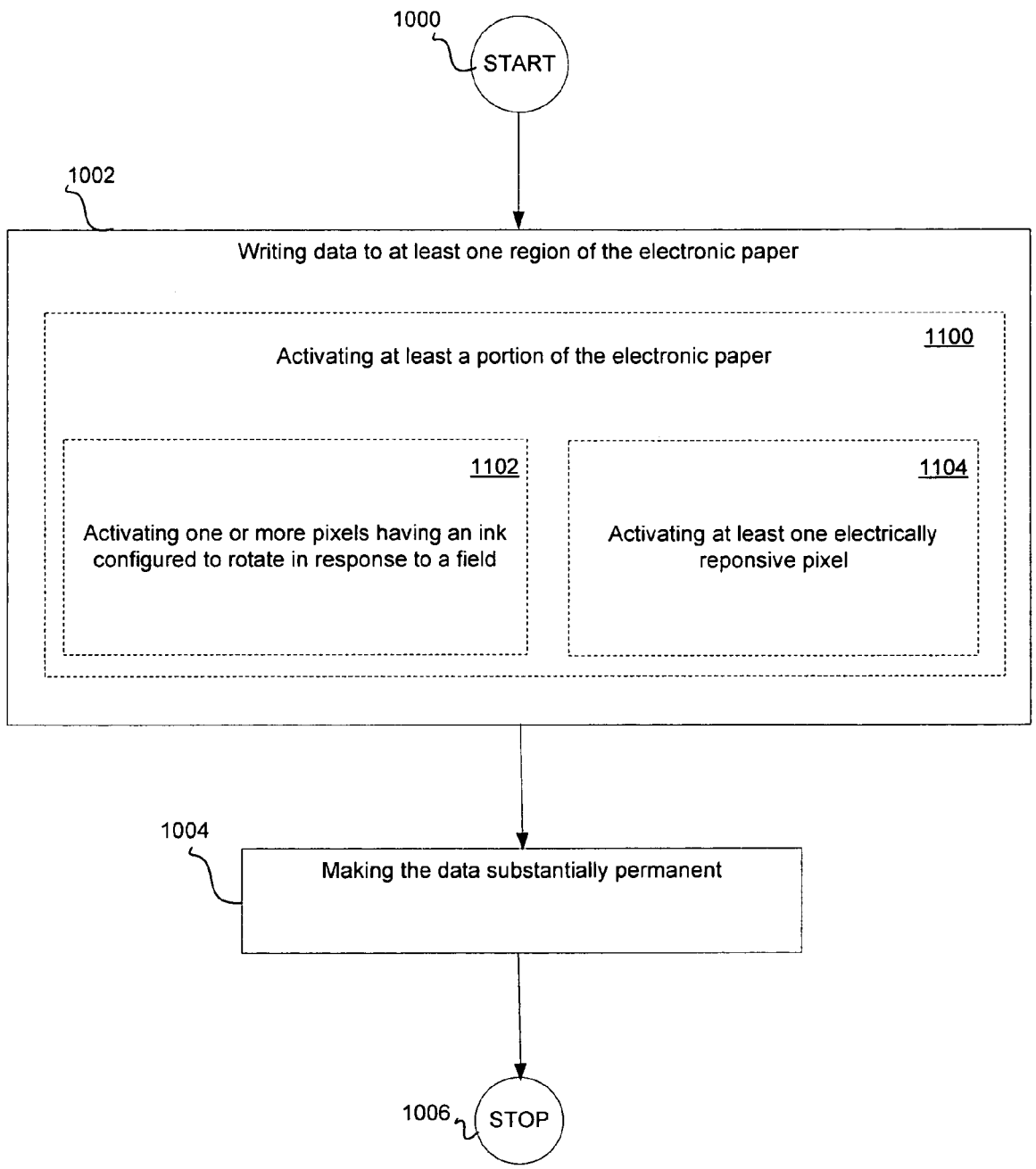
FIG. 11 depicts a high-level logic flowchart illustrating alternate implementations of the process of FIG. 10.

Referring to FIG. 11, depicted is a high-level logic flowchart illustrating alternate implementations of the process of FIG. 10. Shown is that in some implementations, method step 1000 may include method step 1100 which depicts activating at least a portion of the electronic paper. For example, circuit 160 and/or 220 (or various combinations or permutations thereof within the ambit of those skilled in the art) energizing one or more pixels of electronic paper 120 such that a desired pattern, such as forming text and/or an image, is formed on the paper (see, e.g., FIG. 2). Depicted is that in some implementations, method step 1100 may include method step 1102 which depicts activating one or more pixels having an ink configured to rotate in response to a field. For example, circuit 160 and/or 220 (or various combinations or permutations thereof within the ambit of those skilled in the art) energizing one or more pixels of electronic paper 120 utilizing electrophoretic and/or electrically and/or magnetically responsive ink (see, e.g., FIG. 2). Illustrated is that in some implementations, method step 1100 may include method step 1104 which depicts activating at least one electrically responsive pixel. For example, circuit 160 and/or 220 (or various combinations or permutations thereof within the ambit of those skilled in the art) energizing one or more pixels of electronic paper 120 utilizing electricity (see, e.g., FIG. 2). The remaining method steps function as shown and or described herein.

Figure 12:
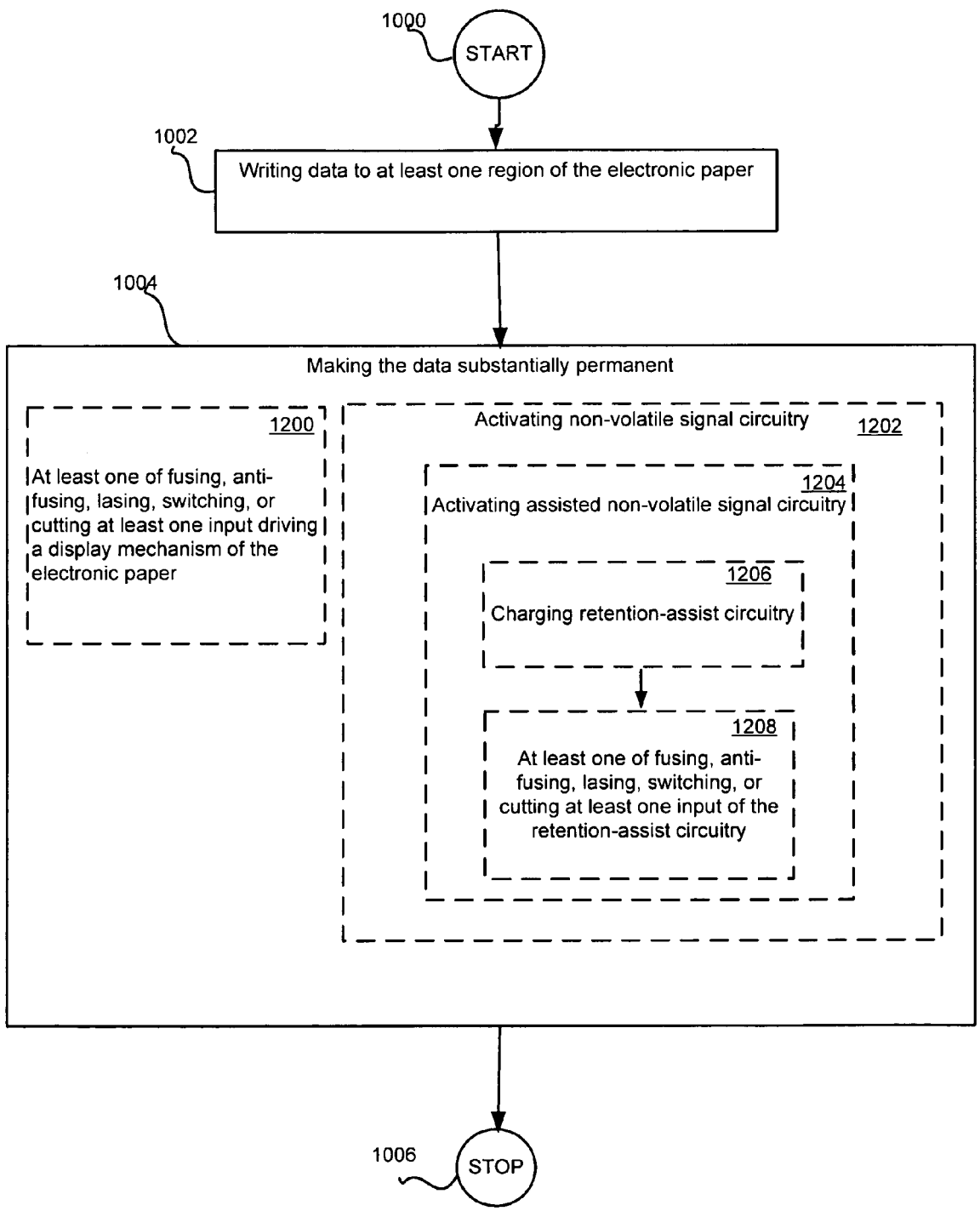
FIG. 12 illustrates a high-level logic flowchart illustrating alternate implementations of the process of FIG. 10.

Referring to FIG. 12, illustrated is a high-level logic flowchart illustrating alternate implementations of the process of FIG. 10. Shown is that in some implementations, method step 1004 may include method step 1200 which depicts at least one of fusing, anti-fusing, lasing, switching, or cutting at least one input driving a display mechanism of the electronic paper. For example, circuit 160 and/or 220 (or various combinations or permutations thereof within the ambit of those skilled in the art) activating a fuse, anti-fuse, laser, switch, or cutting mechanism respectively associated with circuitry driving one or more pixels of electronic paper 120 (see FIG. 2). Depicted is that in some implementations, method step 1004 may include method step 1202 which depicts activating non-volatile signal circuitry. For example, circuit 160 and/or 220 (or various combinations or permutations thereof within the ambit of those skilled in the art) energizing one or more pixels of electronic paper 120 (see FIG. 2). Illustrated is that in some implementations, method step 1202 may include method step 1204 which depicts activating assisted non-volatile signal circuitry. Depicted is that in some implementations, method step 1204 may include method steps 1206-08. Method step 1206 illustrates charging a retention-assist circuitry. For example, circuit 160 and/or 220 (or various combinations or permutations thereof within the ambit of those skilled in the art) charging retention-assist circuitry (e.g., capacitive and/or flash-memory like circuitry) respectively associated with one or more pixels of electronic paper 120 (see FIG. 2). Method step 1208 shows engaging in at least one of fusing, anti-fusing, lasing, switching, or cutting at least one input of the retention-assist circuitry. For example, circuit 160 and/or 220 (or various combinations or permutations thereof within the ambit of those skilled in the art) activating a fuse, anti-fuse, laser, switch, or cutting mechanism respectively associated with circuitry driving retention-assist circuitry respectively associated with one or more pixels of electronic paper 120 (see FIG. 2). The remaining method steps function as shown and or described herein.

Figure 13:
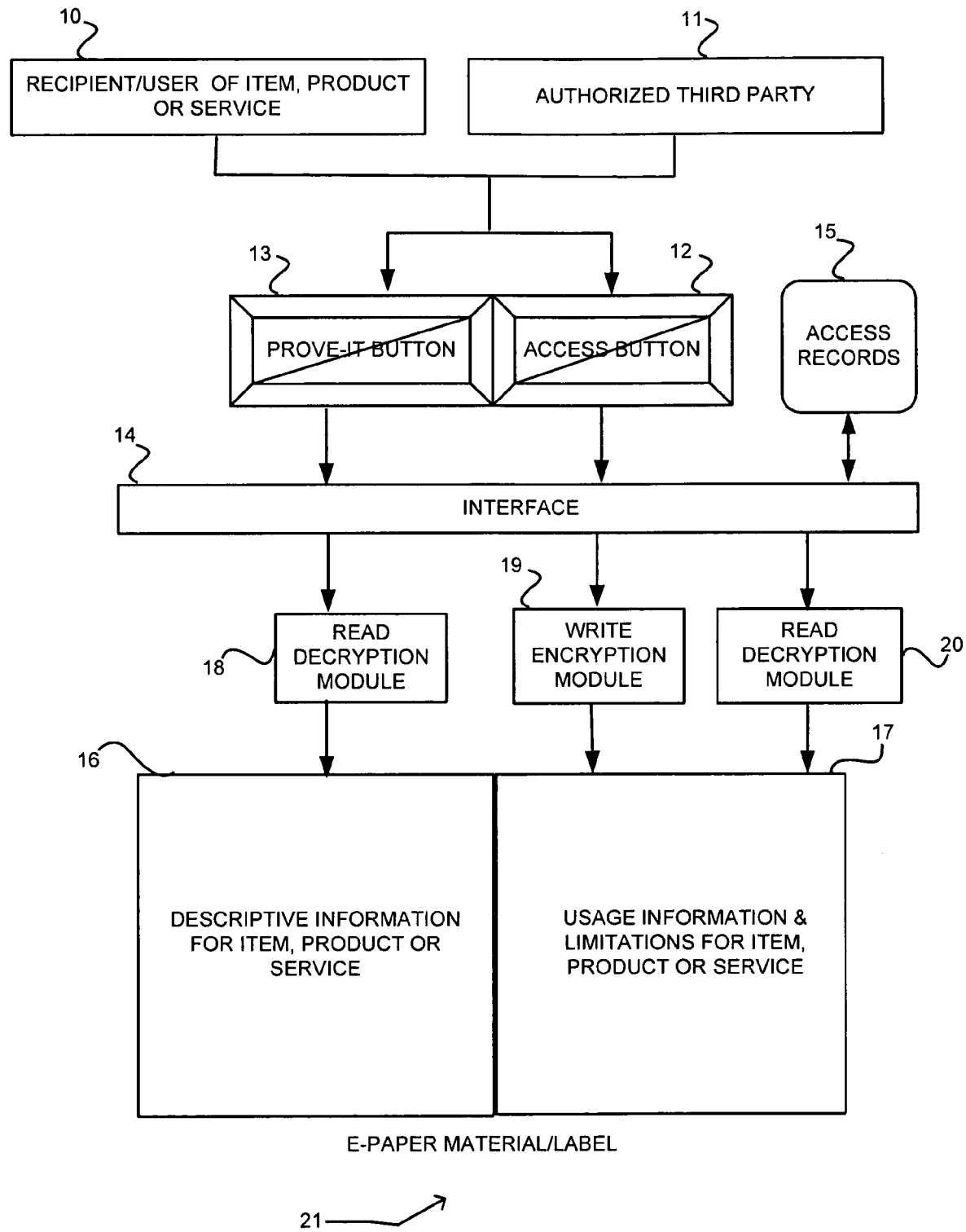
FIG. 13 is a schematic block diagram for a further embodiment showing read/write accessibility to electronic paper material.

Referring to the schematic block diagram of FIG. 13, an embodiment shows an exemplary read/write e-paper accessibility scheme for a recipient or user 10 of an item, product or service related to e-paper material 21. As disclosed herein, the e-paper material 21 may be associated with such item, product or service for various tracking, informational, certification and verification purposes. In some instances the e-paper material 21 also serves as a label attached to the associated item or product, and may also serve as a useful document related to the associated service.

The embodiment of FIG. 13 provides limited accessibility shown as an access button 12 that enables only authorized access for the recipient/user 10 (and in some instances for an authorized third party 11) through interface 14 via read decryption module 18 to an e-paper portion 16 having informational data such as encrypted descriptive information for the associated item, product or service. Limited accessibility is also provided through interface 14 via write encryption module 19 and also via read decryption module 20 to an e-paper portion 17 having informational data such as encrypted usage information and limitations that are applicable to the associated item, product or service.

Access records 15 may be configured to be operably connected with interface 14 in order to monitor and save pertinent information regarding any use of the interface 14 for obtaining access to e-paper material 21.

The embodiment of FIG. 13 also includes verification accessibility shown as a prove-it button 13 that enables authorized access through interface 14 to determine whether any alteration has been made to the descriptive information on portion 16, and also to determine whether any alteration has been made to the usage information and limitations on portion 17.

Figure 14:
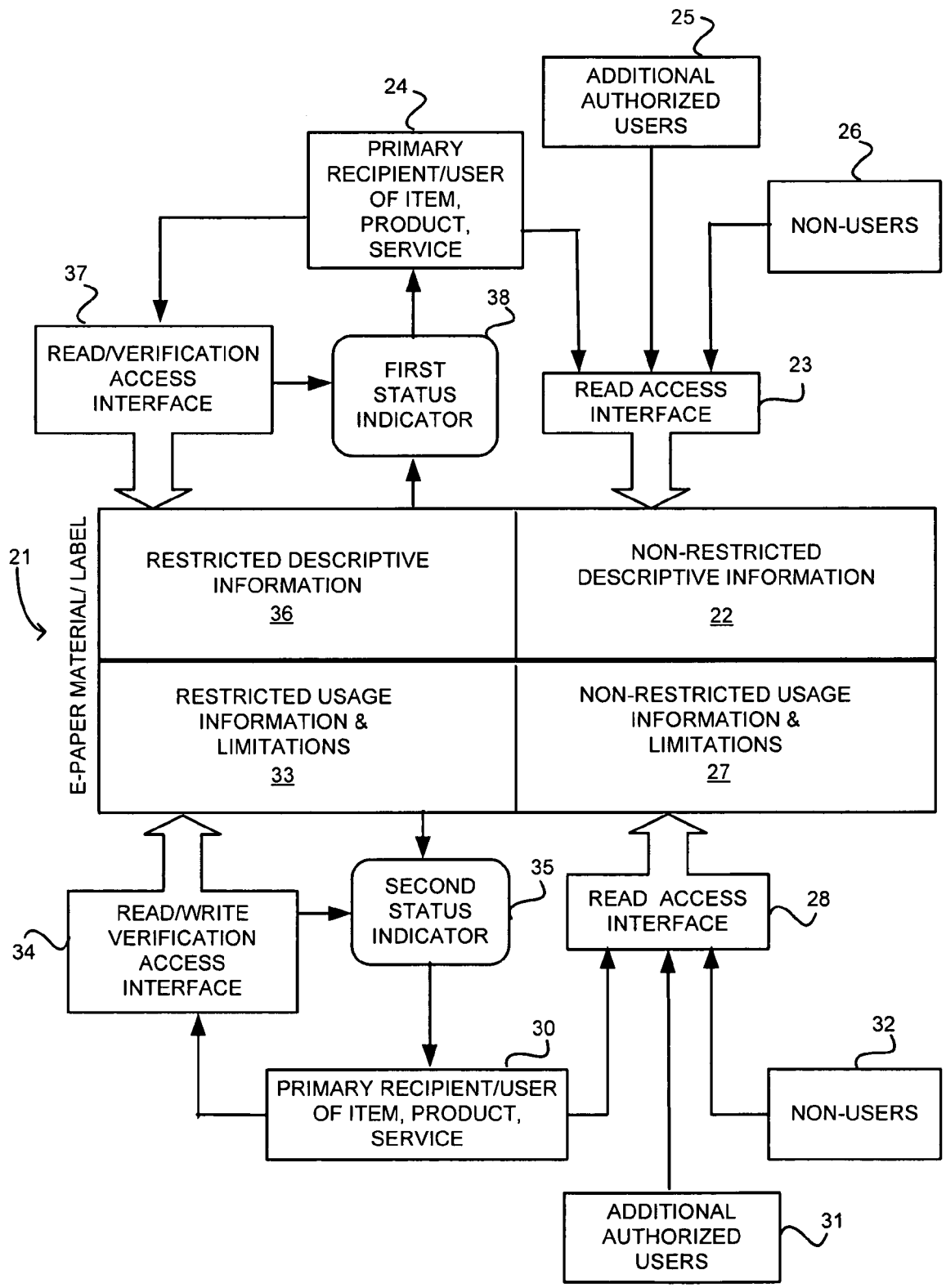
FIG. 14 is a schematic block diagram showing an exemplary embodiment that includes status indicators for verification of information on electronic paper material.

Referring to the schematic block diagram of FIG. 14, another embodiment is depicted that includes status indicators for communicating verification output information regarding the e-paper material 21. In this embodiment it will be understood that different levels of accessibility are provided with respect to different types of data on the e-paper material 21. With respect to non-restricted descriptive information on portion 22, a read access interface 23 is available to a primary recipient (or primary user) 24 of an item, product or service associated with the e-paper material 21. The read access interface 23 is also available to additional authorized users 25, and in some instances to non-users 26.

Similarly with respect to non-restricted usage information and limitations on portion 27, a read access interface 28 is available to a primary recipient (or primary user) 30 of an item, product or service associated with the e-paper material 21. The read access interface 28 is also available to additional authorized users 31, and in some instances to non-users 32. It will be understood that a primary recipient or user designated as 24 may be interested only (or especially) in reading the non-restricted descriptive information in portion 22, and a different primary recipient or user designated as 30 may be interested only (or especially) in reading the non-restricted usage information and limitations in portion 27. However, in this embodiment the status indicators are not configured to provide any verification feedback regarding the data written in the non-restricted portions 22, 27.

In contrast, the embodiment of FIG. 14 provides accessibility safeguards and verification feedback with respect to data written in the restricted portions 33, 36 of the e-paper material 21. More particularly, the primary recipient or user 24 has accessibility through read/verification access interface 37 to the restricted descriptive information in portion 36, and in addition may receive verification feedback from a first status indicator 38. Similarly, the primary recipient or user 30 has accessibility through read/verification access interface 34 to the restricted usage information and limitations in portion 33, and in addition may receive verification feedback from a second status indicator 38.

Figure 15:
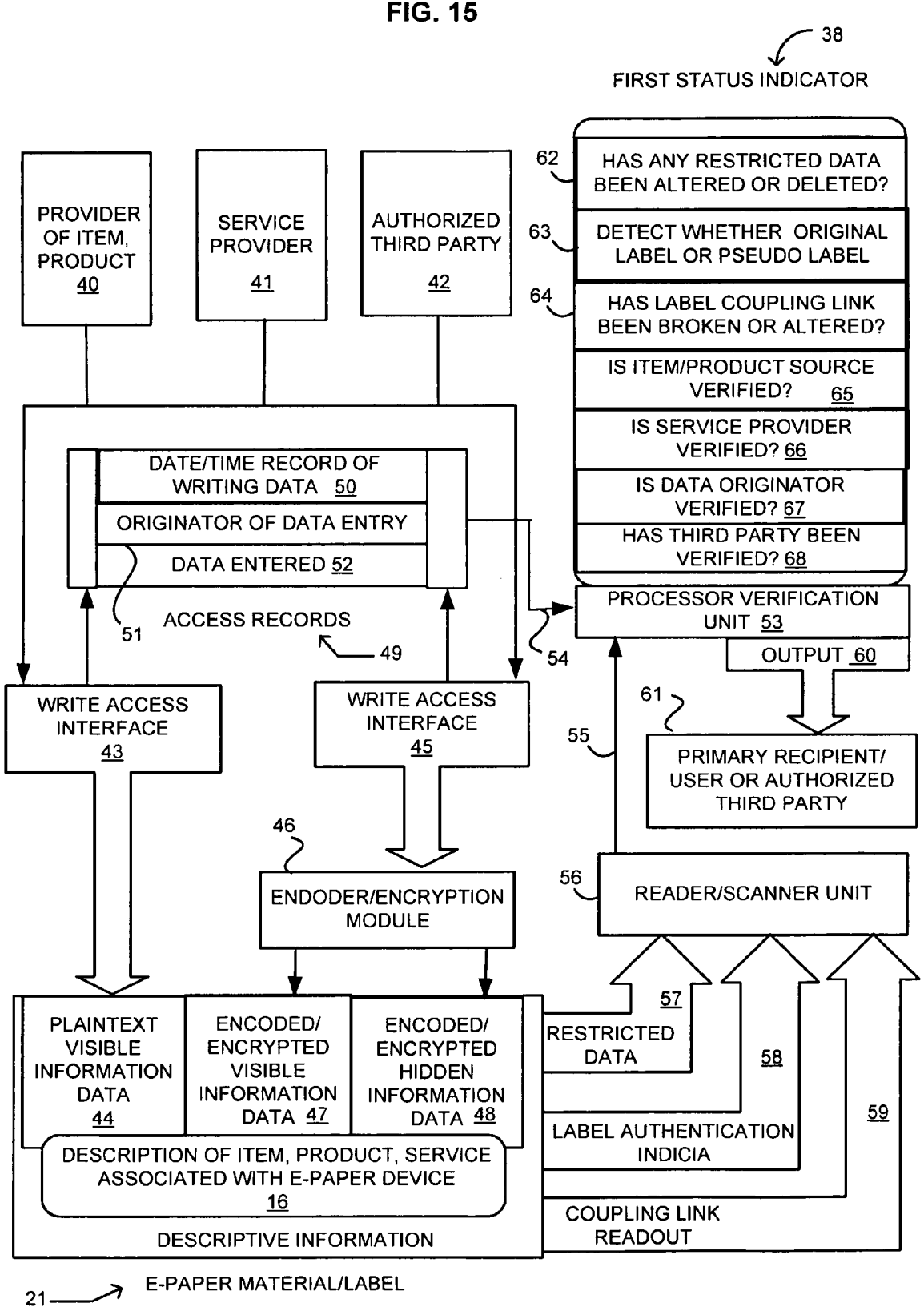
FIG. 15 is a schematic block diagram showing another exemplary embodiment that includes a reader/scanner unit that is operably coupled with a first status indicator.

Detailed implementation details are shown in the embodiment depicted in the schematic block diagram of FIG. 15, wherein the e-paper material 21 is shown as part of an exemplary system implementation. In this embodiment involving usage information and limitations entered on portion 16 of e-paper material 21 (see FIG. 13), a reader/scanner unit 56 is operably coupled through a processor verification unit 53 to the first status indicator 38 in order to provide a verification output 60 from the first status indicator 38 to a primary recipient, user or authorized third party 61.

As shown in FIG. 15, a provider 40 of an item or product, as well as a service provider 41, and an authorized third party 42 all may be enabled via write access interface 43 to make data entries of plaintext visible information data 44 on portion 16 of e-paper material 21. The same three entities (or persons) may also be enabled via write access interface 45 to use an encoder/encryption module 46 to make entries of protected visible information data 47 and protected hidden information data 48 on portion 16 of e-paper material 21. Such entries are enabled by the encoder/encryption module 46 in accordance with an appropriate security methodology.

Access records 49 are operably connected with the two write access interfaces 43, 45 in order to save pertinent access records such as date/time of writing data 50, originator of data entry 51, and data entered 52. Other access record data fields may be included in addition to those disclosed herein, and in some instances some of the exemplary status output data fields may not be deemed desirable and therefore can be omitted. Such access records 49 are made available as shown by arrow 54 to processor verification unit 53. The processor verification unit 53 also receives inputs shown by arrow 55 from the read/scanner unit 56 for different types of verification information including but not limited to verification confirmation for restricted data 57, and for label authentication indicia 58, and for coupling link readout 59.

The processor verification unit 53 can then process the various inputs in accordance with the predetermined security methodology in order to generate selected status outputs to the first status indicator 38. Exemplary types of status output fields may include answers regarding whether any restricted data has been altered or deleted 62, detection result of whether the e-paper material constitutes the original label (or a pseudo label) 63, whether a label coupling link to an attached item or product has been broken or altered 64, is the item or product source verified 65, is the service provider verified 66, is the data originator verified 67, and has the authorized third party been verified 68. Other status output fields may be included in addition to those disclosed herein, and in some instances some of the exemplary status output data fields may not be deemed desirable and therefore can be omitted.

Selected output versions 60 from the first status indicator 38 are made available to approved entities 61 such as a primary recipient or user of the item, product or service, as well as to any authorized third parties.

Figure 16:
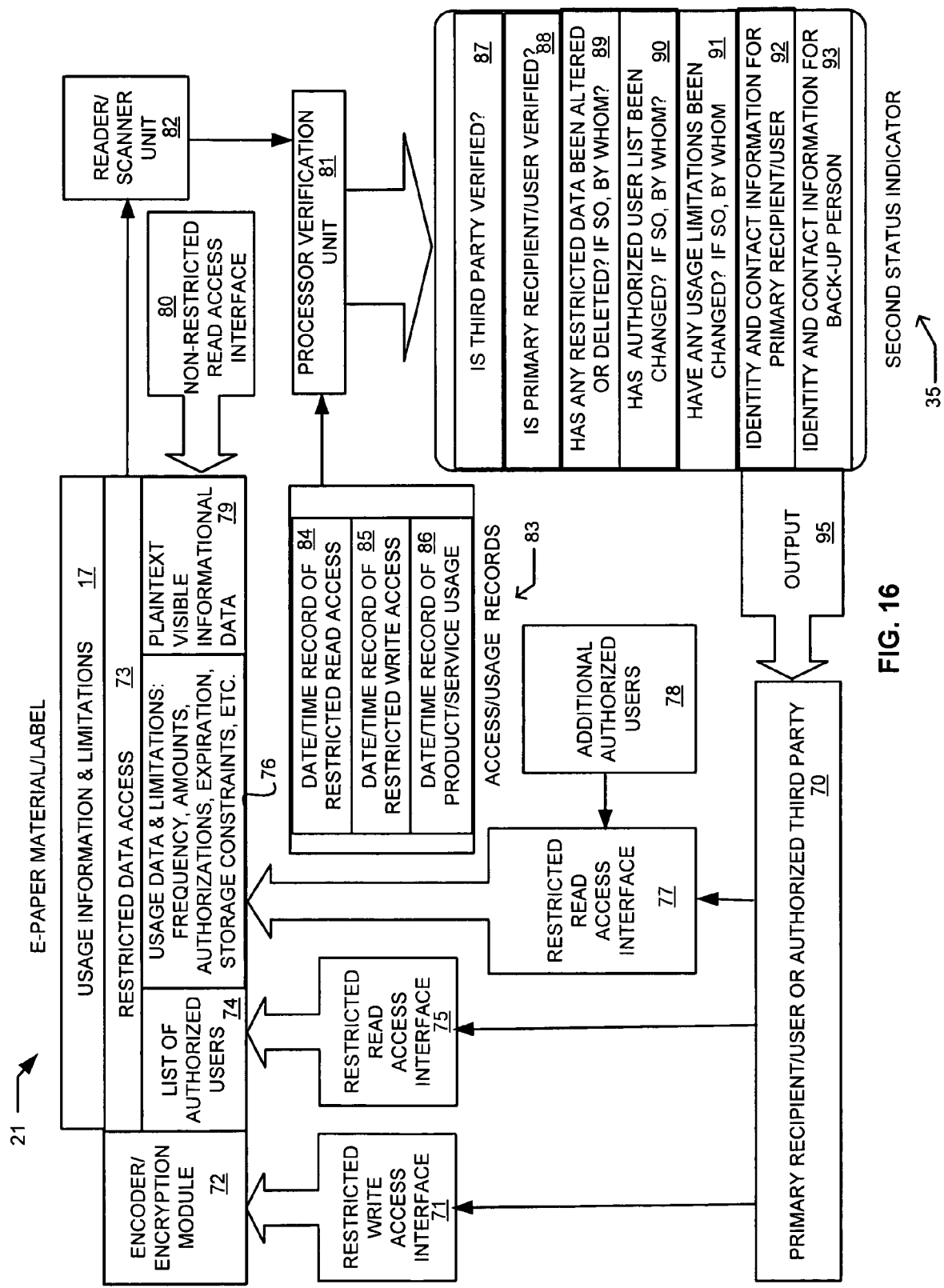
FIG. 16 is a schematic block diagram showing additional exemplary embodiment that includes a reader/scanner unit that is operably coupled with a second status indicator.

Other detailed implementation details are shown in the embodiment depicted in the schematic block diagram of FIG. 16, wherein the e-paper material 21 is shown as part of another exemplary system implementation. In this embodiment involving usage information and limitations entered on portion 17 of e-paper material 21 (see FIG. 13), a reader/scanner unit 82 is operably coupled through a processor verification unit 81 to the second status indicator 35 in order to provide a verification output 95 to a primary recipient, user or authorized third party 70.

As shown in FIG. 16, an authorized entity such as a primary recipient, primary user or authorized third party 70 all may be enabled via restricted write access interface 71 to make data entries on restricted data access portion 73 of the e-paper material 21. Such data entries will be enabled by encoder/encryption module 72 in accordance with an appropriate security methodology. The same three categories of entities 70 (or persons) may be enabled via restricted read access interface 75 to read a list of authorized users on restricted portion 74 of e-paper material 21, and also may be enabled via restricted read access interface 77 to read informational data entries on restricted portion 76 of e-paper material 21. Examples of informational data entries on restricted portion 76 include usage data and limitations, amounts, authorizations, expiration, storage constraints, etc. Additional authorized users 78 may also be enabled via restricted read access interface 77 to read such informational data entries on restricted portion 76.

Access records 83 are operably connected with restricted write access interface 71 as well as with the two restricted read access interfaces 75, 77 in order to save pertinent access records such as date/time of restricted read access 84, date/time record of restricted write access 85, and date/time record of product/service usage 86. Other access record data fields may be included in addition to those disclosed herein, and in some instances some of the exemplary status output data fields may not be deemed desirable and therefore can be omitted. Such access records 49 are made available as shown by an arrow to processor verification unit 81. The processor verification unit 81 also receives inputs shown by arrow from the read/scanner unit 82 for different types of verification information including but not limited to verification confirmation for the restricted data in restricted portions 74, 76.

Although write access to portion 79 containing plaintext visible informational data may in some instances be restricted to authorized parties using restricted write access interface 71, the exemplary embodiment of FIG. 16 shows that portion 79 may be generally available through non-restricted read access interface 80.

The processor verification unit 81 can then process the various inputs in accordance with the predetermined security methodology in order to generate selected status outputs to the second status indicator 35. Exemplary types of status output fields may include answers regarding whether a third party is verified 87; whether a primary recipient or primary user is verified 88; has an restricted data been alter or deleted, and if so by whom 89; has the authorized user list been changed, and if so by whom 90; have any usage limitations been changed, and if so by whom 91; listing identity and contact information for a primary recipient or user 92; and listing identity and contact information for a back-up person 93. Other status output fields may be included in addition to those disclosed herein, and in some instances some of the exemplary status output data fields may not be deemed desirable and therefore can be omitted.

Selected output versions 95 from the second status indicator 35 are made available to approved entities 70 such as a primary recipient or user of the item, product or service, as well as to any authorized third parties.

Figure 17:
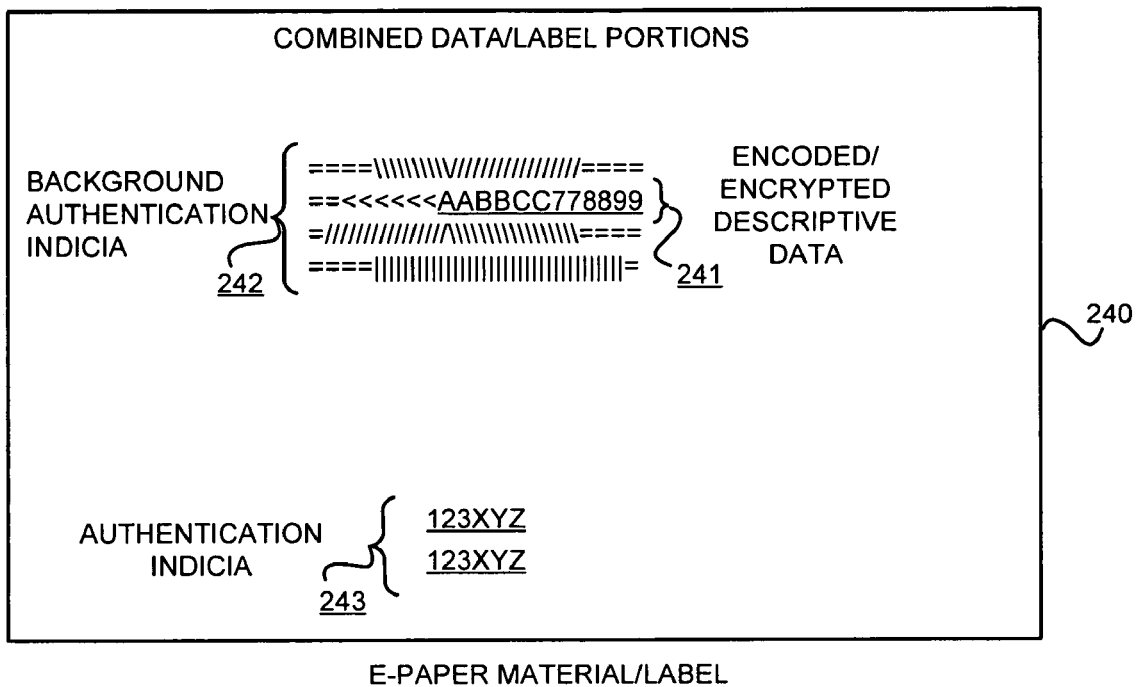
FIGS. 17 and 18 are top view diagrams that schematically show different exemplary implementations of data and authentication indicia incorporated on electronic paper material.

A top view diagram of FIG. 17 schematically shows an exemplary implementation of data and authentication indicia incorporated on combined partially overlapping data/label portions of an e-paper document 240. In this embodiment, encoded or encrypted descriptive data 241 is surrounded (and in some instances overlies) background authentication indicia 242. Alternative or supplemental authentication indicia 243 may be provided separate and apart from the descriptive data 241.

Figure 18:
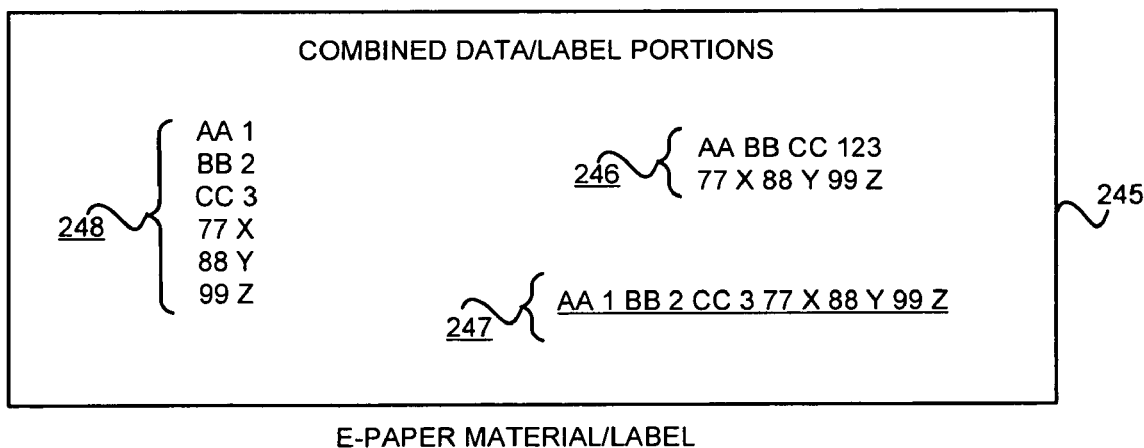

Another top view diagram of FIG. 18 schematically shows a different exemplary implementation of data and authentication indicia incorporated on combined overlapping data/label portions of an e-paper document 245. In this embodiment the encoded or encrypted descriptive data designated as 241 in FIG. 17 has been intermixed with the authentication indicia designated as 243 in FIG. 17 to form different customized composite authentication patterns 246, 247, 248.

Figure 19:
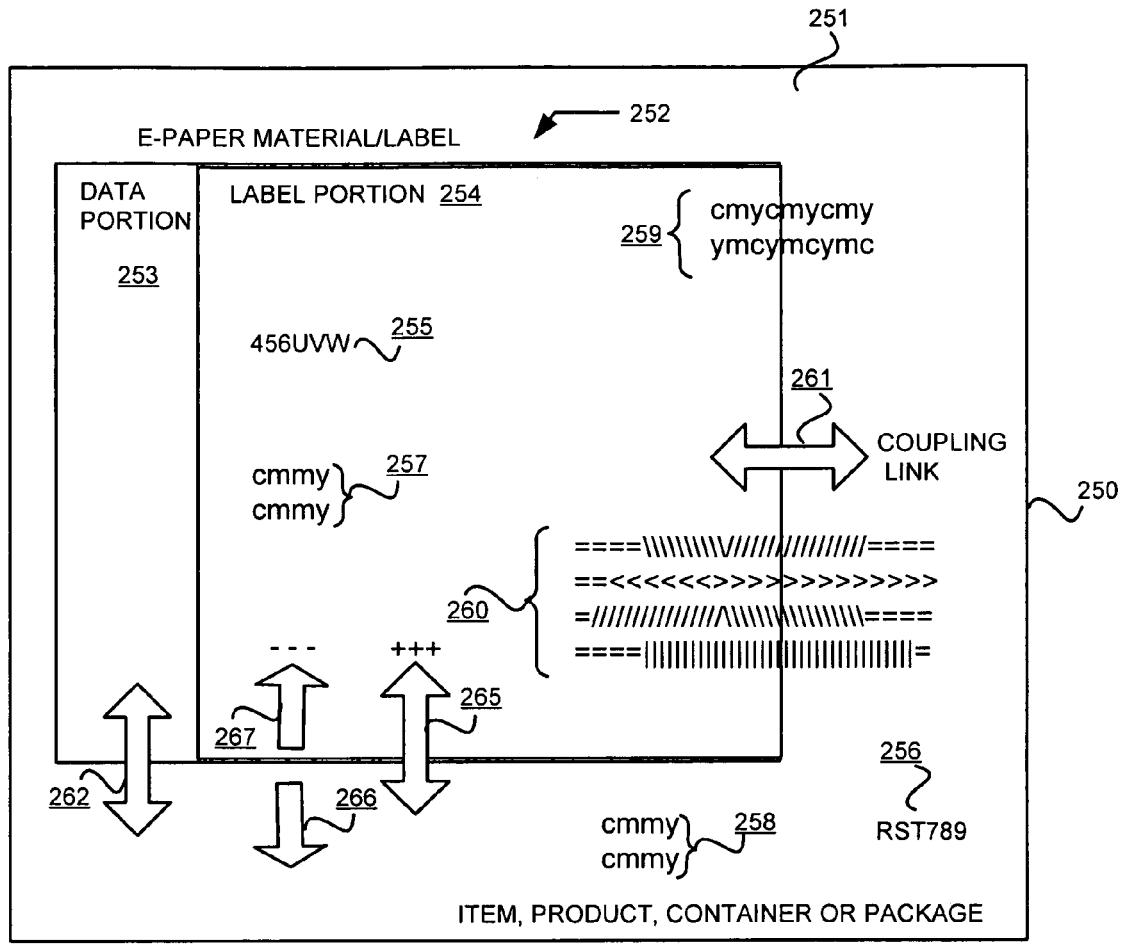
FIG. 19 is a top view diagram that schematically shows an exemplary implementation of authentication indicia incorporated on a label-type of electronic paper material attached to an associated item, product, container or package.

A further top view diagram of FIG. 19 schematically shows another exemplary implementation of authentication indicia incorporated on an e-paper document 252 attached to an associated item 250 (or product, container, or package). The e-paper document 252 includes a data portion 253 and a label portion 254. The label portion 254 includes several implementation examples of validating link components that are encoded or encrypted in accordance with a predetermined security methodology. The correlated link components on both the label portion 254 and item 250 are shown in the following exemplary formats: separated alphanumeric components 255, 256; separated color (cyan, magenta, yellow) representations 257, 258; contiguous cross-boundary color representations 259; and contiguous cross-boundary pattern representations 260.

Arrow 261 represents generally any coupling link to the label portion 254. Arrow 262 represents generally any coupling link to the data portion 253. Arrow 265 represents generally a non-altered coupling link to label portion 254, which creates a "positive" pixel display as an "ok" alert output on the label portion 254 when no alteration is detected. A defective (e.g., altered, broken, detached, damaged, missing) coupling link represented generally by separated arrow heads 266, 267 causes a "warning" alert output shown as a "negative" pixel display on the label portion 254. Although the illustrated coupling links are illustrated on a top surface 251 of item 250, other surfaces of both the item and the e-paper document may be used to establish a coupling link, as better shown in FIG. 20. Pixel displays may also be used for other types of verification status outputs.

Figure 20:
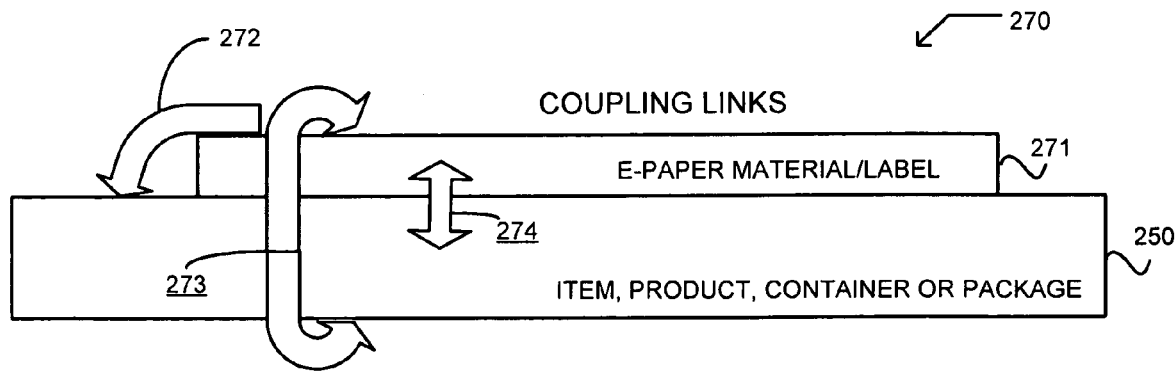
FIG. 20 is a side view diagram that schematically illustrates different types of verification coupling links between a label-type of electronic paper material and an attached or associated item, product, container or package.

A side view diagram of FIG. 20 is a schematic illustration of a composite unit 270 showing different types of verification coupling links between an e-paper document 271 and the attached or associated item, product, container or package 250. Such coupling links could be implemented on adjacent surfaces 272, opposite surfaces 273, facing surfaces 274, or other surface combinations.

Figure 21:
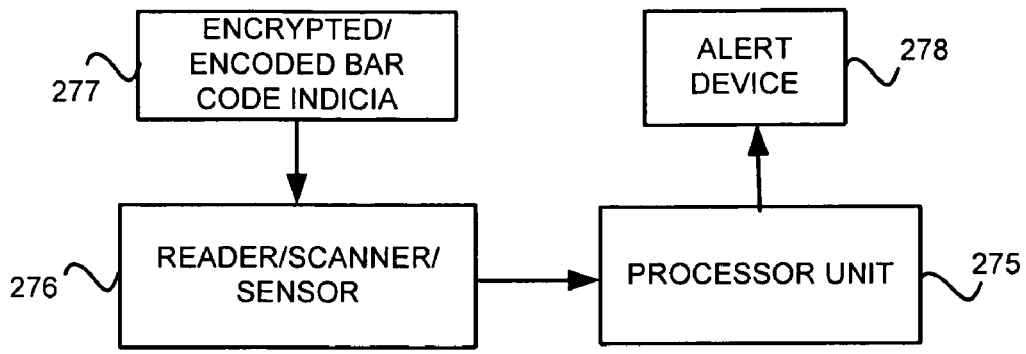
FIG. 21 is a schematic block diagram for an exemplary electronic paper system that includes an alert device.

FIG. 21 is a schematic block diagram for an exemplary e-paper verification embodiment wherein a processor unit 275 receives input from a reader (e.g., scanner, sensor) 276 that has a capability to detect encrypted or encoded bar code indicia 277. The processor unit uses an appropriate security methodology in order to provide a status output to an alert device 278.

Figure 22:
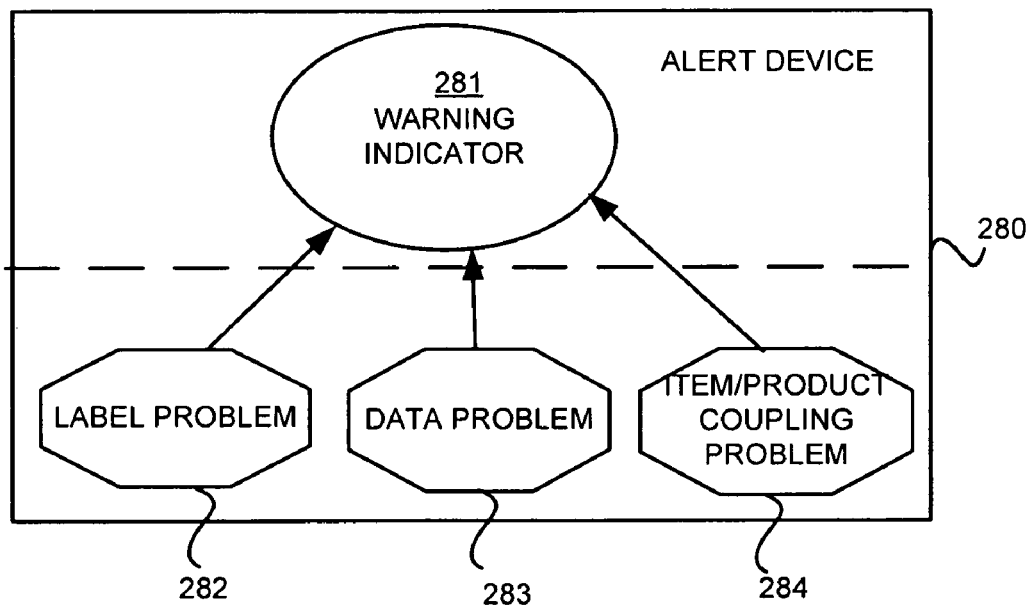
FIG. 22 is a schematic diagram for an exemplary alert device with an indicator that receives status information regarding multiple types of e-paper verification problems.

An exemplary embodiment of an alert device 280 is depicted in the schematic diagram of FIG. 22 wherein a warning indicator 281 can provide an "ok" alert output (e.g., text, alphanumeric, symbol, audio, visual, audiovisual, color) when an e-paper system determines that no verification problem has been detected, or alternatively the same warning indicator 281 can provide a "warning" alert output (e.g., text, alphanumeric, symbol, audio, visual, audiovisual, color) when any verification involving multiple problem types has been detected. In this embodiment, the warning indicator 281 provides a status indication regarding multiple types of verification problems such as a label verification problem 282, a data verification problem 283, and an item or product coupling verification problem 284. Of course, other types or combinations of e-paper verification problems could be implemented in an e-paper verification system, and the specific examples disclosed herein are for purposes of illustration only.

Figure 23:
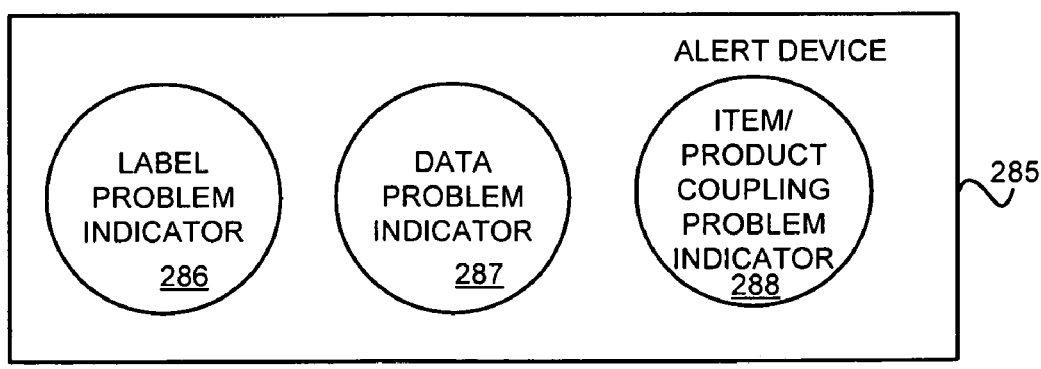
FIG. 23 is a schematic diagram for another exemplary alert device with separate indicators respectively provided for different types of e-paper verification problems.

Another exemplary embodiment shown in the schematic diagram of FIG. 23 depicts an alert device 285 with separate status indicators respectively provided for different types of e-paper verification problems. The illustrated examples in FIG. 23 include a label problem status indicator 286, a data problem status indicator 287, and an item (e.g., product) coupling problem indicator 288. As previously mentioned with respect to FIG. 22, various output techniques can be incorporated as part of "ok" and "warning" output alerts, and various other combinations and types of verification problems could be pre-selected to be monitored and detected.

Figure 24:
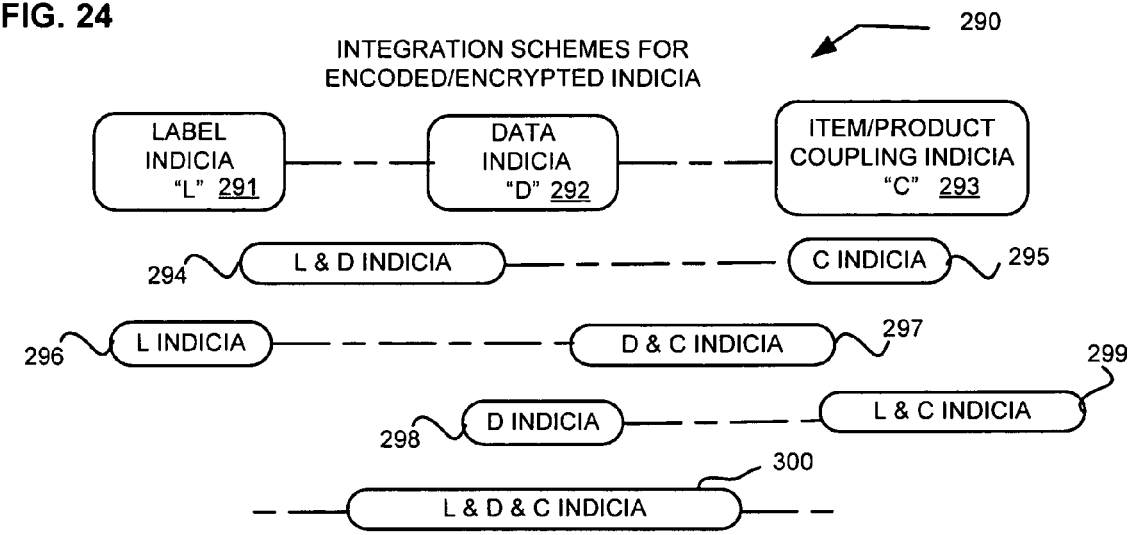
FIG. 24 is a diagram illustrating different exemplary integration schemes for encoded or encrypted indicia on e-paper material.

The schematic diagram of FIG. 24 illustrates various exemplary schemes 290 for integrating authentication indicia involving different types of e-paper verification problems, such as label indicia abbreviated as "L" 291, data indicia abbreviated as "D", and item or product coupling indicia abbreviated as "C" 293. In some embodiments each type of authentication indicia could be displayed and/or scanned separately.

It will be understood by those skilled in the art that various considerations such as security methodology and ease of detection and alert device features may dictate a preferred integration format; accordingly the exemplary schemes depicted herein are not intended to be exhaustive. By way of illustration only, a possible format could combine (e.g., intermix, integrate) the label/data authentication indicia 294 while the coupling authentication indicia 295 could be a separate display. Another possible format could display label authentication indicia 296 separately while combining data/coupling authentication indicia 297. A further possible format could display data authentication indicia 298 separately while combining label/coupling authentication indicia 299. An additional possible format could combine together the label/data/coupling authentication indicia 300. Of course in some instances an individual type of e-paper verification problem could nevertheless be detected, processed and identified as a result of scanning either a separated format or an integrated format.

Figure 25A:
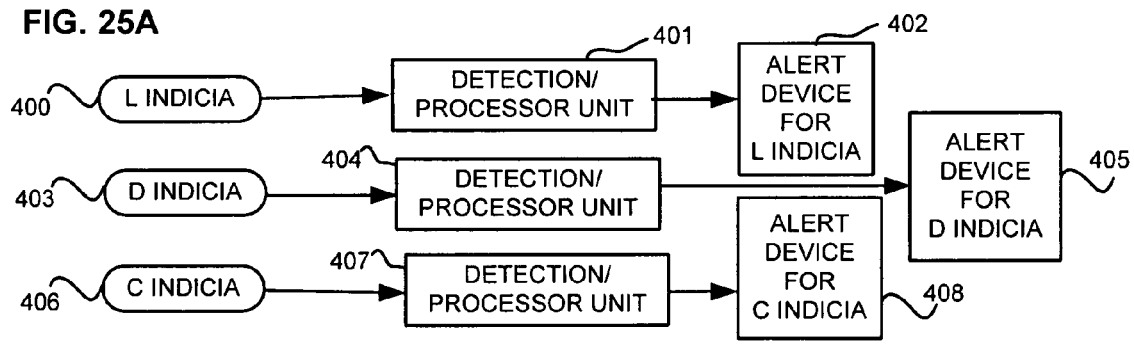
FIGS. 25A, 25B and 25C are schematic block diagrams showing different exemplary implementations for obtaining, processing and displaying verification status outputs from e-paper material.

Referring to FIG. 25A, an exemplary embodiment may include label authentication indicia 400 for providing an input to detection/processor unit 401 in order to generate status information to a respective alert device 402. Similarly data authentication indicia 403 will provide an input to detection/processor unit 404 in order to generate status information to a respective alert device 405. Similarly coupling authentication indicia 406 will provide an input to detection/processor unit 407 in order to generate status information to a respective alert device 408.

Figure 25B:
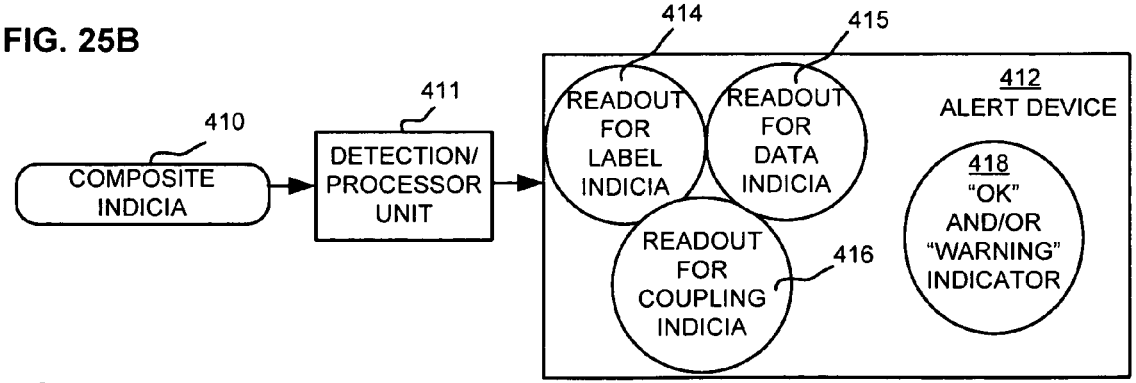

Referring to FIG. 25B, another exemplary embodiment may include composite authentication indicia 410 for providing an input to detection/processor unit 411 in order generate appropriate output information to alert device 412. The alert device 412 includes a first status readout 414 for label verification, a second status readout 415 for data verification, and a third status readout 416 for coupling verification. The alert device 412 of this embodiment also includes a warning indicator 418 that provides an overall status alert output, such that a verification problem with any type of e-paper verification will generate a "warning" output at indicator 418. Alternatively if no verification problem of any type is detected, an "ok" output will be generated at indicator 418.

Figure 25C:
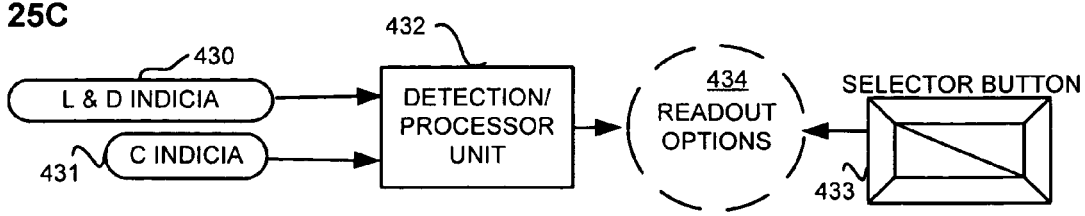

Referring to FIG. 25C, a further exemplary embodiment may include combined label/data authentication indicia 430 as well as separate coupling authentication indicia 431 which together provide input to detection/processor unite 432. A user selection feature such as selector button 433 enables a user to choose readout options 434 for reviewing any and all available permissible outputs relating to e-paper verification status information.

Figure 26:
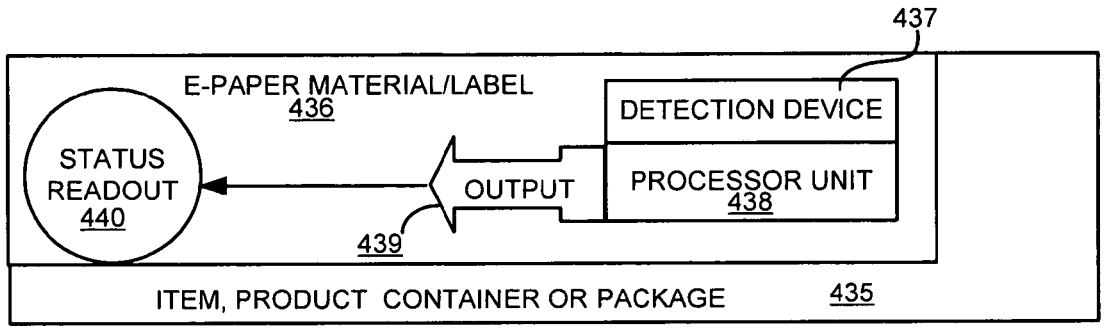
FIGS. 26, 27 and 28 are schematic block diagrams showing different exemplary embodiments with various verification component locations.

The schematic block diagram of FIG. 26 depicts an exemplary embodiment for an e-paper device that includes an e-paper label 436 with its associated (e.g., attached) item, product, container or package 435. In this embodiment, various components are incorporated with the e-paper device including a detection device 437, a processor unit 438, and a status readout 440. The processor unit 438 uses an appropriate security methodology to process scanned e-paper data received from detection device 437 and generate an output 439 to the status readout 440.

Figure 27:
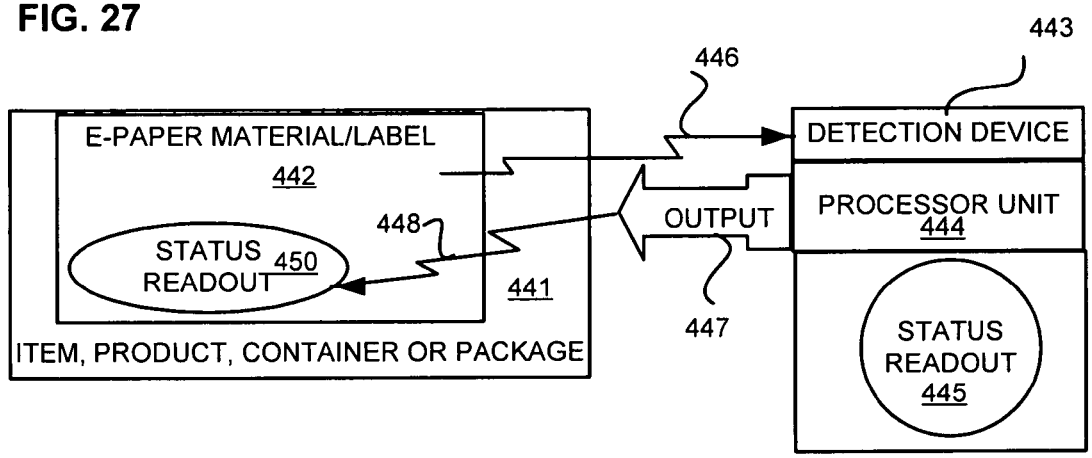

The schematic block diagram of FIG. 27 depicts another exemplary embodiment for an e-paper device that includes an e-paper label 442 with its associated (e.g., attached) item, product, container or package 441. In this embodiment, a first status readout component 450 is incorporated with the e-paper device. A detection device 443, processor unit 444, and second status readout 445 are in a location separated from the e-paper device. The processor unit 444 uses an appropriate security methodology to process scanned e-paper data that was obtained by detection device 443 via wireless signal 446 (or other communication channel). The processor unit 444 generates a first output 447 via a wireless communication link 448 (or other communication channel) to the status readout 440, and also a second output directly to second status readout 445. The two outputs could be substantially the same or significantly different, based on the needs of an authorized party having access to each status readout 450, 445.

Figure 28:
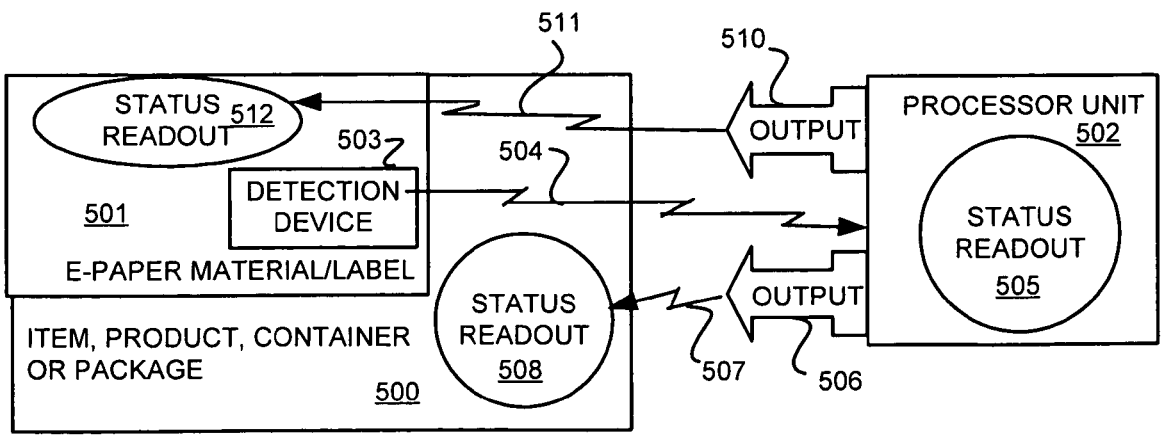

The schematic block diagram of FIG. 28 depicts an additional exemplary embodiment for an e-paper device that includes an e-paper label 501 with its associated (e.g., attached) item, product, container or package 500. In this embodiment, a first status readout component 512 and a detection device 503 are incorporated with the e-paper device. A second status readout 508 is incorporated on the item, product container or package 500. A processor unit 502 and third status readout 505 are in a location separated from the e-paper device. The processor unit 502 uses an appropriate security methodology to process scanned e-paper data that is received via wireless communication link 504. The processor unit 502 generates a first output 510 via a wireless communication link 511 (or other communication channel) to the first status readout 512, and also a second output 506 via a wireless communication link 507 (or other communication channel) to second status readout 508. The processor unit 502 generates a third output directly to status readout 505. The three outputs could be substantially the same or significantly different, based on the needs of authorized parties having access to each status readout 512, 508, 505.

Figure 29:
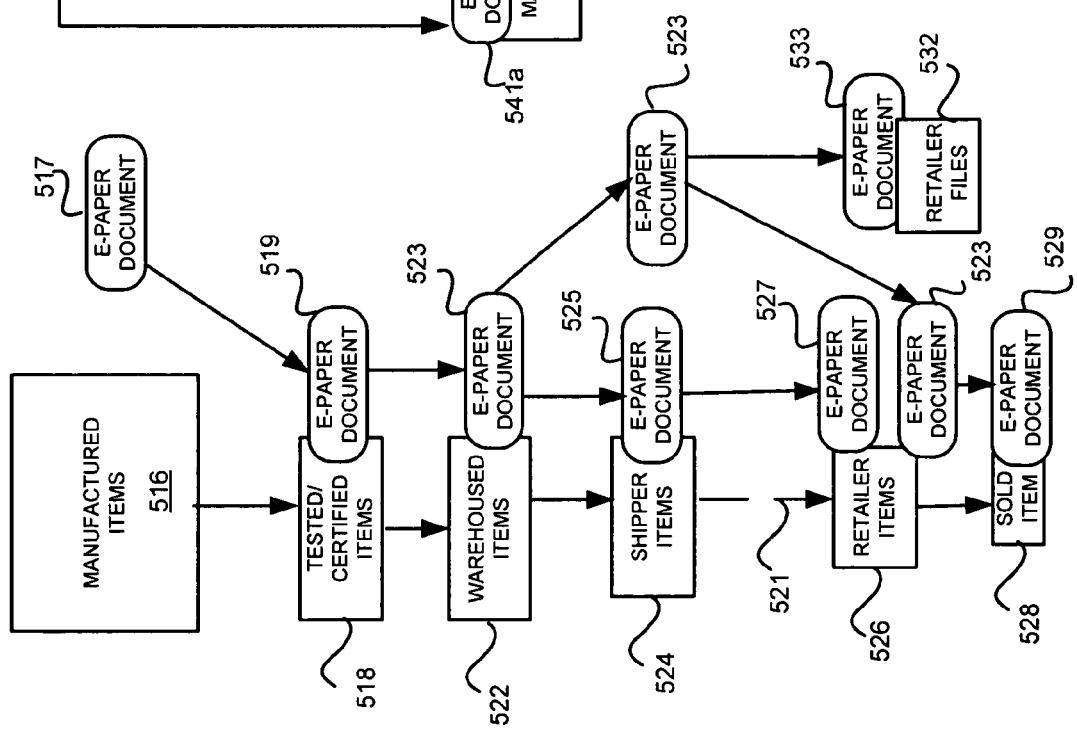
FIG. 29 is a schematic flow chart that illustrates an exemplary e-paper document that passes through different stages of being attached to or associated with a manufactured item.

The schematic flow chart process 515 of FIG. 29 illustrates an exemplary e-paper document associated with a manufactured item that passes through different stages of a supply chain. At each stage, authorized entities and/or persons may "write" (i.e., enter) data to the e-paper document and/or "read" (i.e., detect) data from the e-paper document. In that regard different versions of e-paper documents associated with the same item may exist, some versions with identical data entries and other versions with different data entries. Verification status checks may be made on a periodic or programmed basis as well as randomly anywhere along the supply chain path. Such verification status checks may occur while the e-paper document serves as a label that is physically attached to its associated item, and may also occur while e-paper document is separated from its associated item.

An initial e-paper document version 517 that may bear identity information related to an associated group of manufactured items 516 is depicted as being separated from its associated group of manufactured items 516. A later updated e-paper version 519 bearing new entries may be connected or correlated with groups of one or more tested/certified items 518. A further updated e-paper version 523 may be physically attached as a label to an individual or group of warehoused items 522.

One of the further updated e-paper versions 523 may bypass the intermediate shipping destinations en route to retailer files 532 maintained by a final store destination. A duplicate updated version 523 may become re-attached as a label to one or more retailer items. A final updated version 529 may accompany a sold item 528 to an ultimate recipient or purchaser, wherein the final updated version 529 is shown to be attached as a label directly to the sold item 528, or its package or container.

Other e-paper versions such as 525 may be attached or otherwise matched with associated shipper items 524 which proceed by various means of transportation (see arrow 521) to become inventory retailer items 526. The inventory retailer items 526 are shown as having an attached updated e-paper label version 527. This e-paper version 527 bearing detailed shipping entries may in some instances be removed from a sold item prior to delivery to the ultimate recipient or purchaser.

The recitation of the various e-paper document and label versions as disclosed in FIG. 29 is for purposes of illustration. Many other paths, supply chain destinations, e-paper document associations, and e-paper versions may be contemplated by those skilled in the art in order to obtain the advantages and benefits disclosed herein.

Figure 30:
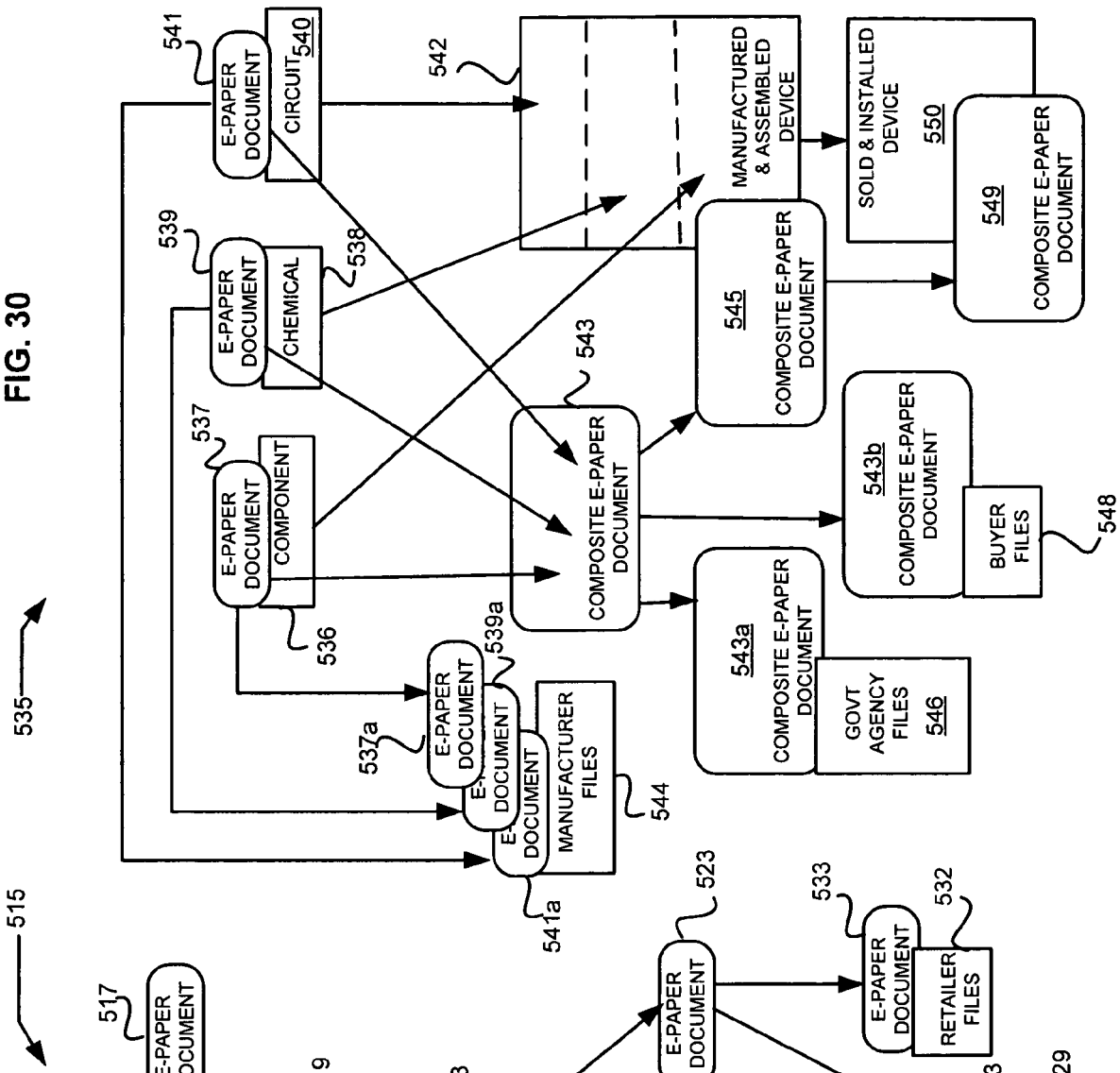
FIG. 30 is a schematic flow chart that illustrates multiple examples of individual and composite e-paper documents that pass through different stages of being attached to or associated with a manufactured and assembled device.

The schematic flow chart process 535 of FIG. 30 illustrates a further exemplary e-paper document associated with a manufactured/assembled device that passes through different stages of a supply chain. At each stage, authorized entities and/or persons may "write" (i.e., enter) data to the e-paper document and/or "read" (i.e., enter) data from the e-paper document. In that regard different versions of e-paper documents associated with the same item may exist, some versions with identical data entries and other versions with different data entries. Verification status checks may be made on a periodic or programmed basis as well as randomly anywhere along the supply chain path. Such verification status checks may occur while the e-paper document serves as a label that is physically attached to its associated item, and may also occur while e-paper document is separated from its associated item.

Initial e-paper document versions 537, 539, 541 may bear informational data related to their respective associated items shown as component 536, chemical 538, and circuit 540. In this exemplary embodiment the e-paper document versions 537, 539, 541 are depicted as being temporarily attached to their respective associated items during the manufacturing process. These items 536, 538, 540 may be manufactured by independent suppliers or by another internal company division for subsequent incorporation into a manufactured & assembled device 542. Updated e-paper versions 537a, 539a, 541a bearing shipping, testing or other pertinent informational data may be removed from the items and stored for future reference in manufacturer files 544.

A later composite e-paper document version 543 separated from its associated manufactured & assembled device 542 may incorporate some informational data from previous versions 537, 539, 541. Such composite version possibly having additional updated entries and designated 543a may be kept in government agency files 546. Such composite version possibly having other updated entries and designated 543b may be kept in buyer files 548.

A final e-paper document version 549 that may contain previously entered informational data from versions 537, 539, 541, 543 as well as bearing further updated entries is shown to be physically attached as a label to a sold & installed device 550.

The recitation of the various e-paper document and label versions as disclosed in FIG. 29 is for purposes of illustration. Many other paths, supply chain destinations, e-paper document associations, and e-paper versions may be contemplated by those skilled in the art in order to obtain the advantages and benefits disclosed herein.

An exemplary process embodiment 555 as shown in FIG. 31 provides for creating informational data from an authorized entity, which informational data regarding an item or product is intended to be non-alterable (block 556). The informational data is written in encrypted or encoded format on electronic paper material (block 557). Authentication indicia may be incorporated as part of the informational data, wherein the authentication indicia identifies the electronic paper material and/or the informational data as having originated from a provider of the particular item or product, or from an authorized third party (block 558). A security methodology is provided to enable verification confirmation with respect to the electronic paper material and/or the informational data (block 559).

Figure 32:
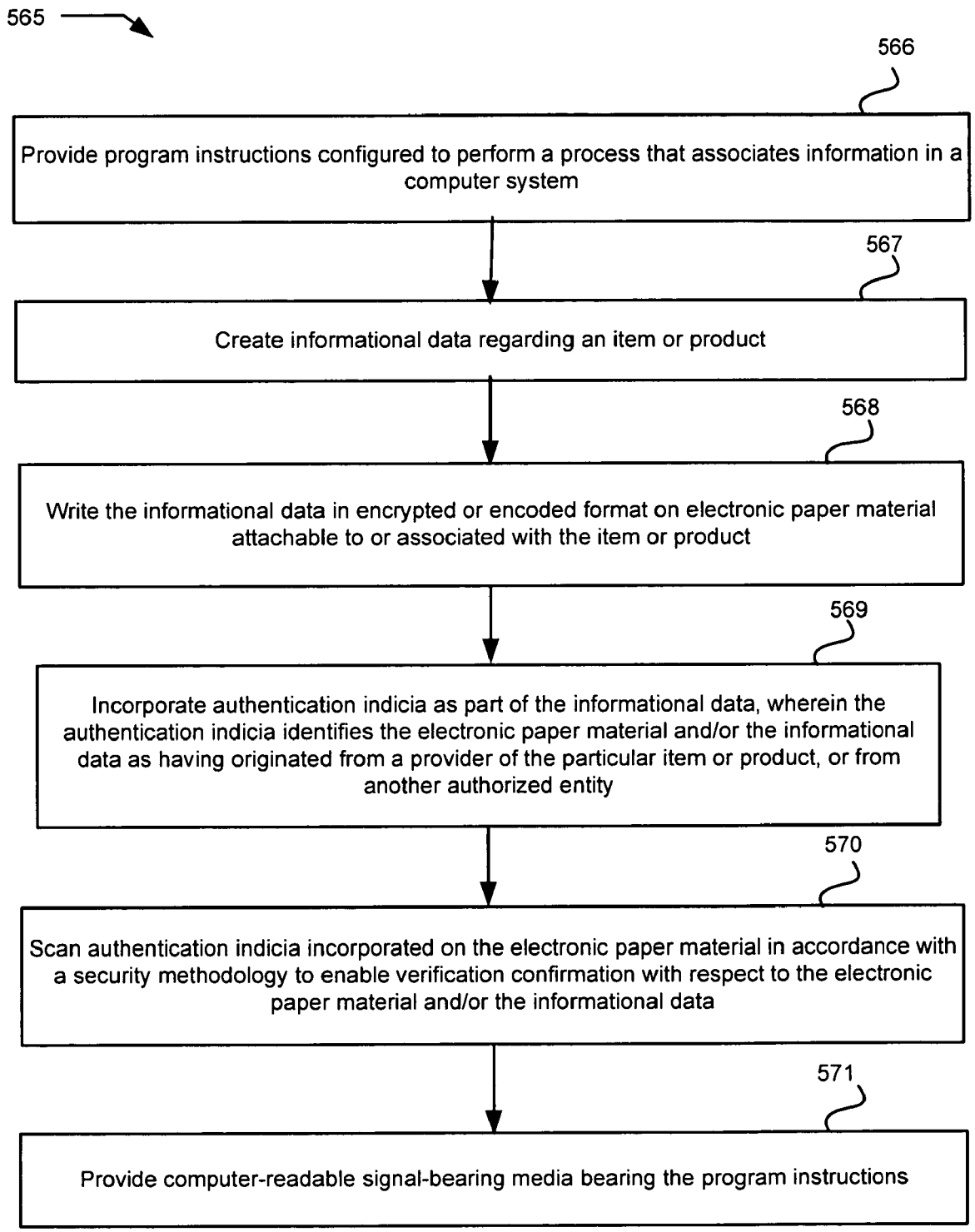
FIG. 32 is a high level flow chart showing an exemplary process incorporated in a computer program product.

The flow chart of FIG. 32 illustrates an exemplary computer program product embodiment 565 that provides program instructions configured to perform a process that associates information in a computer system (block 566). The process includes creating informational data regarding an item or product (block 567), and writing the informational data in encrypted or encoded format on electronic paper material attachable to or associated with the item or product.

The process may further include incorporating authentication indicia as part of the informational data, wherein the authentication indicia identifies the electronic paper material and/or the informational data as having originated from a provider of the particular item or product, or from another authorized entity (block 569). Another feature may include scanning authentication indicia incorporated on the electronic paper material in accordance with a security methodology to enable verification confirmation with respect to the electronic paper material and/or the informational data (block 570). The exemplary computer program product also provides computer-readable signal-bearing media bearing the program instructions (block 571).

Figure 33:
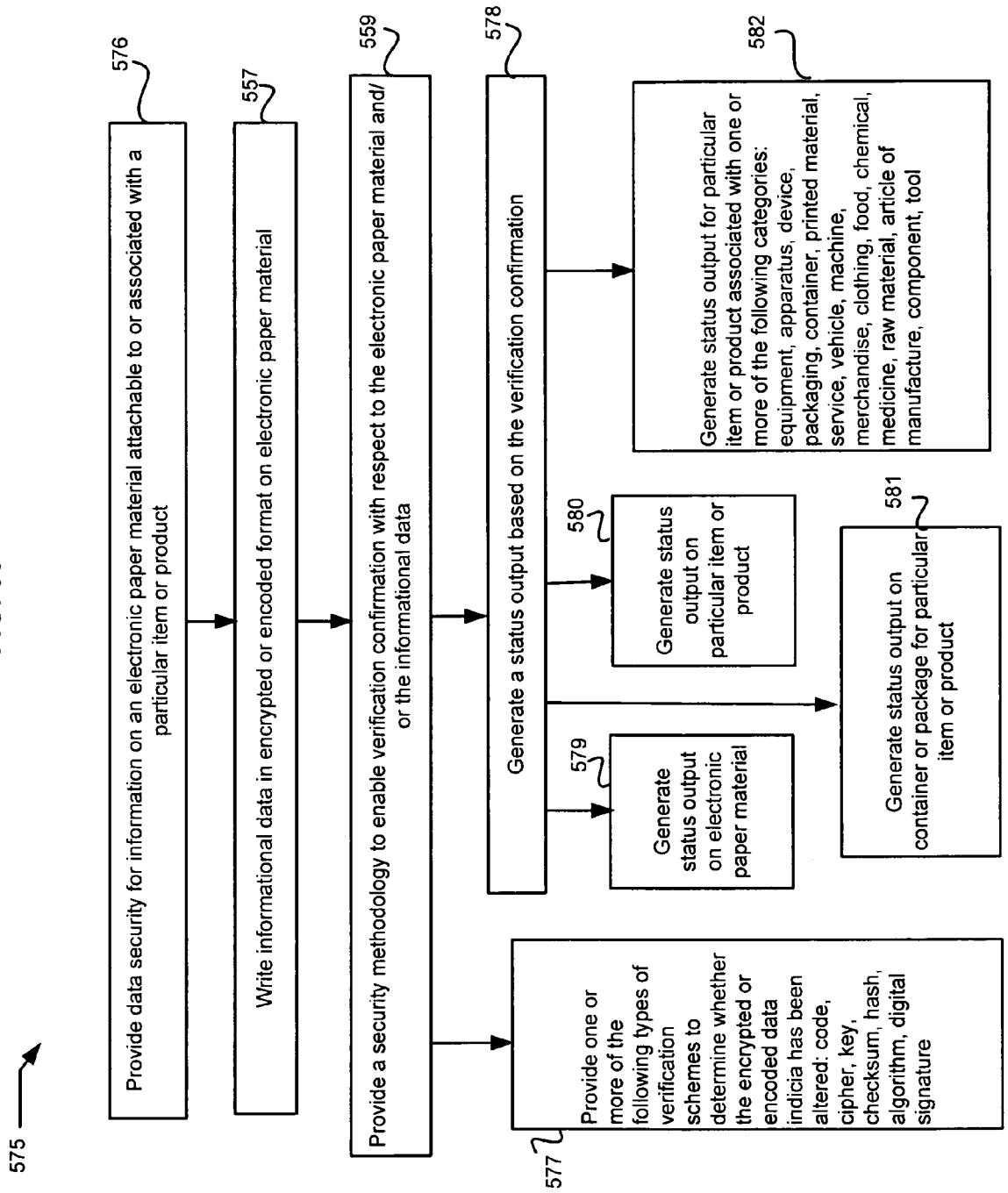
FIGS. 33-34 are more detailed flow charts showing further exemplary process features for additional embodiments.

Various additional aspects are included in the exemplary process 575 shown in the flow chart of FIG. 33, which provides data security for information on an electronic paper material attachable to or associated with a particular item or product (block 576). In addition to the previously described process blocks 557, 559, additional features may include generating a status output (block 578) based on a verification confirmation) with respect to the electronic paper material and/or the informational data (see block 559). The verification confirmation of block 559 may include providing one or more of the following types of verification schemes to determine whether the encrypted or encoded data indicia or other symbolic representation has been altered: code, cipher, key, checksum, hash, algorithm, and digital signature (block 577). Those skilled in the art will understand that other verification schemes can be implemented in the methods and systems disclosed herein.

Other aspects of the status output may include generating a status output on the electronic paper material (block 579), generating a status output on a particular item or product (block 580), and generating a status output on a container or a package for the particular item or product (block 581). Additional features may include generating a status output based on the verification confirmation for the particular item or product associated with one or more of the following categories: equipment, apparatus, device, packaging, container, printed material, services, vehicle, machine, merchandise, clothing, food, chemical, medicine, raw material, article of manufacture, component, and tool (block 582). Other categories of items and products are intended to be included, and the listing is not intended to be exhaustive but rather for purposes of illustration only.

Figure 34:
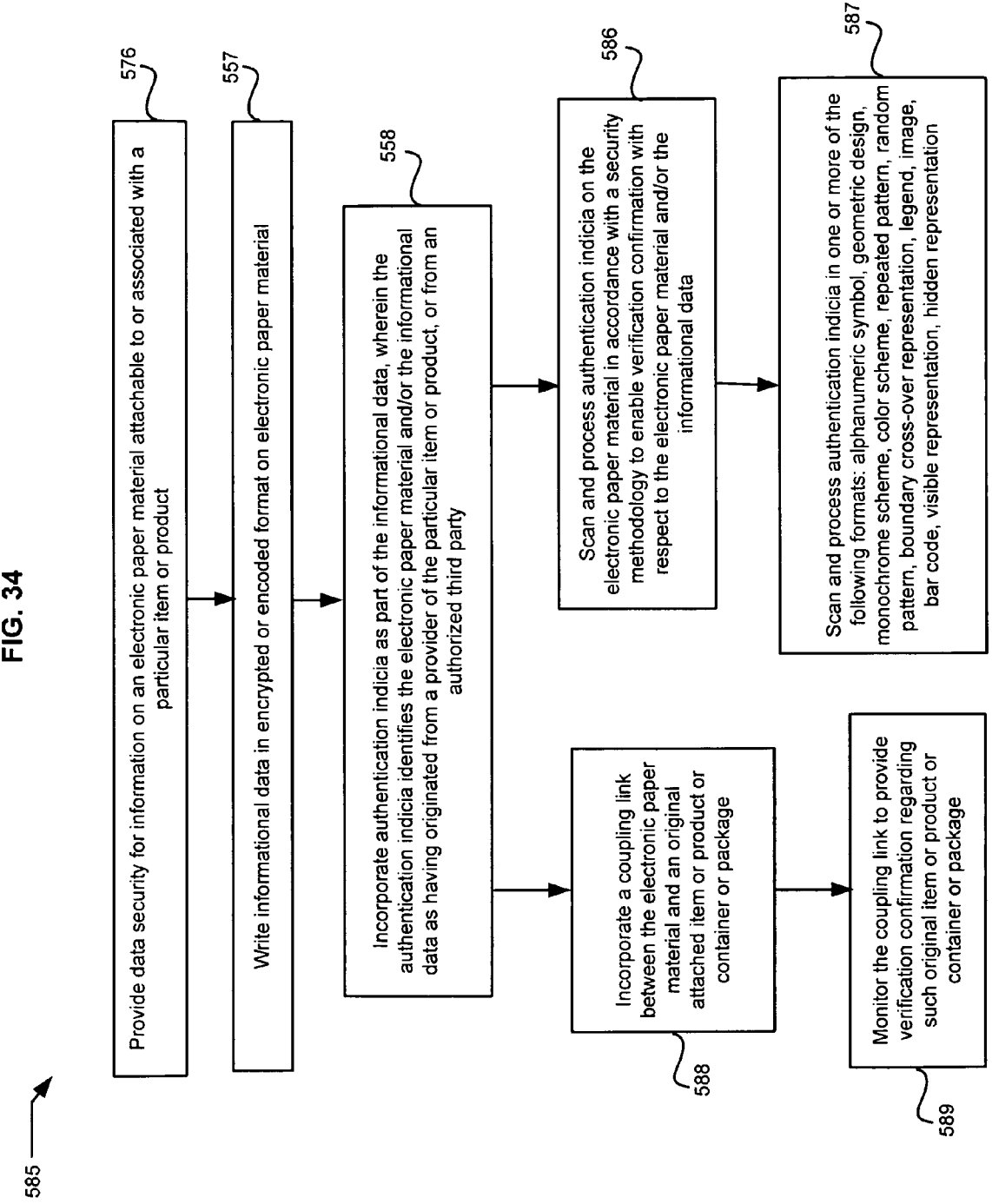

Referring to another process embodiment 585 shown in the flow chart of FIG. 34, an exemplary process includes the previously described features of blocks 576, 557, 558 as well as aspects involving scanning and processing authentication indicia on the electronic paper material. Such scanning and processing may be in accordance with a security methodology to enable verification confirmation with respect to the electronic paper material and/or the informational data (block 586), and may involve authentication indicia in one or more of the following formats: alphanumeric symbol, geometric design, monochrome scheme, color scheme, background, repeated pattern, random pattern, boundary cross-over representation, legend, image, bar code, visible representation, and hidden representation (block 587). Of course, other formats may be used in order to obtain the benefits of the various processes and systems disclosed herein.

Additional process features shown in the flow chart of FIG. 34 may include incorporating a coupling link between the electronic paper material and an original attached item or product or container or package (block 588), and monitoring the coupling link to provide verification confirmation regarding such original item or product or container or package (block 589).

Figure 35:
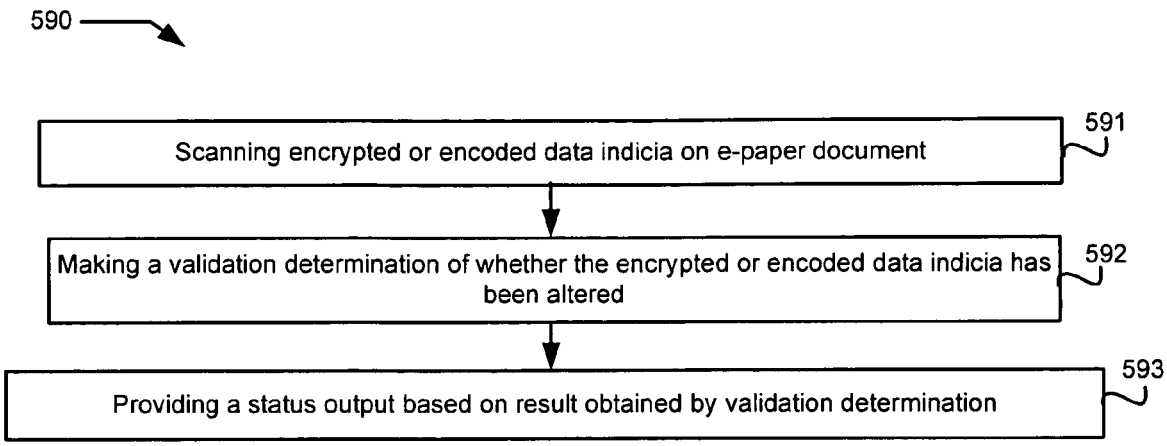
FIG. 35 is a high level flow chart showing another exemplary process for certain embodiments.

The flow chart of FIG. 35 shows another exemplary process 590 that includes scanning encrypted or encoded data indicia on an e-paper document (block 591), making a validation determination of whether the encrypted or encoded data indicia has been altered (block 592), and providing a status output based on a result obtained by the validation determination (block 593).

Figure 36:
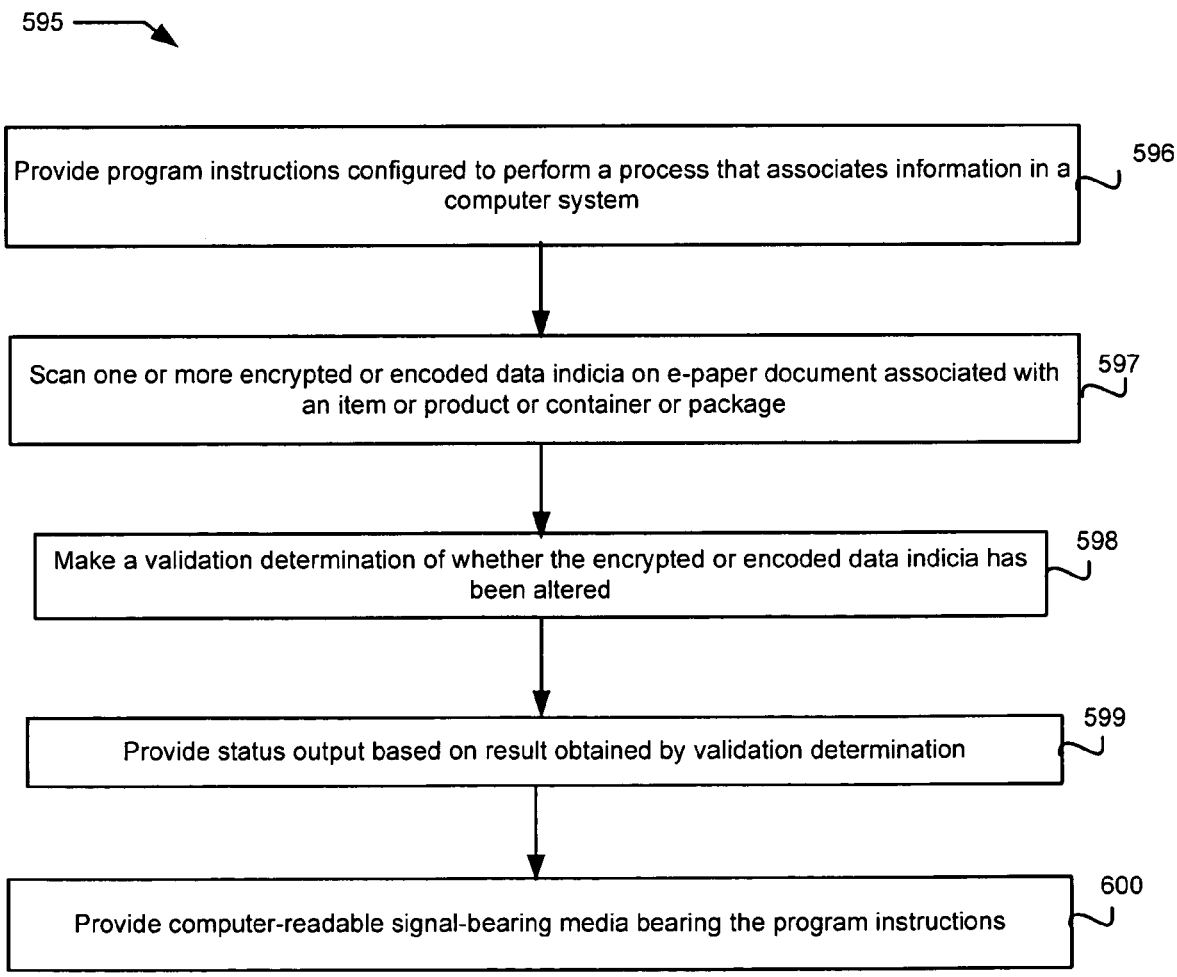
FIG. 36 is a high level flow chart showing a further exemplary process incorporated in a computer program product.

An exemplary computer program product embodiment 595 of FIG. 36 provides program instructions configured to perform a process that associates information in a computer system (block 596). The process includes scanning one or more encrypted or encoded data indicia on an e-paper document associated with an item or product or container or package (block 597), making a validation determination of whether the encrypted or encoded data indicia has been altered (block 598), and providing a status output based on a result obtained by the validation determination (block 599). The computer program product may further provide computer-readable signal-bearing media bearing the program instructions (block 600).

Figure 37:
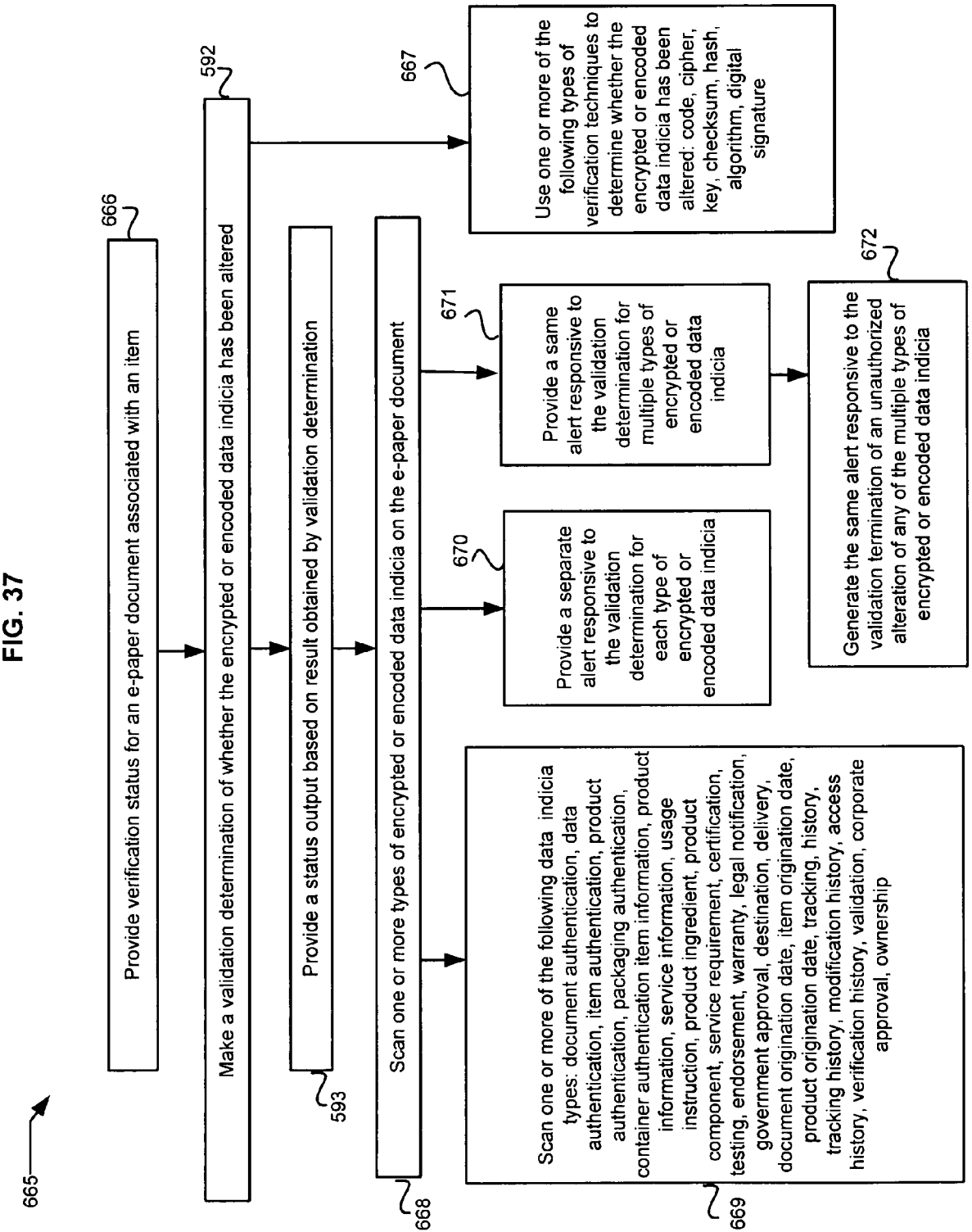
FIGS. 37-39 are more detailed flow charts showing additional exemplary process features.

The process embodiment 665 of FIG. 37 shows an implementation for providing verification status for an e-paper document associated with an item (block 666). The previously described validation determination (block 592) may include one or more following types of verification techniques to determine whether the encrypted or encoded data indicia has been altered: code, cipher, key, checksum, hash, algorithm, and digital signature (block 667).

The previously described status output (see block 593) may in some instances be based on scanning one or more types of encrypted or encoded data indicia on the e-paper document (block 668). As an exemplary list, one or more of the following data indicia types may be scanned: document authentication, data authentication, item authentication, product authentication, packaging authentication, container authentication, item information, product information, service information, usage instruction, product ingredient, product component, service requirement, certification, testing, endorsement, warranty, legal notification, government approval, destination, delivery, document origination date, item origination date, product origination date, tracking, history, tracking history, modification history, access history, verification history, validation, corporate approval, and ownership (block 669). Of course, other types of data indicia may be included.

Additional aspects may include providing a separate alert responsive to the validation determination for each type of encrypted or encoded data indicia (block 670), providing a same alert responsive to the validation determination for multiple types of encrypted or encoded data indicia (block 671), and generating the same alert responsive to the validation termination of an unauthorized alteration of any of the multiple types of encrypted or encoded data indicia (block 672).

Figure 38:
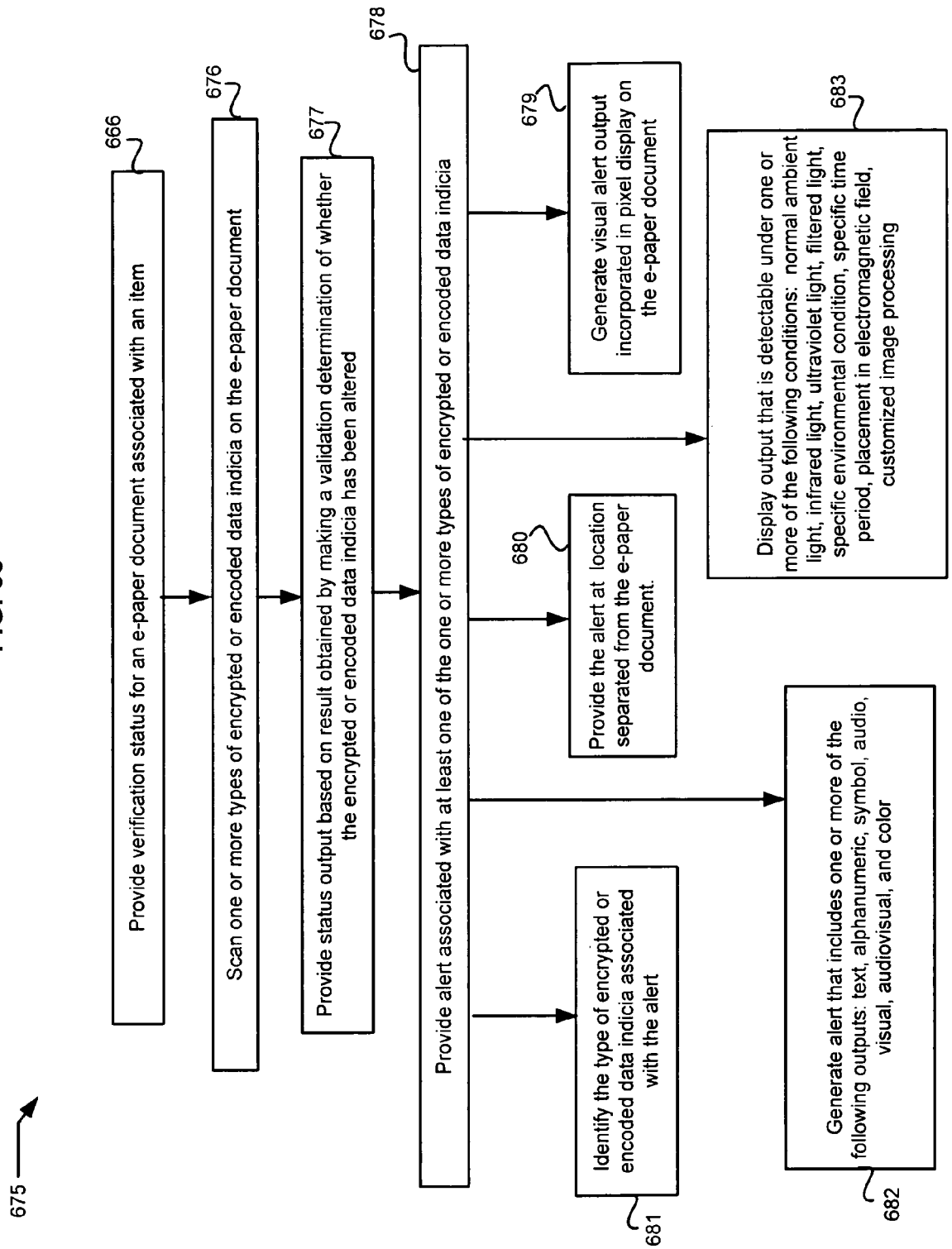

Another exemplary process embodiment 675 as shown in the flow chart of FIG. 38 provides verification status for an e-paper document associated with an item (block 666). Features may include scanning one or more types of encrypted or encoded data indicia on the e-paper document (block 676), providing a status output based on a result obtained by making a validation determination of whether the encrypted or encoded data indicia has been altered (block 677), and providing an alert associated with at least one of the one or more types of encrypted or encoded data indicia (block 678).

Various aspects regarding the alert may include generating a visual alert output incorporated in a pixel display on the e-paper (block 679), providing the alert at a location separated from the e-paper document (block 680), and identifying the type of encrypted or encoded data indicia associated with the alert (block 681).

Additional aspects regarding the alert may include generating an alert that includes one or more of the following outputs: text, alphanumeric, symbol, audio, visual, audiovisual, and color (block 682), and may also include displaying an output that is detectable under one or more of the following conditions: normal ambient light, infrared light, ultraviolet light, filtered light, specific environmental condition, specific time period, placement in electromagnetic field, and customized image processing (block 683). Of course, other types of outputs and other types of detection conditions may be included.

Figure 39:
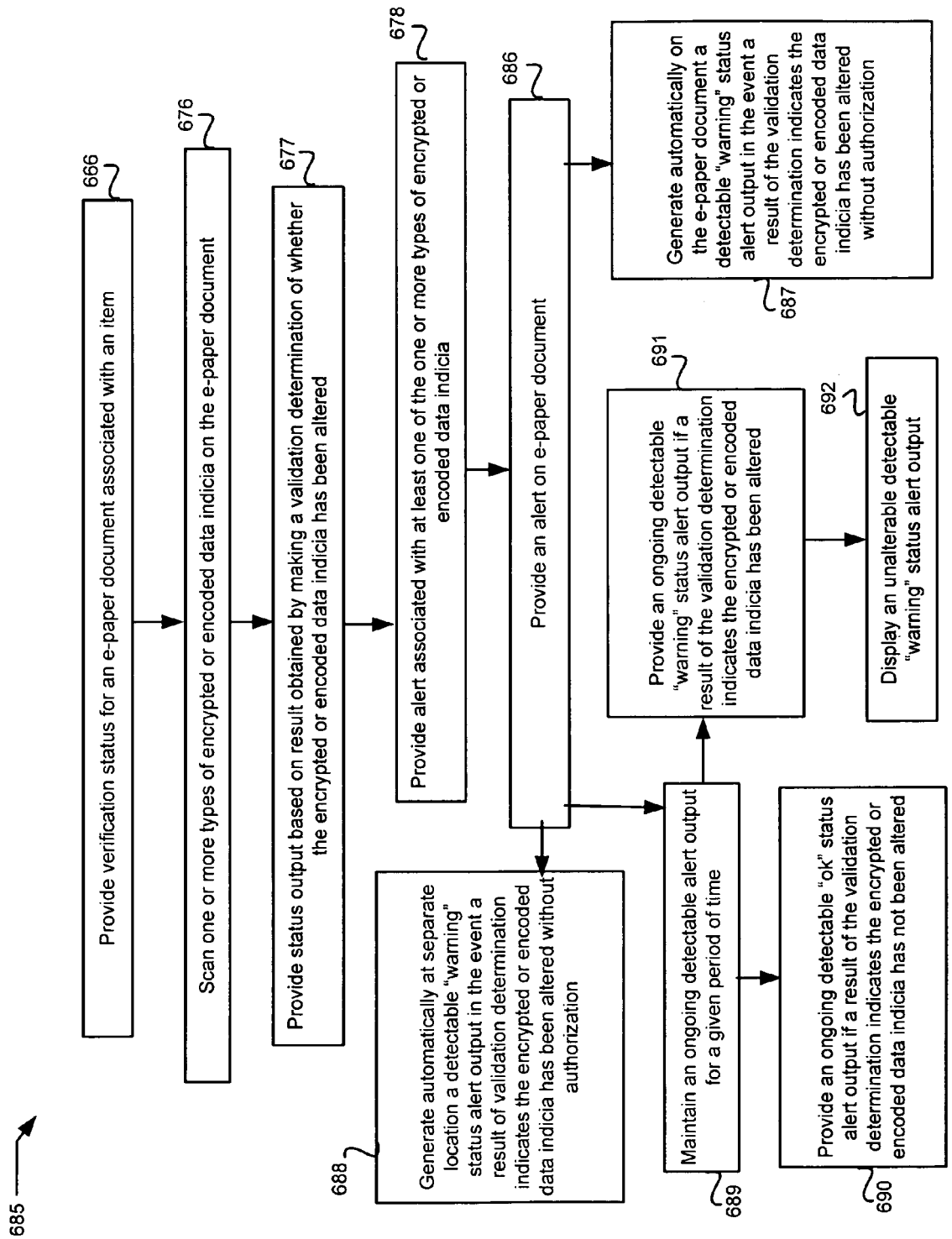

Referring to the flow chart of FIG. 39, another exemplary process 685 includes the previously described features of blocks 666, 676, 677, 678 wherein an alert is provided on the e-paper document (block 686). Such an alert may have different exemplary implementations including generating automatically on the e-paper document a detectable "warning" status alert output in the event a result of the validation determination indicates the encrypted or encoded data indicia has been altered without authorization (block 687), and/or further including generating automatically at a separate location a detectable "warning" status alert output in the event a result of the validation determination indicates the encrypted or encoded data indicia has been altered without authorization (block 688).

Additional exemplary alert implementations include maintaining an ongoing detectable alert output for a given period of time (block 689), providing an ongoing detectable "ok" status alert output if a result of the validation determination indicates the encrypted or encoded data indicia has not been altered (block 690), providing an ongoing detectable "warning" status alert output if a result of the validation determination indicates the encrypted or encoded data indicia has been altered (block 691), and displaying an unalterable detectable "warning" status alert output (block 692).

Figure 40:
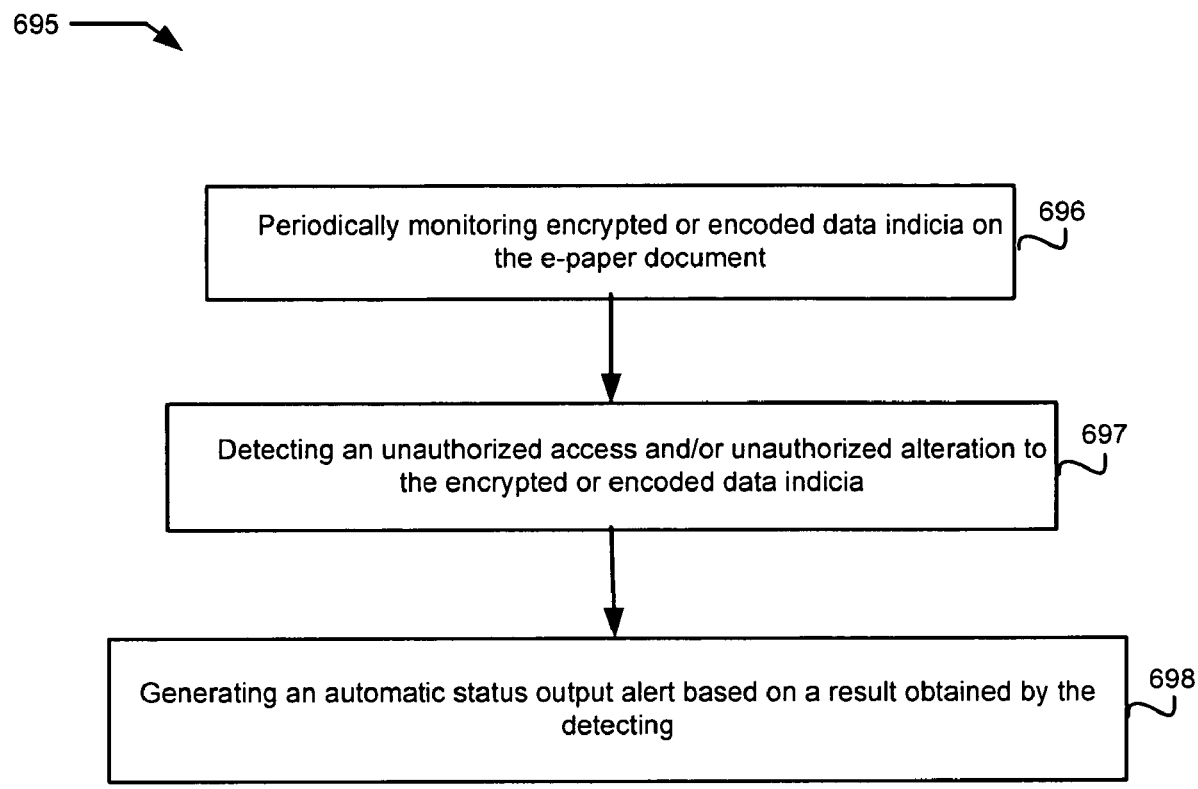
FIG. 40 is a high level flow chart showing an additional exemplary process for certain embodiments.

The high level flow chart of FIG. 40 shows another exemplary process 695 that includes periodically monitoring encrypted or encoded data indicia on the e-paper document (block 696), detecting an unauthorized access and/or unauthorized alteration to the encrypted or encoded data indicia (block 697), and generating an automatic status output alert based on a result obtained by said detecting (block 698).

Figure 41:
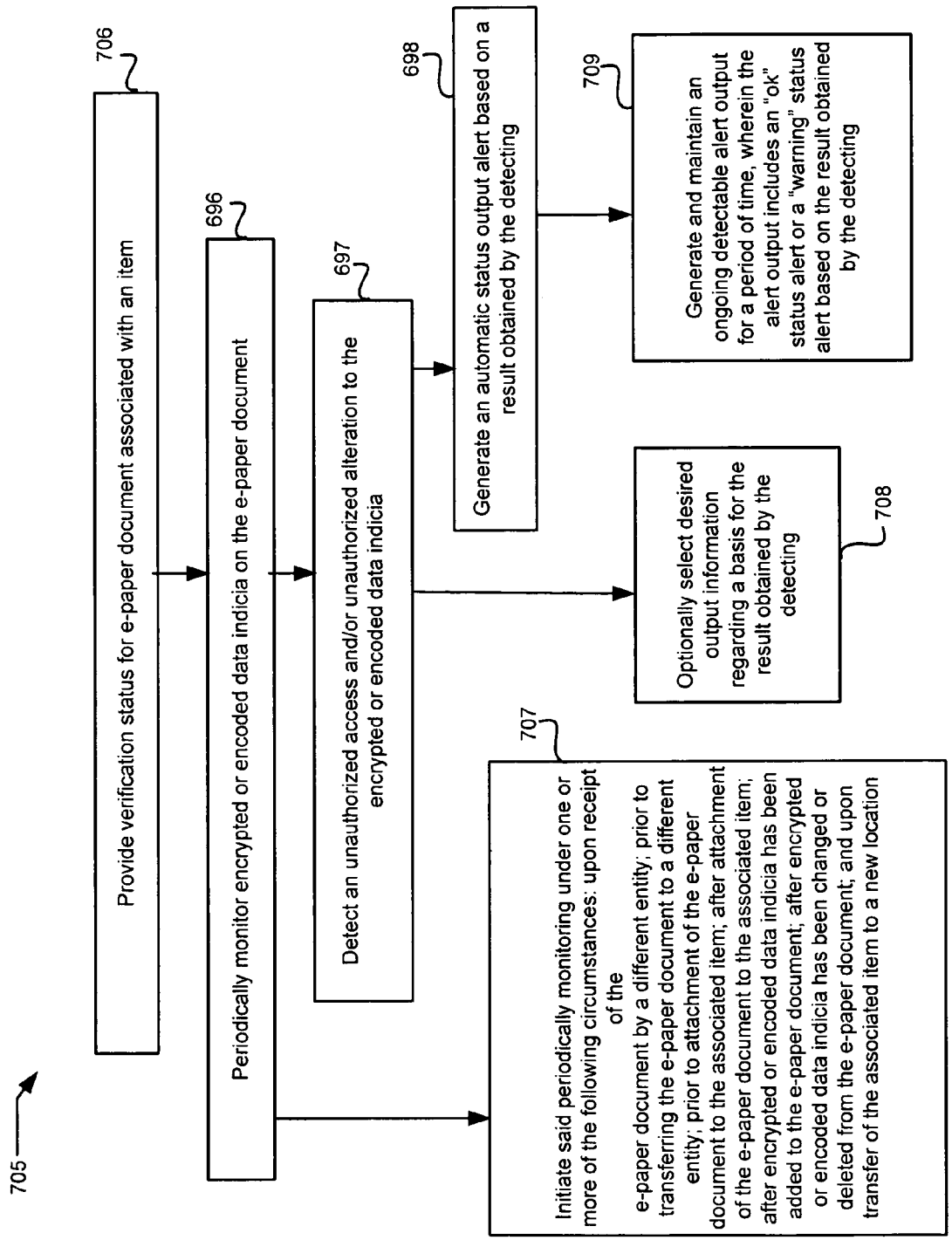
FIG. 41 is a more detailed flow chart showing other exemplary process features for various embodiments.

Referring to the process embodiment 705 of FIG. 41, the previously described features of blocks 696, 697, 698 are shown with additional features for providing verification status for an e-paper document associated with an item (block 706). Such additional process features may include initiating the periodically monitoring of block 696 under one or more of the following circumstances: upon receipt of the e-paper document by a different entity; prior to transferring the e-paper document to a different entity; prior to attachment of the e-paper document to the associated item; after attachment of the e-paper document to the associated item; after encrypted or encoded data indicia has been added to the e-paper document; after encrypted or encoded data indicia has been changed or deleted from the e-paper document; and upon transfer of the associated item to a new location (block 707).

Additional process features may include generating and maintaining an ongoing detectable alert output for a period of time, wherein the alert output includes an "ok" status alert or a "warning" status alert based on the result obtained by said detecting (block 709). Another process feature may include optionally selecting desired output information regarding a basis for the result obtained (block 708) by the detecting feature (see block 697).

The processes of FIGS. 31-41 can be implemented with various types of technology, including but not limited to hardware, firmware and/or software systems based on computerized data communications and processing as discussed in more detail herein. Programmed implementations can run on multiple computer devices or run on an integrated computer system, depending on the circumstances.

It will also be understood by those skilled in the art that the various communication links can be separated into different communication channels or media as well as combined into an integrated broadband or narrowband link such as wired, wireless, cable, etc. It is further understood that integrated or separate modules can be provided for user interface functions, for writing/reading/scanning functions, for processing functions, for transceiver functions, and/or for output functions. The particular exemplary systems disclosed herein are provided only for illustration.

The read/write access interfaces disclosed herein for multiple users are for purposes of illustration, and persons skilled in the art will understand that various types of communication links can be utilized to achieve the necessary functional interactions between authorized users (also in some instances authorized third parties) and e-paper material, as well as between authorized users (also in some instances authorized third parties) and the status indicators (e.g., alert devices). It will be further understood that exemplary user interfaces are capable of operable connection to a communication link in order for an authorized party to send and receive permissible informational data relating to the verification status of e-paper material, e-paper documents, e-paper labels, and the like.

The exemplary system and device embodiments shown in FIGS. 1-6 and 13-30 along with other components, devices, know-how, skill and techniques that are known in the art have the capability of implementing and practicing the methods and processes shown in FIGS. 31-41. It is to be understood that the methods and processes can be incorporated in one or more computer program products with a carrier medium having program instructions carried or stored thereon. However it is to be further understood that other systems, apparatus and technology may be used to implement and practice such methods and processes.

It will be understood from the description and drawings herein that various components, sub-components, modules, and peripherals can be incorporated in a system for protecting information on an electronic paper device. The e-paper device may include an e-paper document or e-paper label with encoded or encrypted data relating to an associated item or product or service or container or package. The system may include a sensing device capable of reading the encoded or encrypted data, and a processor unit operably coupled to the sensing device to determine verification of any alteration or deletion of the encoded or encrypted data. The system may further include a status indicator that receives an input from the processor unit regarding a verification status for the encoded or encrypted data.

In some embodiments the status indicator may be incorporated with the e-paper material. In other instances the status indicator is incorporated with the associated item or product or container or package. Some implementations include the status indicator as part of a unit separated from the e-paper material. Also in certain embodiments the status indicator is included with the processor unit, and in some implementations may be included with the sensing device.

As disclosed herein, the sensing device may include a scanner reading the encoded or encrypted data in one or more of the following formats: alphanumeric symbol, geometric design, monochrome scheme, color scheme, background, repeated patterns, random patterns, boundary cross-over representations, legend, image, bar code, visible representation, and hidden representation.

As further disclosed herein, the sensing device in some embodiments is capable of reading the encoded or encrypted data under one or more of the following conditions: normal ambient light, infrared light, ultraviolet light, filtered light, specific environmental condition, specific time period, placement in electromagnetic field, and customized image processing. The sensing device may further include a scanner for scanning authentication indicia on said electronic paper material to identify said electronic paper material and/or said encoded or encrypted data as having originated from a provider of the item or product or service or from another authorized entity.

In some embodiments disclosed here, the e-paper verification system may be configured (in some instances programmed) to generate an "ok" status output if a verification confirmation indicates that that electronic paper material and/or the informational data has not been altered. The reference to "ok" is not limited to this term, but rather includes any type of output, display, communication, or other indication that a verification check has not detected or identified any apparent validation or authentication problem.

The e-paper verification system also may be configured (in some instances programmed) to generate a "warning" status output if the verification confirmation indicates that that electronic paper material and/or the informational data has been altered. The reference to "warning" is not limited to this term, but rather includes any type of output, display, communication, or other indication that a verification check has detected or identified an apparent validation or authentication problem.

With respect to embodiments wherein the e-paper material is attached to an associated item or product or container or package, the sensing device may include a scanner for determining a status of a coupling link with an original attached item or product or container or package, to provide confirmation that the electronic paper material has not been detached from its original item or product or container or package. In some instances the system may be programmed to monitor the coupling link between the electronic paper material and an original attached item or product or container or package, to provide verification confirmation regarding such original item or product or container or package The processor unit of an e-paper verification system as disclosed herein may include one or more of the following types of verification schemes to determine whether the encrypted or encoded data indicia has been altered: code, cipher, key, checksum, hash, algorithm, and digital signature. It is further understood that such encoded or encrypted data may be written by or on behalf of a person or entity from one or more of the following categories: item source, product maker, product manufacturer, product distributor, product wholesaler, product retailer, product dealer, service provider, service franchisee, service agency, and company subsidiary.

One aspect of the disclosed e-paper device includes encoded or encrypted data written by or on behalf of an authorized entity regarding one or more of the following types of informational data: document authentication, data authentication, item authentication, product authentication, packaging authentication, container authentication, item information, product information, services information, receipt acknowledgement, billing term, invoice data, usage instruction, product ingredient, product component, service requirement, certification, testing, endorsement, warranty, legal notification, government approval, destination, delivery, document origination date, item origination date, product origination date, tracking, history, tracking history, modification history, access history, verification history, validation, corporate approval, and ownership.

One of the system components disclosed herein is reader device for use with electronic paper material having label-type information thereon. The reader device may include a sensor that detects authentication indicia in one or more of the following categories: alphanumeric symbol, geometric design, monochrome scheme, color scheme, background, repeated pattern, random pattern, boundary cross-over representation, legend, image, bar code, visible representation, and hidden representation. An aspect of the system provides such authentication indicia to establish that the electronic paper material and/or the informational data and/or an associated item actually originated from a provider of the item or from another authorized entity.

A further aspect of the disclosed features provides encrypted or encoded informational data written by or on behalf of one or more of the following: a provider or maker or manufacturer or distributor or seller of the related item.

Another aspect provides one or more of the following types of authentication indicia: authentication indicia at least partially included in the data portion; authentication indicia separated from the data portion; authentication indicia intermixed with the informational data; authentication indicia separated from the information data; authentication indicia detectable on one surface of the electronic paper material, and authentication indicia on both surfaces of the electronic paper material.

Some embodiments include a status indicator for providing an output based on a verification confirmation with respect to the authentication indicia. An exemplary status indicator may include an output based on the verification confirmation regarding the authenticity of the e-paper material.

Other exemplary status indicators may include an output based on the verification confirmation regarding the authenticity of the informational data. Other status indicator outputs may be based on a verification confirmation with respect to the coupling link between an e-paper document or label and its associated item, product, container or package.

Some coupling link implementations include a circuit link between the electronic paper material and its associated item or product or container or package. Some embodiments provide a coupling link that includes an encrypted or encoded symbolic representation on the electronic paper material that correlates with another symbolic representation on the related product or container or package.

Some system and method embodiments disclosed here include scanning one or more types of encrypted or encoded data indicia on an e-paper document associated with an item or product or container or package, and making a validation determination of whether the encrypted or encoded data indicia has been altered. A status output is provided that is based on a result obtained by the validation determination. The aforementioned validation process may be incorporated in a computer program product that includes signal-bearing media. The signal bearing media may include storage media, and may also include communication media.

Other aspects of a process embodiment capable of being incorporated in a computer program product include providing the status output on the e-paper document. A detectable "ok" alert may be provided on the e-paper document as well as on a separate unit if a result of the validation determination indicates the encrypted or encoded data indicia has not been altered. Similarly a detectable "warning" alert may be provided on the e-paper document as well as on a separate unit if a result of the validation determination indicates that any of the encrypted or encoded data indicia has been altered.

Additional process features capable of being incorporated in a computer program product include displaying for a period of time an ongoing detectable "warning" alert on the electronic paper document, as well as on the item or product or container or package associated with the e-paper document. Another aspect may provide two or more status outputs at different locations, respectively, wherein different verification information be displayed or communicated at each status output. In some instances, a status alert may identify the type of encrypted or encoded data indicia which form a basis for the result of the validation determination.

A further aspect of an output alert may include generating automatically on the e-paper document and/or at a separate location a detectable "warning" status alert output in the event a result of the validation determination indicates the encrypted or encoded data indicia has been altered without authorization.

The verification status output indicator implementation may include multiple alert indicators, which individually can be incorporated with an associated item that is included in one or more of the following categories: product, equipment, apparatus, device, packaging, container, printed material, service, vehicle, machine, merchandise, clothing, food, chemical, medicine, raw material, article of manufacture, component, and tool. Of course, other categories may also be included. Such a status output indicator may include an alert device incorporated with a sensor device and/or with a processor unit.

Some alert indicator embodiments may provide an identity of a type of encrypted or encoded information determined by said processor unit to have been altered. Other aspects of an exemplary alert indicator may include a pixel display on the e-paper document, and a further aspect may include an unalterable display on the e-paper document, as well as in some instances an unalterable display on its associated item, product, container or package.

Various system and method embodiments disclosed herein are used to control the writing on electronic paper (e-paper). An e-paper device may incorporate authentication indicia as part of informational data written on e-paper material. The informational data is protected by a security methodology that is accessible to authorized entities. A reader device may be used to help make a verification determination of whether encrypted or encoded data has been altered. In some instances an output alert operably coupled to the reader device serves as a verification status indicator.

It will be understood by those skilled in the art that the various components and elements disclosed in the block diagrams herein as well as the various steps and sub-steps disclosed in the flow charts herein may be incorporated together in different claimed combinations in order to enhance possible benefits and advantages.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

As a further definition of "open" terms in the present specification and claims, it will be understood that usage of a language construction "A or B" is generally interpreted as a non-exclusive "open term" meaning: A alone, B alone, A and B together.

Although various features have been described in considerable detail with reference to certain preferred embodiments, other embodiments are possible. Therefore, the spirit or scope of the appended claims should not be limited to the description of the embodiments contained herein.

The invention claimed is:

1. A method for providing verification status for an e-paper document having an electronically written image associated with an item, comprising:
    scanning the image and encrypted or encoded data indicia included in the image on the e-paper document;
    making a validation determination using the encrypted or encoded data indicia to determine whether the image has been altered; and
    providing a status output based on a result obtained by the validation determination, wherein said providing the status output includes:
        providing an alert associated with at least one of the one or more types of encrypted or encoded data indicia,
        providing the alert on the e-paper document and/or on the associated item or product or container or package,
        maintaining an ongoing detectable alert output for a given period of time,
        providing an ongoing detectable "warning" status alert output if a result of the validation determination indicates the encrypted or encoded data indicia has been altered, and
        displaying an unalterable detectable "warning" status alert output.

2. The method of claim 1 wherein said making the validation determination includes:
    using one or more of the following types of data structures to determine whether the encrypted or encoded data indicia has been altered: code, cipher, key, checksum, hash, algorithm, and digital signature.

3. The method of claim 1 wherein said providing the status output includes:
    providing a separate alert responsive to the validation determination for each type of encrypted or encoded data indicia.

4. The method of claim 1 wherein said providing the status output includes:
    providing a same alert responsive to the validation determination for multiple types of encrypted or encoded data indicia.

5. The method of claim 4 wherein said providing the same alert includes:
    generating the same alert responsive to the validation termination of an unauthorized alteration of any of the multiple types of encrypted or encoded data indicia.

6. The method of claim 1 wherein said scanning one or more types includes:
    scanning one or more of the following types of encrypted or encoded data indicia: document authentication, data authentication, item authentication, product authentication, packaging authentication, container authentication, item information, product information, service information, usage instruction, product ingredient, product component, service requirement, certification, testing, endorsement, warranty, legal notification, government approval, destination, delivery, document origination date, item origination date, product origination date, tracking, history, tracking history, modification history, access history, verification history, validation, corporate approval, and ownership.

7. The method of claim 1 wherein said providing the alert includes:
    identifying the type of encrypted or encoded data indicia associated with the alert.

8. The method of claim 1 wherein said providing the alert includes:
    providing the alert at a location separated from the e-paper document.

9. The method of claim 1 wherein said providing the alert includes:
    generating the alert that includes one or more of the following outputs: text, alphanumeric, symbol, audio, visual, audiovisual, and color.

10. The method of claim 1 wherein said providing the alert includes:
    displaying an output that is detectable under one or more of the following conditions: normal ambient light, infrared light, ultraviolet light, filtered light, specific environmental condition, specific time period, placement in electromagnetic field, and customized image processing.

11. The method of claim 1 wherein said providing the alert includes:
    generating a visual alert output incorporated in a pixel display on the e-paper document.

12. The method of claim 1 wherein said providing an alert on the e-paper document includes:
    generating automatically on the e-paper document and/or at a separate location a detectable "warning" status alert output in the event a result of the validation determination indicates the encrypted or encoded data indicia has been altered without authorization.

13. The method of claim 1 wherein said maintaining the ongoing detectable alert output includes:
    providing an ongoing detectable "ok" status alert output if a result of the validation determination indicates the encrypted or encoded data indicia has not been altered.

14. A system for indicating a verification status of an e-paper document having an electronically written image related to an associated item, comprising:
    a sensor device for scanning encrypted or encoded information included in the image incorporated in the e-paper document;
    a processor unit for performing a security validation on the encrypted or encoded information to determine whether the image has been altered; and an alert indicator on the e-paper document that provides a first output responsive to the security validation performed by said processor unit, wherein the first output is associated with at least one of the one or more types of encrypted or encoded data indicia, wherein the first output is provided on the e-paper document and/or on the associated item or product or container or package, wherein the first output is maintained as an ongoing detectable alert output for a given period of time, wherein the first output is provided as an ongoing detectable "warning" status alert output if a result of the validation determination indicates the encrypted or encoded data indicia has been altered, and wherein the first output is displayed an unalterable detectable "warning" status alert output.

15. The system of claim 14 wherein said sensor device includes:
   another alert indicator that provides a second output responsive to the security validation performed by said processor unit.

16. The system of claim 15 wherein the another alert indicator is incorporated with the associated item.

17. The system of claim 16 wherein the another alert indicator is incorporated with the associated item that is included in one or more of the following categories: product, equipment, apparatus, device, packaging, container, printed material, service, vehicle, machine, merchandise, clothing, food, chemical, medicine, raw material, article of manufacture, component, and tool.

18. The system of claim 15 wherein the another alert indicator is incorporated with the sensor device and/or with the processor unit.

19. The system of claim 15 wherein the second output is different from the first output.

20. The system of claim 14 wherein said alert indicator is configured to generate automatically a detectable "warning" status output alert if a result of the validation determination indicates the encrypted or encoded data indicia has been altered without authorization.

21. The system of claim 14 wherein said sensor scans multiple types of encrypted or encoded information; and
   wherein said alert indicator provides a "warning" alert output responsive to an alteration detected in any of the multiple types of encrypted or encoded information.

22. The system of claim 21 wherein said alert indicator further provides an identity of a type of encrypted or encoded information determined by said processor unit to have been altered.

23. The system of claim 14 wherein said alert indicator provides an "ok" alert output responsive to no alteration detected in the encrypted or encoded information.

24. The system of claim 14 wherein said alert indicator includes a pixel display on the e-paper document.

25. The system of claim 14 wherein said visual alert indicator includes a display detectable under one or more of the following conditions: normal ambient light, infrared light, ultraviolet light, filtered light, specific environmental condition, specific time period, placement in electromagnetic field, and customized image processing.

26. The system of claim 14 wherein said sensor device includes a scanner capable of reading encrypted or encoded information that includes one or more of the following categories: alphanumeric text, symbol, geometric design, monochrome scheme, color scheme, repeated pattern, random pattern, boundary cross-over representation, legend, image, bar code, and hidden representation.

27. The system of claim 14 where said sensor device includes a scanner capable of reading encrypted or encoded information located on the e-paper document and/or on the associated item or product or container or package.

28. A computer program product comprising:
   a computer-readable recordable medium bearing program instructions configured to perform a process that associates information in a computer system, the process including scanning one or more types of encrypted or encoded data indicia on an e-paper document having an electronically written image associated with an item or product or container or package, making a validation determination using the encrypted or encoded data indicia to determine whether the image has been altered, and providing a status output based on a result obtained by the validation determination, wherein said providing the status output includes:
      providing an alert associated with at least one of the one or more types of encrypted or encoded data indicia,
      providing the alert on the e-paper document and/or on the associated item or product or container or package,
      maintaining an ongoing detectable alert output for a given period of time,
      providing an ongoing detectable "warning" status alert output if a result of the validation determination indicates the encrypted or encoded data indicia has been altered, and
      displaying an unalterable detectable "warning" status alert output.

29. The computer program product of claim 28, wherein the media includes a storage media.

30. The computer program product of claim 28, wherein said providing the status output includes:
   providing a detectable "ok" alert if a result of the validation determination indicates the encrypted or encoded data indicia has not been altered.

31. The computer program product of claim 28, wherein said providing a detectable "warning" alert includes:
   displaying for a period of time an ongoing detectable "warning" alert on the item or product or container or package physically associated with the e-paper document.

32. The computer program product of claim 28, wherein said providing the status output includes:
   providing two or more status outputs at different locations, respectively.

33. The computer program product of claim 32, wherein said providing two or more status outputs includes:
   providing at least two status outputs that include different information regarding the validation determination.

34. The computer program product of claim 33, wherein said providing at least two status outputs includes:
   identifying in at least one status output the type of encrypted or encoded data indicia which form a basis for the result of the validation determination.

35. A method for providing verification status for an e-paper document associated with an item, comprising:
   periodically monitoring encrypted or encoded data indicia on the e-paper document;
   detecting an unauthorized alteration to the encrypted or encoded data indicia; and
   generating an automatic status output alert based on a result obtained by said detecting, wherein the generating the automatic status output includes:
      providing an alert associated with at least one of the one or more types of encrypted or encoded data indicia, providing the alert on the e-paper document and/or on the associated item or product or container or package, maintaining an ongoing detectable alert output for a given period of time, providing an ongoing detectable "warning" status alert output if a result of the validation determination indicates the encrypted or encoded data indicia has been altered, and displaying an unalterable detectable "warning" status alert output.

36. The method of claim 35 wherein said periodically monitoring includes:

initiating said periodically monitoring under one or more of the following circumstances:

upon receipt of the e-paper document by a different entity;

prior to transferring the e-paper document to a different entity;

prior to attachment of the e-paper document to the associated item;

after attachment of the e-paper document to the associated item;

after encrypted or encoded data indicia has been added to the e-paper document;

after encrypted or encoded data indicia has been changed or deleted from the e-paper document; and upon transfer of the associated item to a new location.

37. The method of claim 35 further comprising:

optionally selecting desired output information regarding a basis for the result obtained by said detecting.

* * * * *